(12) United States Patent
Zhang et al.

(10) Patent No.: US 11,352,353 B2
(45) Date of Patent: Jun. 7, 2022

(54) HETEROCYCLIC COMPOUND SERVING AS FGFR4 INHIBITOR

(71) Applicant: Hangzhou Innogate Pharma Co., Ltd., Zhejiang (CN)

(72) Inventors: Hancheng Zhang, Zhejiang (CN); Shifeng Liu, Zhejiang (CN); Xiangyang Ye, Zhejiang (CN)

(73) Assignee: Hangzhou Innogate Pharma Co., Ltd., Zhejiang (CN)

( * ) Notice: Subject to any disclaimer, the term of this patent is extended or adjusted under 35 U.S.C. 154(b) by 432 days.

(21) Appl. No.: 16/304,826

(22) PCT Filed: May 27, 2017

(86) PCT No.: PCT/CN2017/086445
§ 371 (c)(1),
(2) Date: Mar. 17, 2020

(87) PCT Pub. No.: WO2017/202390
PCT Pub. Date: Nov. 30, 2017

(65) Prior Publication Data
US 2020/0199120 A1    Jun. 25, 2020

(30) Foreign Application Priority Data

May 27, 2016    (CN) .......................... 201610364948.4

(51) Int. Cl.
*C07D 471/04*       (2006.01)
*A61P 35/00*        (2006.01)
*C07D 519/00*       (2006.01)

(52) U.S. Cl.
CPC ............ *C07D 471/04* (2013.01); *A61P 35/00* (2018.01); *C07D 519/00* (2013.01)

(58) Field of Classification Search
CPC ...... C07D 471/04; C07D 519/00; A61P 35/00
USPC .................................................. 514/210.21
See application file for complete search history.

(56) References Cited

U.S. PATENT DOCUMENTS 9,266,883 B2 *   2/2016  Buschmann ........... A61K 31/55
2019/0276451 A1   9/2019  Gao et al.

FOREIGN PATENT DOCUMENTS

CN    109071532 A       12/2018
CN    109745321    *    5/2019
WO    2015/059668 A1    4/2015

OTHER PUBLICATIONS

Weiss et al., Molecular Cancer Therapeutics (2019), 18(12), 2194-2206.*
Knoepfel et al., ACS Medicinal Chemistry Letters (2018), 9(3), 215-220.*
Int'l Search Report dated Jul. 19, 2017 in Int'l Application No. PCT/CN2017/086445.

* cited by examiner

Primary Examiner — Niloofar Rahmani
(74) Attorney, Agent, or Firm — Ice Miller LLP

(57) ABSTRACT

A heterocyclic compound which is an inhibitor of FGFR4 (fibroblast growth factor receptor 4) is described. Specifically, a compound represented by the following formula (I), including an isomer (enantiomer or diastereomer) which may be present, or a pharmaceutically acceptable salt thereof, prodrugs, deuterated derivatives, hydrates, solvates, are described. The definition of each group in the formula (I) is as described in the specification. The compounds have FGFR4 inhibitory activity and can be used for the prevention or treatment of diseases associated with FGFR4 activity or expression, and can also be used in combination with other drugs for the treatment of various related diseases, as described.

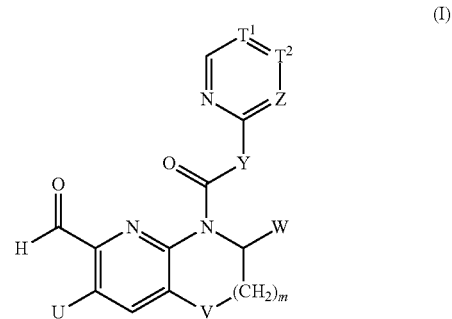

14 Claims, No Drawings

HETEROCYCLIC COMPOUND SERVING AS FGFR4 INHIBITOR

CROSS-REFERENCE TO RELATED APPLICATIONS

This application is a Section 371 of International Application No. PCT/CN2017/086445, filed May 27, 2017, which was published in the Chinese language on Nov. 30, 2017, under International Publication No. WO 2017/202390 A1, which claims priority under 35 U.S.C. § 119(b) to Chinese Application No. 201610364948.4, filed May 27, 2016, the disclosures of all of which are incorporated herein by reference in their entireties.

TECHNICAL FIELD

The present invention provides a novel class of heterocyclic compounds, their synthesis and their use as FGFR4 inhibitors.

BACKGROUND

FGFR (fibroblast growth factor receptor) is a receptor tyrosine protein kinase with four subtypes FGFR1, FGFR2, FGFR3 and FGFR4, which are key in maintaining cell growth, proliferation, apoptosis and migration. FGFR activating mutation not only promotes the proliferation and inhibition of apoptosis of malignant tumor cells, but also plays an important role in tumor angiogenesis, tumor invasion and metastasis. FGFR is highly expressed in non-small cell lung cancer, liver cancer, breast cancer, bladder cancer and many other cancers. Therefore, small molecule FGFR kinase inhibitor is a promising treatment for cancer patients with abnormal FGFR expression. The development of selective small molecule FGFR inhibitors has received increasing attention.

Liver cancer is one of the most malignant tumors with the highest morbidity and mortality. There are 466,000 new cases of liver cancer and 422,000 cases of liver cancer deaths in China every year. Studies have shown that the FGFR4-FGF19 signaling pathway is closely related to hepatocellular carcinoma (HCCs), while FGFR4 is the subtype highly expressed in human hepatocytes, with a variety of FGFR4 variants found in liver cancer patients. Selective inhibition of FGFR4 without inhibiting other subtypes FGFR1, FGFR2, and FGFR3 may avoid certain toxicity and may be an important therapeutic target for the treatment of liver cancer. Clinical studies have shown that FGFR inhibitors can be used in the treatment of a variety of cancers, but there is an urgent need to develop selective FGFR4 inhibitors for the treatment of a variety of tumors, especially for the treatment of liver cancer.

SUMMARY OF THE INVENTION

The present invention is to provide a novel class of FGFR4 inhibitors of structural design, as well as methods for their preparation and use.

The first aspect of the invention is to provide a compound of formula (I), or its pharmaceutically acceptable salt, prodrug, deuterated derivative, hydrate, or solvate thereof:

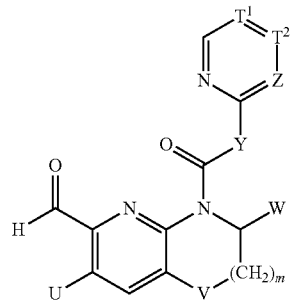

wherein:

$T^1$ is N or $CR^1$, wherein $R^1$ is selected from the group consisting of hydrogen, halogen, $C_{1-6}$ alkyl, $C_{3-6}$ cycloalkyl, cyano, $CO_2NH_2$, halogenated $C_{1-4}$ alkyl or hydroxy substituted $C_{1-4}$ alkyl;

$T^2$ is N or $CR^2$, wherein $R^2$ is selected from the group consisting of hydrogen, halogen, $C_{1-4}$ alkyl, $C_{1-4}$ alkoxy, hydroxy substituted $C_{1-4}$ alkoxy, $C_{2-4}$ alkenyl, $C_{2-4}$ alkyl, $CHR^3R^4$, cyano, $CO_2NH_2$, $C_{1-4}$ alkoxy substituted $C_{1-4}$ alkyl, $C_{1-4}$ alkoxy substituted $C_{1-4}$ alkoxy, $C_{1-4}$ alkoxy substituted halogen $C_{1-4}$ alkoxy, $C_{1-4}$ alkoxy substituted $C_{2-4}$ alkenyl, $C_{1-4}$ alkoxy substituted $C_{2-4}$ alkynyl, $C_{1-4}$ alkylthiol, bis($C_{1-4}$ alkyl)amino substituted $C_{1-4}$ alkoxy, $O(CR^7R^8)_n$—$R^6$, $NR^5(CR^7R^8)_n$—$R^6$, or halogenated $C_{1-4}$ alkoxy (preferably, the halogenated $C_{1-4}$ alkoxy is optionally substituted by hydroxy);

$R^3$ and $R^4$ together with the carbon atom to which they are attached forms a 4- to 7-membered heterocyclic group containing one or two heteroatoms selected from N, O or S, wherein the heterocyclic group is optionally substituted by one or two $X^1$; each $X^1$ is independently selected from the group consisting of halogen, $C_{1-4}$ alkyl, hydroxy, $C_{3-8}$ cycloalkyl, 4- to 8-membered heterocyclic, $C_{1-4}$ alkoxy, $C_{1-4}$ alkoxy substituted $C_{1-4}$ alkoxy, $C(O)C_{1-4}$ alkyl, cyano, $CO_2NH_2$, amino, $C_{1-4}$ alkylamino, bis($C_{1-4}$ alkyl)amino, or =O;

$R^5$ is hydrogen or $C_{1-4}$ alkyl;

$R^6$ is $C_{1-4}$ alkyl, hydroxy substituted $C_{1-4}$ alkyl, $C_{2-4}$ alkenyl, $C_{2-4}$ alkynyl, $C_{2-4}$ alkynyl substituted $C_{1-4}$ alkyl, $C_{3-12}$ cycloalkyl (including monocyclic, bridged, spiro, and cyclo), $C_{3-8}$ cycloalkyl substituted $C_{1-4}$ alkyl, 4- to 12-membered heterocyclic group having 1 to 3 heteroatoms selected from N, O and S (including monocyclic, bridged, spiro, and fused ring), 4- to 12-membered heterocyclic substituted $C_{1-4}$ alkyl, 6-membered aryl, 6-membered aryl substituted $C_{1-4}$ alkyl, 5- to 6-membered heteroaryl, 5- to 6-membered heteroaryl substituted $C_{1-4}$ alkyl, halogenated $C_{1-4}$ alkyl, $C_{1-4}$ alkoxy substituted $C_{1-4}$ alkyl, halogenated $C_{1-4}$ alkoxy substituted $C_{1-4}$ alkyl, bis ($C_{1-4}$ alkyl) amino substituted $C_{1-4}$ alkyl, wherein the alkyl, alkenyl, alkynyl, cycloalkyl, heterocyclic group, aryl, and heteroaryl are optionally substituted with from 1 to 3 $X^2$; each $X^2$ are independently selected from the group consisting of hydrogen, halogen, $C_{1-4}$ alkyl, hydroxy, $C_{1-4}$ alkoxy, $C_{3-8}$ cycloalkyl, 4- to 8-membered heterocyclic group, $C_{1-4}$ alkoxy substituted $C_{1-4}$ alkyl, $C_{1-4}$ alkoxy substituted $C_{1-4}$ alkoxy, $C(O)C_{1-4}$ alkyl, $C(O)OC_{1-4}$ alkyl, $OC(O)C_{1-4}$ alkyl, amino, $C_{1-4}$ alkylamino, bis ($C_{1-4}$ alkyl) amino, or =O;

or $R^5$ and $R^6$ together with the nitrogen atom to which they are attached form a 4- to 12-membered heterocyclic group which may contain one or two additional heteroatoms selected from N, O or S, wherein the heterocyclic group is optionally substituted by one or more $X^3$; each $X^3$ is independently selected from the group consisting of hydrogen, halogen, $C_{1-4}$ alkyl, hydroxy, $C_{1-4}$ alkoxy, $C_{3-8}$ cycloalkyl, 4- to 8-membered heterocyclic, $C_{1-4}$ alkyoxy substituted $C_{1-4}$ alkoxy, $C(O)C_{1-4}$ alkyl, amino, $C_{1-4}$ alkylamino, bis ($C_{1-4}$ alkyl) amino, bis ($C_{1-4}$ alkyl) amino substituted $C_{1-4}$ alkyl, or =O;

$R^7$ and $R^8$ are each independently hydrogen, $C_{1-4}$ alkyl or halogen;

Z is CH or N; wherein, when $T^1$ is N, then $T^2$ and Z are other than N; when $T^2$ is N, then $T^1$ and Z are other than N; when Z is N, then $T^1$ and $T^2$ are other than N;

Y is NR or O; wherein R is hydrogen or $C_{1-4}$ alkyl;

W is hydrogen or $C_{1-4}$ alkyl;

V is $CH_2$, O, CH(OH), CHF, or $CF_2$;

U is hydrogen, halogen, $C_{1-4}$ alkyl, halogenated $C_{1-4}$ alkyl, hydroxy substituted $C_{1-4}$ alkyl, $C_{1-4}$ alkoxy substituted $C_{1-4}$ alkyl, $C_{1-4}$ alkoxy, $C_{2-4}$ alkenyl, $C_{2-4}$ alkynyl, $(CR^9R^{10})_p$—$NR^{11}R^{12}$, $(CR^{13}R^{14})^q$—$R^{15}$, $CH_2CO_2H$, or C(O)H;

$R^9$ and $R^{10}$ are each independently hydrogen or $C_{1-4}$ alkyl;

$R^{11}$ is $C_{1-4}$ alkyl, bis ($C_{1-4}$ alkyl) amino-substituted $C_{1-4}$ alkyl, or 4- to 7-membered heterocyclic group containing 1-2 hetero atoms selected from N, O and S;

$R^{12}$ is $C_{1-4}$ alkyl, halogenated $C_{1-4}$ alkyl, hydroxy substituted halogenated $C_{1-4}$ alkyl, $C(O)C_{1-4}$ alkyl, C(O)—$CH_2$—OH, C(O)—$CH_2$—$OCH_3$, C(O)—$CH_2$—$N(CH_3)_2$, $S(O)_2$$CH_3$ or $C(O)C(O)N(R^{16})_2$;

or $R^{11}$ and $R^{12}$ together with the N atom to which they are attached forms monocyclic, bicyclic, or polycyclic 4- to 12-membered ring structure which may contain, in addition to the existing N atom, additional 1-2 heteroatoms selected from N, O, S; meanwhile, the cyclic structure may be optionally substituted by 1-3 $X^4$, and the substituted sites are on the C and N atoms, provided that the resulting structure is a reasonably stable structure; $X^4$ is each independently selected from the group consisting of halogen, $C_{1-4}$ alkyl, $C_{3-8}$ cycloalkyl, 4- to 6-membered heterocyclic group, $C_{1-4}$ alkyl substituted 4- to 6-membered heterocyclic group, 6-membered aryl, 5- to 6-membered heteroaryl, hydroxy, $C_{1-4}$ alkoxy, halogenated $C_{1-4}$ alkyl, hydroxy-substituted $C_{1-4}$ alkyl, $C_{1-4}$ alkoxy substituted $C_{1-4}$ alkyl, $C(O)C_{1-4}$ alkyl, $C(O)CH_2OH$, $C(O)OC_{1-4}$ alkyl, $OC(O)C_{1-4}$ alkyl, amino, $C_{1-4}$ alkylamino, bis($C_{1-4}$ alkyl)amino, bis($C_{1-4}$ alkyl)amino substituted $C_{1-4}$ alkyl, or =O;

$R^{13}$ and $R^{14}$ are each independently hydrogen, $C_{1-4}$ alkyl or halogen;

$R^{15}$ is $C_{3-8}$ cycloalkyl, 4- to 12-membered heterocyclic group containing 1-3 hetero atoms selected from N, O and S, 6-membered aryl, or 5- to 6-membered heteroaryl group comprising 1-3 hetero atom selected from N, O and S, wherein the cycloalkyl, heterocyclic group, aryl, or heteroaryl is optionally substituted by 1-3 $X^4$, while the $X^4$ is as defined above;

$R^{16}$ is each independently hydrogen or $C_{1-4}$ alkyl;

m is 0, 1, 2 or 3;

n is 0, 1, 2, or 3;

p is 0, 1, or 2;

q is 0, 1, or 2.

In another preferred embodiment, $T^1$ is $CR^1$; and/or $T^2$ is $CR^2$; and/or Z is CH; and/or Y is NH; and/or W is hydrogen; and/or V is $CH_2$; and/or m is 1; and/or U is $C_{1-4}$ alkyl, halogenated $C_{1-4}$ alkyl, hydroxy substituted $C_{1-4}$ alkyl, $C_{1-4}$ alkoxy substituted $C_{1-4}$ alkyl, $C_{1-4}$ alkoxy, $C_{2-4}$ alkenyl, $C_{2-4}$ alkynyl, $CH_2$—$NR^{11}R^{12}$, $(CR^{13}R^{14})^q$—$R^{15}$, $CH_2CO_2H$, or C(O)H;

wherein $R^1$, $R^2$, $R^{11}$, $R^{12}$, $R^{13}$, $R^{14}$, $R^{15}$ and q are respectively as described above.

In another preferred embodiment, $R^1$ is CN.

In another preferred embodiment, $R^2$ is $NR^5(CR^7R^8)_n$—$R^6$ or $O(CR^7R^8)_n$—$R^6$; wherein $R^5$ is hydrogen or $C_{1-4}$ alkyl; $R^6$ is $C_{2-4}$ alkenyl, $C_{2-4}$ alkynyl, $C_{2-4}$ alkynyl substituted $C_{1-4}$ alkyl, $C_{3-12}$ cycloalkyl (including monocyclic, bridged, spiro, and fused ring), $C_{3-8}$ cycloalkyl substituted $C_{1-4}$ alkyl, 4- to 12-membered heterocyclic group containing 1 to 3 hetero atoms selected from N, O and S (including monocyclic, bridged, spiro, and fused ring), 4- to 12-membered heterocyclic substituted $C_{1-4}$ alkyl, 6-membered aryl, 6-membered aryl substituted $C_{1-4}$ alkyl, 5- to 6-membered heteroaryl, or 5- to 6-membered heteroaryl substituted $C_{1-4}$ alkyl group; wherein the alkyl, alkenyl, alkynyl, cycloalkyl, heterocyclic group, aryl, or heteroaryl are optionally substituted by 1-3 $X^2$, and $X^2$ is as described above; or $R^5$ and $R^6$ together with the nitrogen atom to which they are attached form 4- to 5-membered heterocyclic group or 7- to 12-membered heterocyclic group comprising additional 1-2 hetero atoms selected from N, O or S, wherein the heterocyclic group is optionally substituted by 1-2 $X^3$, and $X^3$ is as defined above, wherein n, $R^7$ and $R^8$ are as defined above.

In another preferred embodiment, $R^2$ is $NH(CR^7R^8)_n$—$R^6$ or $O(CR^7R^8)_n$—$R^6$; $R^6$ is $C_{2-4}$ alkenyl, $C_{2-4}$ alkynyl $C_{2-4}$ alkynyl substituted $C_{1-4}$ alkyl, $C_{3-12}$ cycloalkyl (including monocyclic, bridged, spiro, or fused ring), $C_{3-8}$ cycloalkyl substituted $C_{1-4}$ alkyl, 4- to 12-membered heterocyclic group comprising 1 to 3 hetero atoms selected from N, O and S (including monocyclic, bridged, spiro, and fused ring), and 4- to 12-membered heterocyclic group substituted $C_{1-4}$ alkyl, 6-membered aryl, 6-membered aryl substituted $C_{1-4}$ alkyl, 5- to 6-membered heteroaryl, or 5- to 6-membered heteroaryl substituted $C_{1-4}$ alkyl, wherein alkyl, alkenyl, alkynyl, cycloalkyl, heterocyclic group, aryl, or heteroaryl is optionally substituted by 1-3 $X^2$, while $X^2$ is as defined above; wherein n, $R^7$ and $R^8$ are as defined above.

In another preferred embodiment, $R^2$ is $NHR^6$ or $OR^6$; $R^6$ is $C_{2-4}$ alkynyl substituted $C_{1-4}$ alkyl, $C_{3-12}$ cycloalkyl (including monocyclic, bridged, spiro, and fused ring), $C_{3-8}$ cycloalkyl substituted $C_{1-4}$ alkyl, 4- to 12-membered heterocyclic ring containing 1-3 heteroatoms selected from N, O and S (including monocyclic, bridged, spiro, and fused ring), 4- to 12-membered heterocyclic group substituted $C_{1-4}$ alkyl group, wherein the alkyl group, alkynyl group, cycloalkyl group, heterocyclic group are optionally substituted by 1-3 $X^2$, and $X^2$ is as defined above.

In another preferred embodiment, $R^2$ is $NHR^6$ or $OR^6$; $R^6$ is $C_{3-8}$ cycloalkyl group, 3- to 8-membered heterocycloalkyl comprising 1-3 heteroatoms selected from N, O and S, $C_{1-4}$ alkoxy substituted $C_{3-8}$ cycloalkyl, hydroxy substituted $C_{3-8}$ cycloalkyl, $C_{1-4}$ alkoxy substituted $C_{1-4}$ alkyl, $C_{3-8}$ cycloalkyl-substituted $C_{1-4}$ alkyl, 3- to 8-membered heterocycloalkyl substituted $C_{1-4}$ alkyl, hydroxyl group-containing $C_{3-8}$ cycloalkyl substituted $C_{1-4}$ alkyl, wherein alkyl, cycloalkyl, heterocyclic group is optionally substituted by 1-3 $X^2$, and $X^2$ is as defined above.

In another preferred embodiment, $R^2$ is $NHR^6$; $R^6$ is $C_{3-8}$ cycloalkyl group, $C_{3-8}$ heterocycloalkyl comprising 1-3 heteroatoms selected from N, O and S, $C_{1-4}$ alkoxy substituted $C_{3-8}$ cycloalkyl, hydroxy substituted $C_{3-8}$ cycloalkyl, $C_{1-4}$ alkoxy substituted $C_{1-4}$ alkyl, $C_{1-4}$ cycloalkyl-substituted $C_{1-4}$ alkyl, or hydroxyl group-containing $C_{3-8}$ cycloalkyl substituted $C_{1-4}$ alkyl.

In another preferred embodiment, $R^2$ is $OR^6$; $R^6$ is $C_{3-8}$ cycloalkyl group, $C_{1-4}$ alkoxy substituted $C_{3-8}$ cycloalkyl, hydroxy substituted $C_{3-8}$ cycloalkyl, $C_{1-4}$ alkoxy substituted $C_{1-4}$ alkyl, $C_{1-4}$ cycloalkyl-substituted $C_{1-4}$ alkyl.

In another preferred embodiment, the compound is of the structure of formula (II),

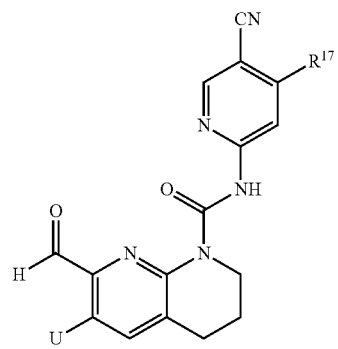

wherein $R^{17}$ is a group selected from the group consisting of

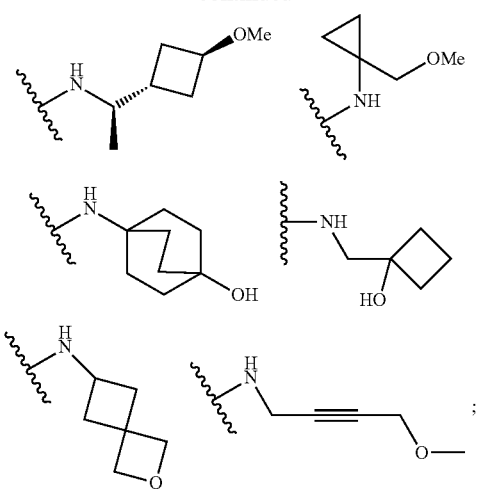

or $R^{17}$ is a group selected from the group consisting of

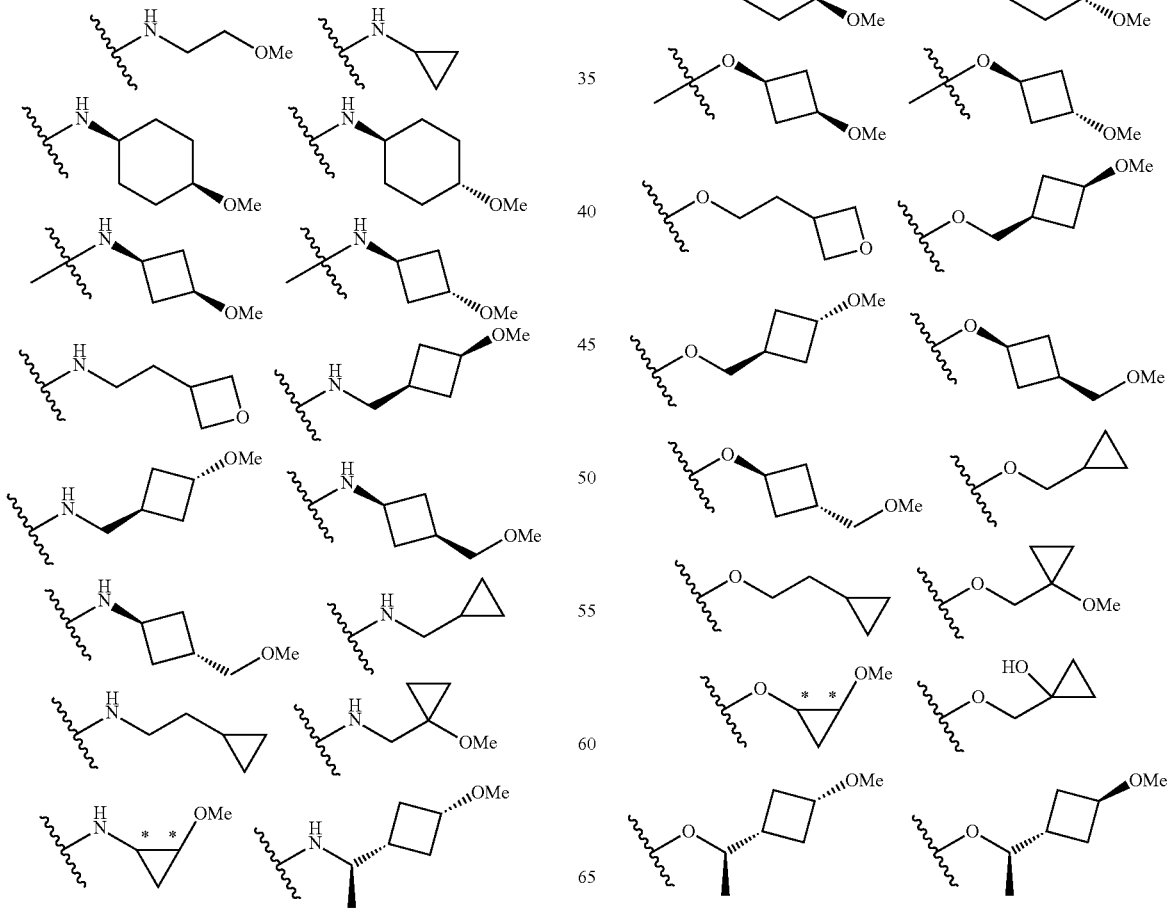

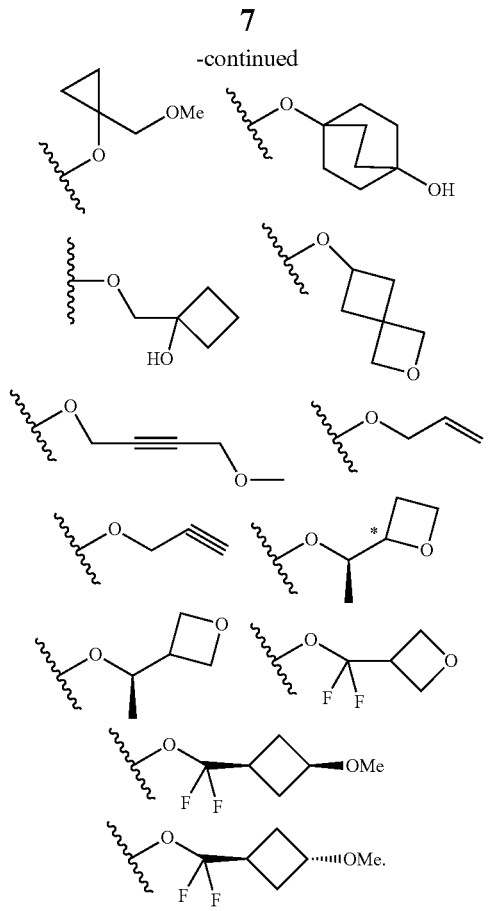

In another preferred embodiment, the compound is of the structure of formula (II),

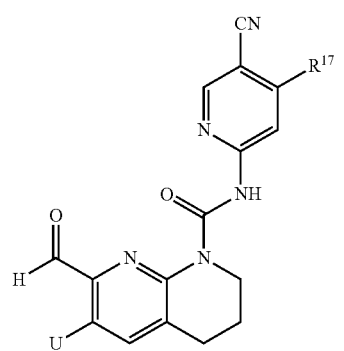

wherein $R^{17}$ is a group selected from the group consisting of

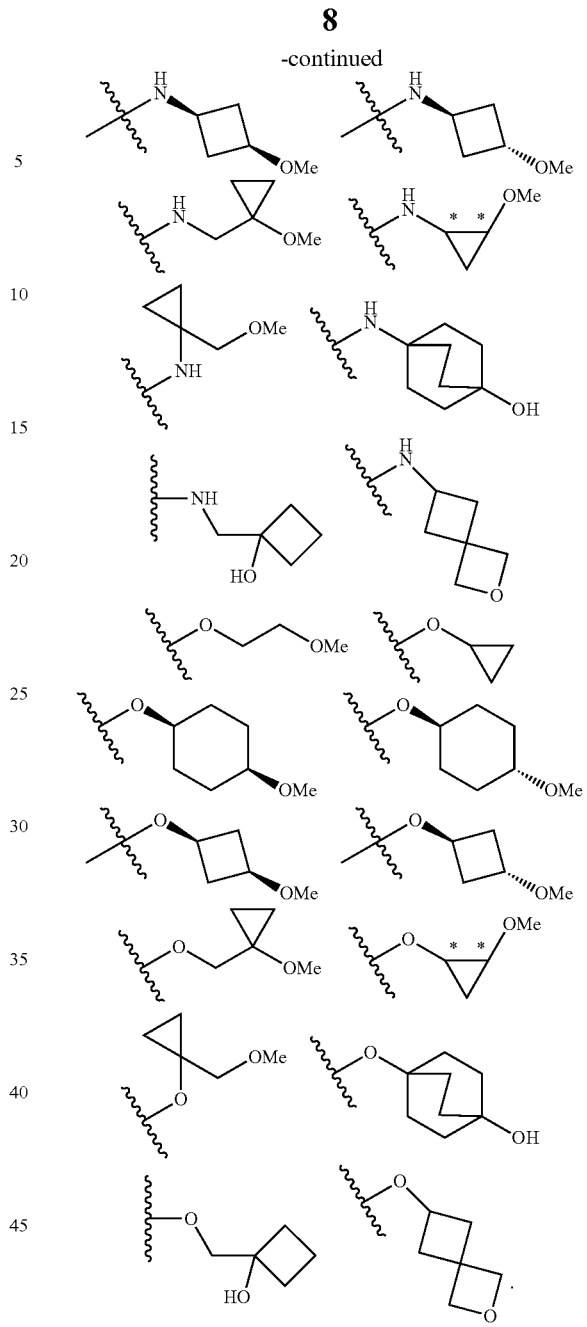

In another preferred embodiment, U is $CH_2-NR^{11}R^{12}$; wherein $R^{11}$ is $C_{1-4}$ alkyl, 4- to 6-membered heterocyclic group, or bis ($C_{1-4}$ alkyl) amino-substituted $C_{1-4}$ alkyl; $R^{12}$ is $C_{1-4}$ alkyl, halo $C_{1-4}$ alkyl, hydroxyhalogenated $C_{1-4}$ alkyl, $C(O)C_{1-4}$ alkyl, $C(O)-CH_2-OH$, $C(O)-CH_2-OCH_3$, $C(O)-CH_2-N(CH_3)_2$, $S(O)_2CH_3$, or $C(O)C(O)N(R^{16})_2$; $R^{11}$ and $R^{12}$ together with the N atom to which they are attached form monocyclic, bicyclic, or polycyclic 5- to 12-membered cyclic structure which may contain, in addition to the existing N atom, additional 1-2 heteroatoms selected from N, O or S; and the cyclic structure may be optionally substituted with 1-3 $X^4$, and the substituted sites are on the C and N atoms, provided that the structure formed is a reasonably stable structure; or U is $(CR^{13}R^{14})_{0-2}-R^{15}$; wherein $R^{13}$ and $R^{14}$ are each independently hydrogen or $C_{1-4}$ alkyl; $R^{15}$ is $C_{3-8}$ cycloalkyl, 4- to 12-membered heterocyclic group, 6-membered aryl, or 5- to 6-membered heteroaryl, wherein the cycloalkyl, heterocyclic group, aryl, or heteroaryl is optionally substituted by 1 to 3 $X^4$, and $X^4$ is as defined above.

In another preferred embodiment, U is $CH_2$—$NR^{11}R^{12}$; wherein $R^{11}$ and $R^{12}$ together with the N atom to which they are attached to form bicyclic or polycyclic 8- to 12-membered cyclic structure which may contain, in addition to the existing N atom, 1-2 additional hetero atoms selected from N, O, and S; further, the cyclic structure may optionally substituted by 1-3 $X^4$, and the substituted sites are on the C and N atoms, provided that the structure formed is a reasonably stable structure;

In another preferred embodiment, U is $CH_2$—$R^{15}$; wherein $R^{15}$ is $C_{3-8}$ cycloalkyl, 4- to 12-membered heterocyclic group containing 1-3 hetero atoms selected from N, O and S, 6-membered aryl, or 5- to 6-membered heteroaryl, wherein the cycloalkyl, heterocyclic group, aryl, or heteroaryl is optionally substituted by 1-3 $X^4$, while the $X^4$ is as defined above.

In another preferred embodiment, U is $CH_2$—$R^{15}$; wherein $R^{15}$ is 4- to 12-membered heterocyclic group containing 1-3 hetero atoms selected from N, O and S, wherein the heterocyclic group is optionally substituted by 1-3 $X^4$, while the $X^4$ is as defined above.

In another preferred embodiment, U is $CH_2$—$R^{15}$; wherein $R^{15}$ is 5- to 9-membered heterocyclic group containing 1 to 3 hetero atoms optionally selected from N, O and S, wherein the heterocyclic group is optionally substituted by 1 to 3 $X^4$, and $X^4$ is as defined above.

In another preferred embodiment, $X^4$ is =O, $C_{1-4}$ alkyl, $C_{3-8}$ cycloalkyl, $C_{1-4}$ alkyl substituted $C_{3-8}$ cycloalkyl, 4- to 6-membered heterocyclic group, $C_{1-4}$ alkyl substituted 4- to 6-membered heterocyclic group.

In another preferred embodiment, $R^{15}$ is 5- to 9-membered heterocyclic group comprising 2 heteroatoms selected from N, O or S; preferably, $R^{15}$ is 5- to 9-membered heterocyclic group comprising two N heteroatoms.

In another preferred embodiment, the U is a group selected from the group consisting

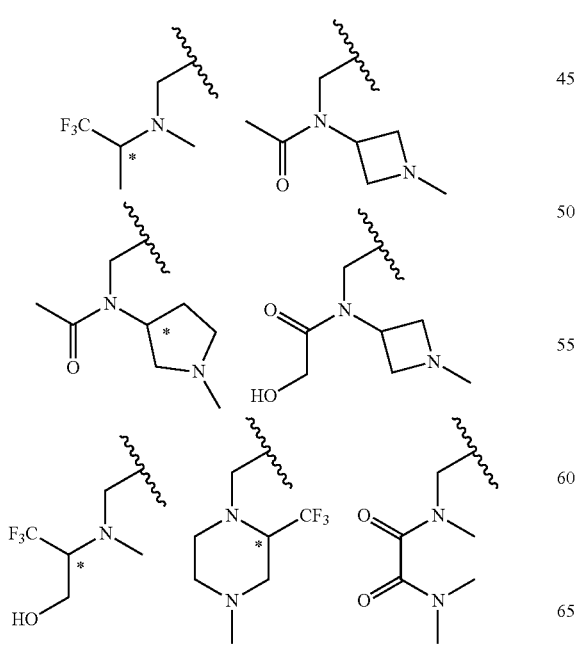

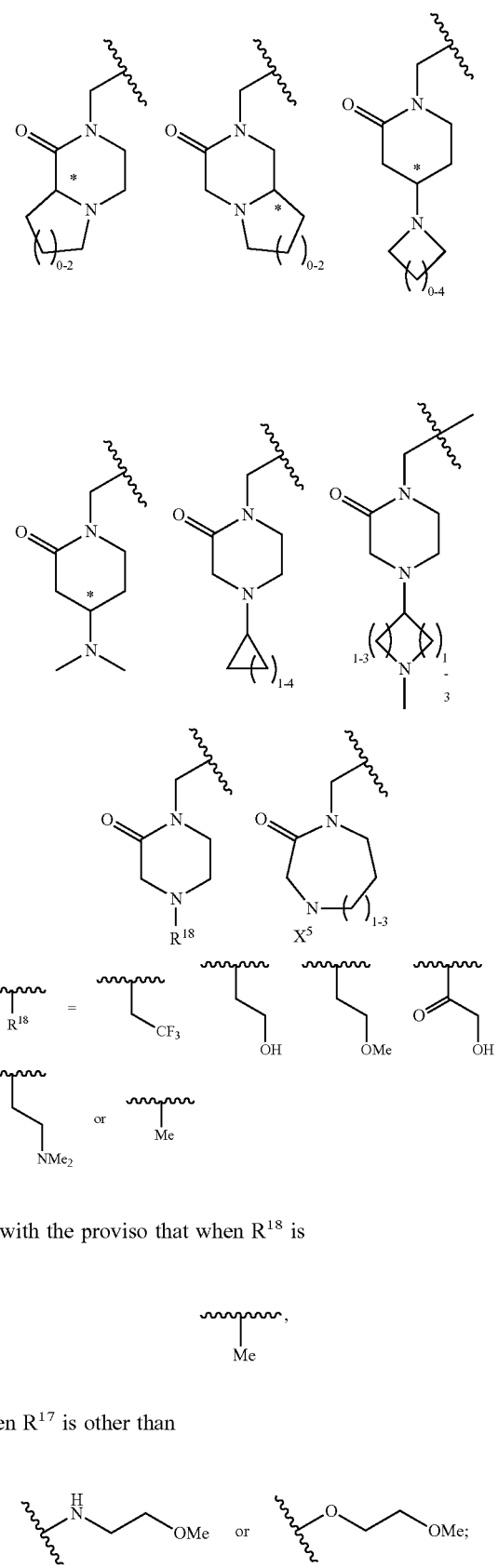

with the proviso that when $R^{18}$ is then $R^{17}$ is other than when R[17] is
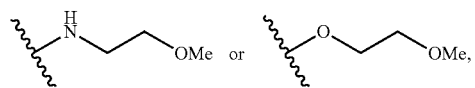 [SMILES: *NCCOC ; *OCCOC]
then R[18] is other than
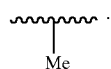
In another preferred embodiment, the U is a group selected from the group consisting of
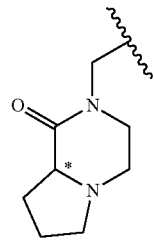 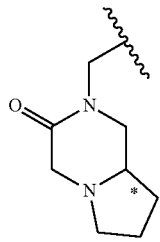 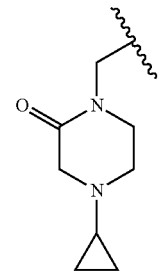
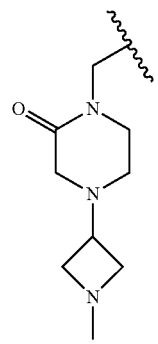 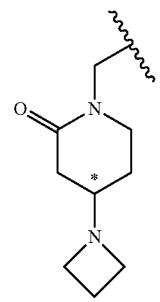 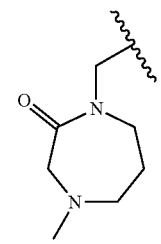
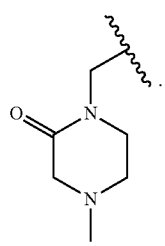
In another preferred embodiment, the compound is selected from the group consisting of
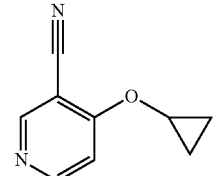
1
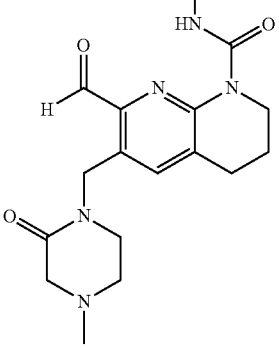
2
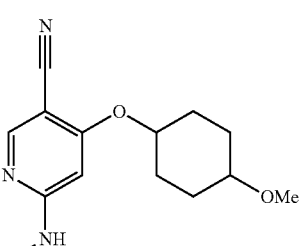
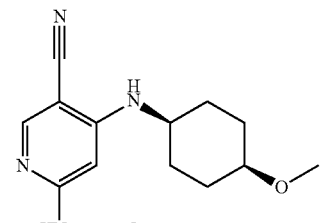
3
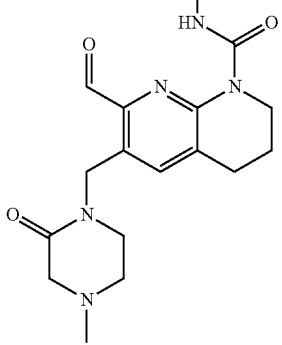

-continued
4
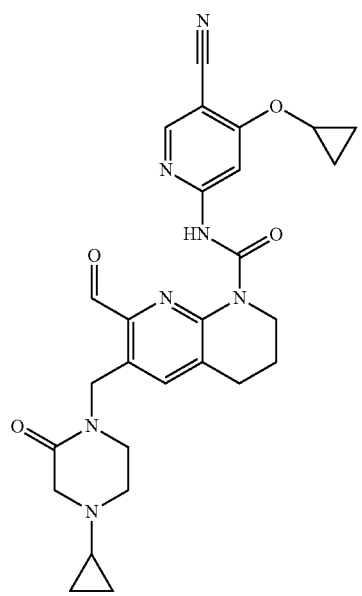
5
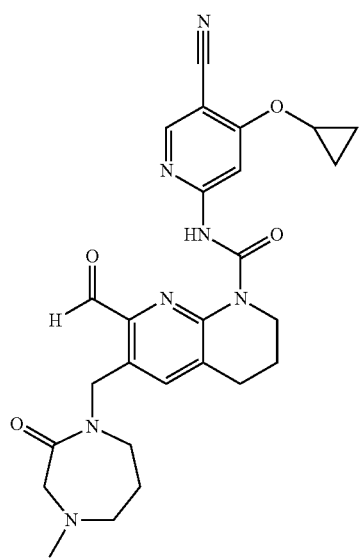
-continued
5
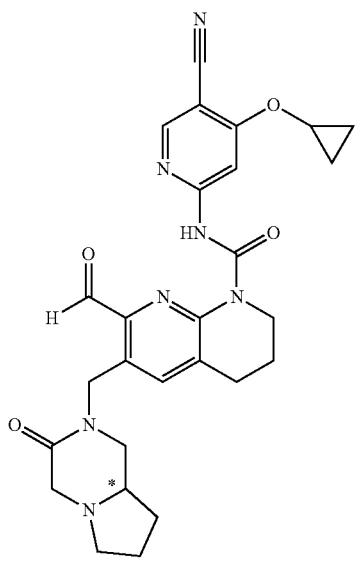
6
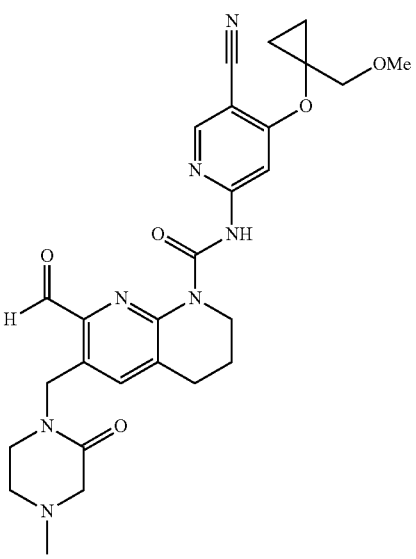
7
8
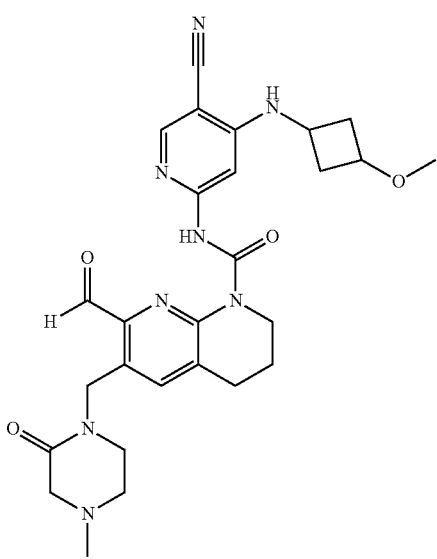

9
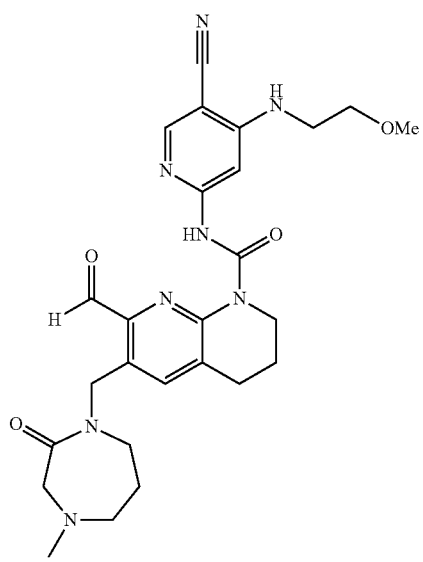
10
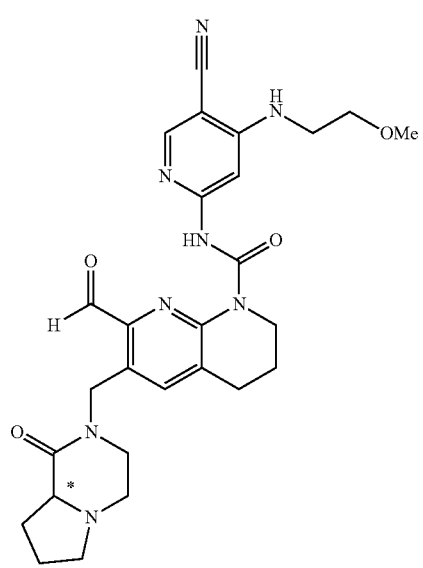
11
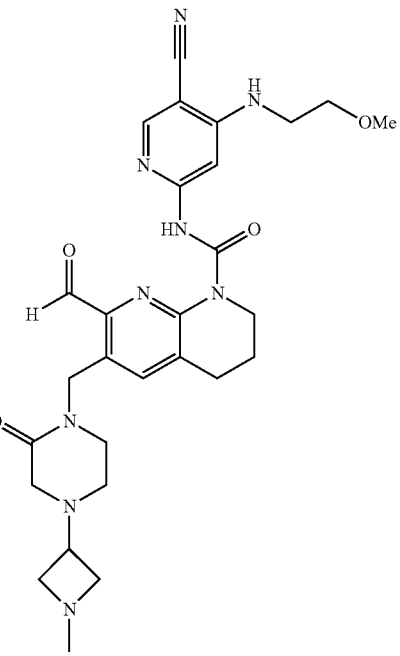
12
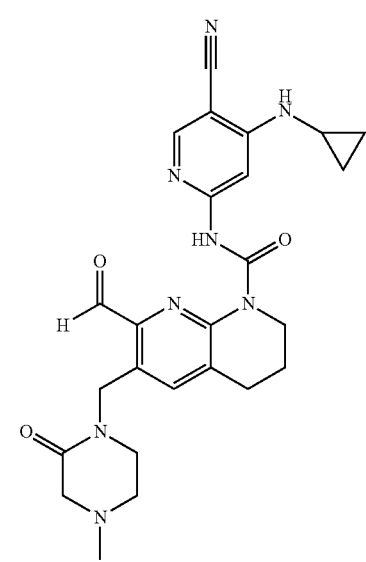

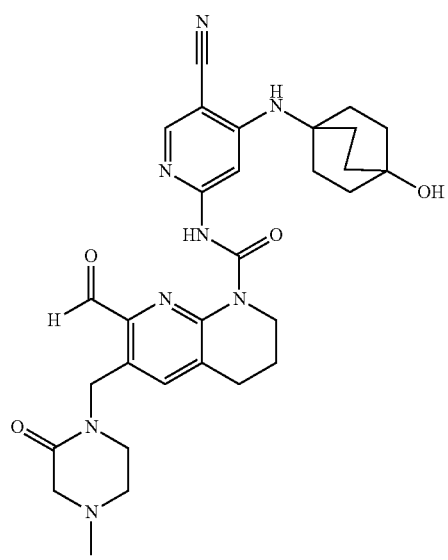
13
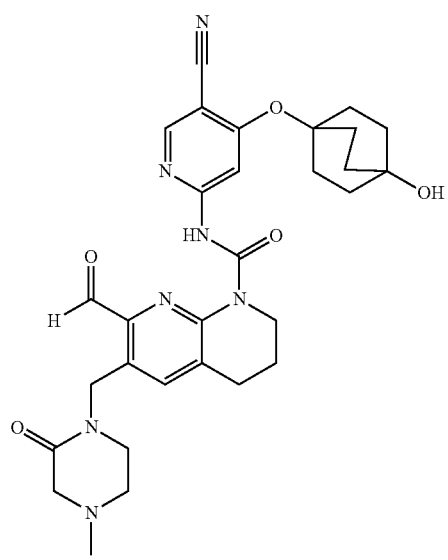
14
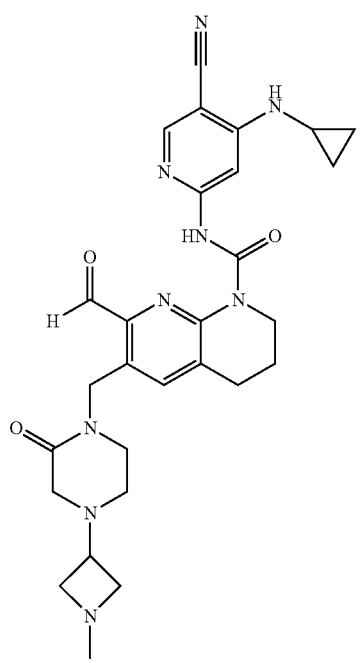
15
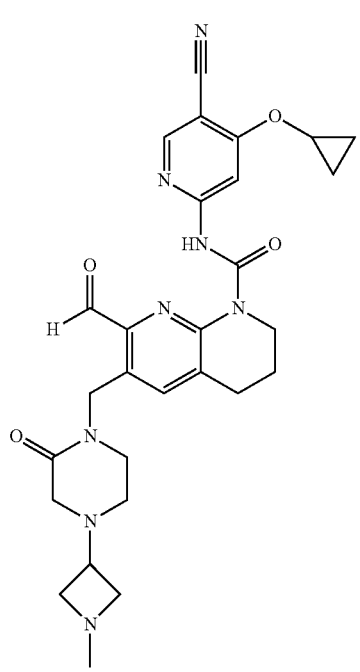
16

17
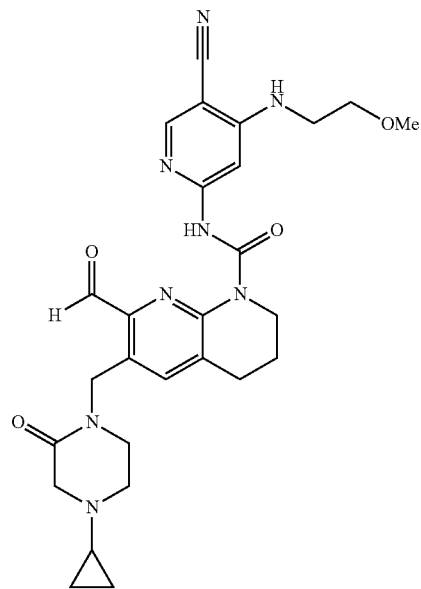
18
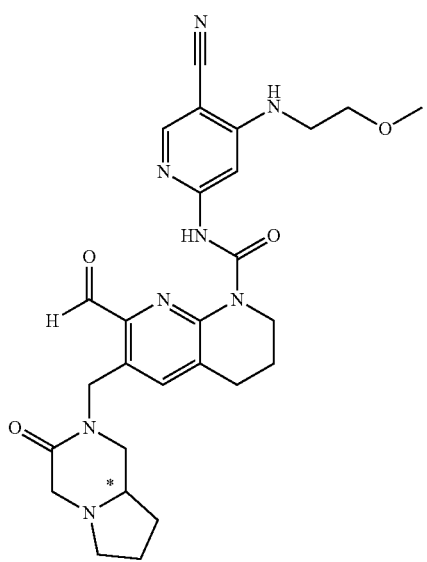
19
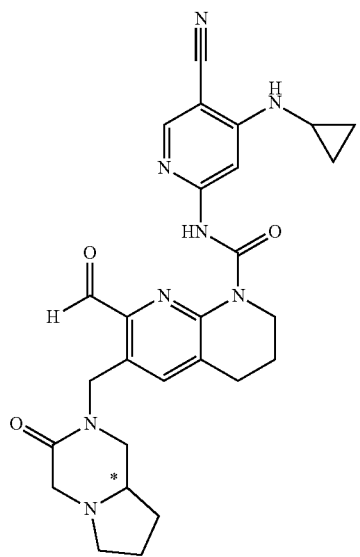
20
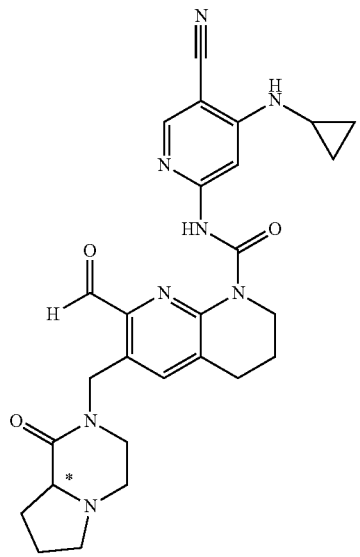
21
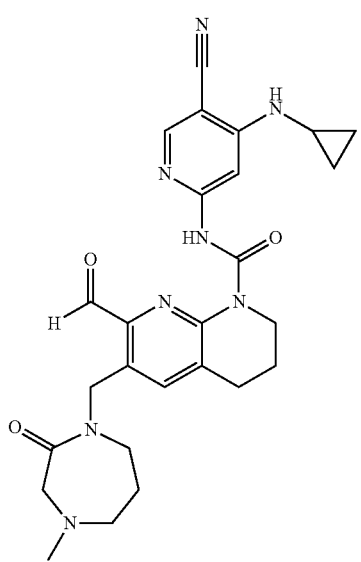

-continued

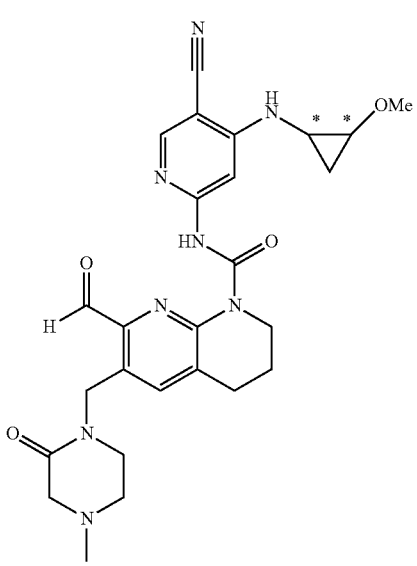

wherein,
"*" indicates a chiral center.

According to a second aspect of the invention, there is provided a use of a compound of formula (I) according to the first aspect of the invention, for:

(a) Preparing a medicament for treating a disease associated with FGFR4 activity or expression; and/or (b) Preparing a FGFR4 targeting inhibitor; and/or (c) Non-therapeutic inhibition of FGFR4 activity in vitro.

In another preferred embodiment, the disease is a tumor.

In another preferred embodiment, the tumor is selected from the group consisting of lung cancer, bladder cancer, breast cancer, gastric cancer, liver cancer, salivary gland sarcoma, ovarian cancer, prostate cancer, cervical cancer, epithelial cell carcinoma, multiple myeloma, pancreatic cancer, lymphoma, chronic myelogenous leukemia, lymphocytic leukemia, cutaneous T-cell lymphoma, etc.

In a third aspect of the invention, there is provided a pharmaceutical composition comprising: (i) an effective amount of a compound of formula (I), or a pharmaceutically acceptable salt thereof; and (ii) pharmaceutically acceptable carrier.

The fourth aspect of the invention is to provide a method of inhibiting FGFR4 activity, the method comprising the steps of: administering an inhibitory effective amount of a compound of formula (I), or a pharmaceutically acceptable salt thereof, according to the first aspect of the invention, or administering an inhibitory effective amount of a pharmaceutical composition to a subject according to the third aspect of the invention.

In another preferred embodiment, the inhibition is selective inhibition of FGFR4.

In another preferred embodiment, the inhibition of FGFR4 activity is non-therapeutic inhibition in vitro.

According to a fifth aspect of the invention, there is provided a process for the preparation of a compound according to the first aspect of the invention, which comprises the steps of:

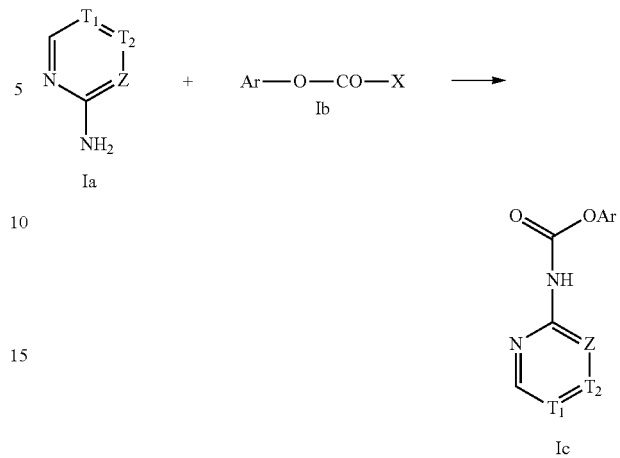

(1) In an inert solvent, compound Ia reacts with Ib in the present of a base, to form compound Ic;

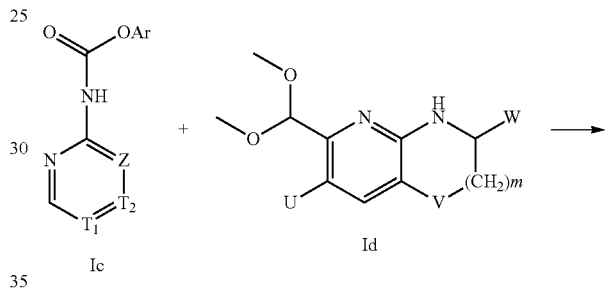

(2) In an inert solvent, compound Ic reacts with Id to form compound Ie;

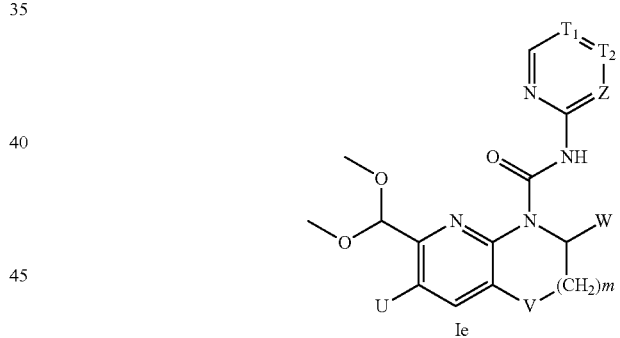

deprotection under acidic condition

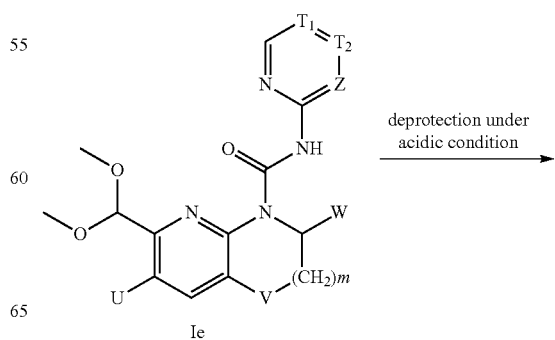

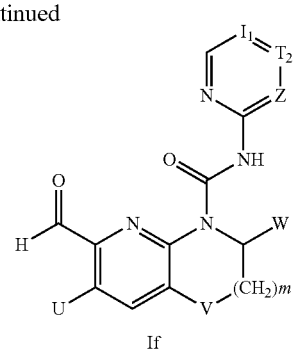

(3) In an inert solvent, compound Ie was deprotected in the present of acid, to form the target molecule If;

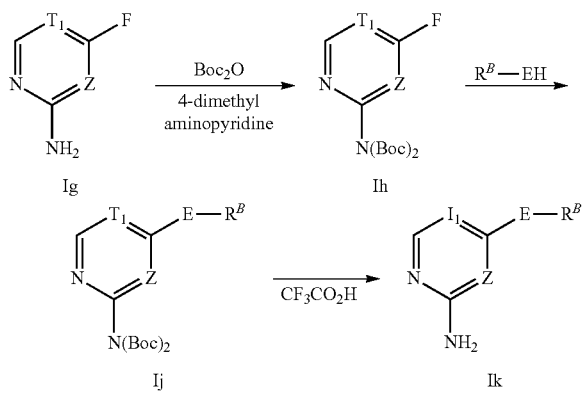

(4) To prepare the intermediate Ik (an analog of Ia), we first protected the amino group of Ig to Ih, and then reacted it with the sterically hindered nucleophile $R^B$-EH to obtain Ij, followed by deprotection under acidic condition to give Ik. The invention is particularly applicable to $R^B$-EH with high steric hindrance.

In the above formulae, Ar is an aryl group, and X is a halogen, and the other groups are as defined above.

It is to be understood that within the scope of the present invention, the various technical features of the present invention and the technical features specifically described hereinafter (as in the embodiments) may be combined with each other to constitute a new or preferred technical solution. Due to space limitations, we will not repeat them here.

DETAIL DESCRIPTION

After long-term and intensive research, the inventors unexpectedly discovered a class of heterocyclic compounds having FGFR4 (fibroblast growth factor receptor 4) inhibitory activity, and thus can be used for the preparation of pharmaceutical composition to treat a disease associated with FGFR4 activity or expression. Based on the above findings, the inventors completed the present invention.

Specifically, the present invention provides a compound represented by the formula (I) as described above, including an isomer (enantiomer or diastereomer) which may be present, or a pharmaceutically acceptable salt thereof, prodrugs, deuterated derivatives, hydrates, solvates. The compound of the present invention has FGFR4 inhibitory activity and can be used for the prevention or treatment of diseases associated with FGFR4 activity or expression, and can also be used in combination with other drugs for the treatment of various related diseases.

Terminology

Unless otherwise stated, "or" as used herein has the same meaning as "and/or" (refers to "or" and "and").

Unless otherwise specified, among all compounds of the present invention, each chiral carbon atom (chiral center) may optionally be in the R configuration or the S configuration, or a mixture of the R configuration and the S configuration.

As used herein, the term "alkyl", alone or as part of another substituent, refers to a straight (i.e., unbranched) or branched saturated hydrocarbon group containing only carbon atoms, or a combination of straight and branched chains. When the alkyl group has a carbon number modifier (e.g., $C_{1-10}$), it means that the alkyl group has 1 to 10 carbon atoms. For example, $C_{1-8}$ alkyl refers to an alkyl group containing 1 to 8 carbon atoms, including methyl, ethyl, propyl, isopropyl, butyl, isobutyl, sec-butyl, tert-butyl, or similar group.

As used herein, the term "alkenyl", when used alone or as part of another substituent, refers to a straight or branched chain, a carbon chain group having at least one carbon-carbon double bond. Alkenyl groups can be substituted or unsubstituted. When the alkenyl group has a carbon number modifier (e.g., $C_{2-8}$), it means that the alkenyl group has 2 to 8 carbon atoms. When the alkenyl group has a carbon number modifier (e.g., $C_{2-8}$), it means that the alkenyl group has 2 to 8 carbon atoms. For example, $C_{2-8}$ alkenyl refers to alkenyl groups having 2-8 carbon atoms, including ethenyl, propenyl, 1,2-butenyl, 2,3-butenyl, butadienyl, or the like.

As used herein, the term "alkynyl", when used alone or as part of another substituent, refers to an aliphatic hydrocarbon group having at least one carbon-carbon triple bond. The alkynyl group can be straight or branched, or a combination thereof. When the alkynyl group has a carbon number modifier (e.g., $C_{2-8}$ alkynyl group), it means that the alkynyl group has 2 to 8 carbon atoms. For example, the term "$C_{2-8}$ alkynyl" refers to a straight or branched alkynyl group having 2-8 carbon atoms, including ethynyl, propynyl, isopropynyl, butynyl, isobutynyl, secondary butynyl, tert-butynyl, or the like.

As used herein, when used alone or as part of another substituent, the term "cycloalkyl" refers to a unit ring having a saturated or partially saturated, bicyclic or polycyclic (fused ring, bridged or spiro) ring system. When a certain cycloalkyl group has a carbon number modifier (e.g., $C_{3-10}$), it means that the cycloalkyl group has 3 to 10 carbon atoms. In some preferred embodiments, the term "$C_{3-8}$ cycloalkyl" refers to a saturated or partially saturated monocyclic or bicyclic alkyl group having 3 to 8 carbon atoms, including cyclopropyl, cyclobutyl, cyclopentyl, cycloheptyl, or the like. "Spirocycloalkyl" refers to a bicyclic or polycyclic group that shares a carbon atom (referred to as a spiro atom) between the monocyclic rings. These may contain one or more double bonds, but none of the rings have fully conjugated π electrons system. "Fused cycloalkyl" means an all-carbon bicyclic or polycyclic group in which each ring in the system shares an adjacent pair of carbon atoms with other rings in the system, wherein one or more of the rings may contain one or more Key, but none of the rings have a fully conjugated π-electron system. "Bridge cycloalkyl" refers to an all-carbon polycyclic group in which any two rings share two carbon atoms that are not directly bonded, which may contain one or more double bonds, but none of the rings have a fully conjugated pi-electron system. The atoms contained in the cycloalkyl group are all carbon atoms. The following are some examples of cycloalkyl groups, and the present invention is not limited to the following cycloalkyl groups.

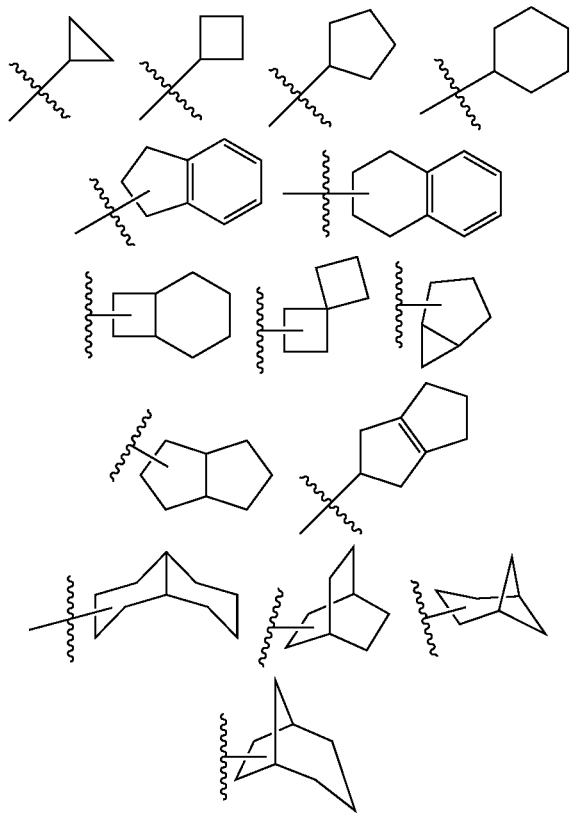

Unless stated to the contrary, the following terms used in the specification and claims have the following meanings. "Aryl" means an all-carbon monocyclic or fused polycyclic ring (i.e., a ring that shares a pair of adjacent carbon atoms) having a conjugated π-electron system, such as phenyl and naphthyl. The aryl ring may be fused to other cyclic groups (including saturated and unsaturated rings), but may not contain heteroatoms such as nitrogen, oxygen, or sulfur, while the attaching point to the parent must be in a carbon atom of a ring having conjugated π-electron system. The aryl group can be substituted or unsubstituted. The following are some examples of aryl groups, and the present invention is not limited to the aryl groups described below.

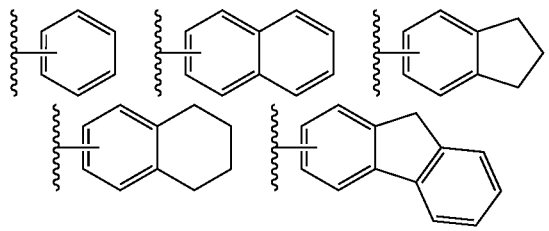

"Heteroaryl" refers to a heteroaromatic group containing one to more heteroatoms. The heteroatoms referred to herein include oxygen, sulfur, and nitrogen. Examples are, furyl, thienyl, pyridyl, pyrazolyl, pyrrolyl, N-alkylpyrrolyl, pyrimidinyl, pyrazinyl, imidazolyl, tetrazolyl, and the like. The heteroaryl ring may be fused to an aryl, heterocyclic or cycloalkyl ring wherein the ring to which the parent structure is attached is a heteroaryl ring. The heteroaryl group can be optionally substituted or unsubstituted. The following are some examples of heteroaryl groups, and the present invention is not limited to the following heteroaryl groups. Among them, the last three heteroaryl groups are tricyclic heteroaryl groups, which are the focus of the present invention.

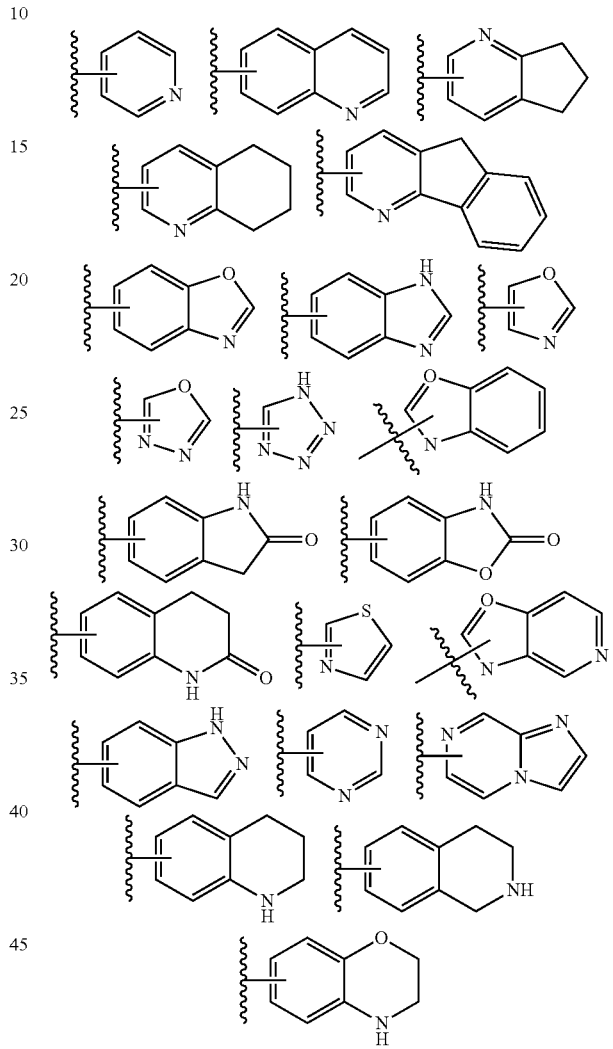

"Heterocyclyl" means a saturated or partially unsaturated monocyclic or polycyclic cyclic hydrocarbon substituent wherein one or more of the ring atoms are selected from nitrogen, oxygen or sulfur and the remaining ring atoms are carbon. Non-limiting examples of monocyclic heterocyclic groups include pyrrolidinyl, piperidinyl, piperazinyl, morpholinyl, thiomorpholinyl, homopiperazinyl. Polycyclic heterocyclic group refers to a heterocyclic group including a spiro ring, a fused ring, and a bridged ring. "Spirocyclic heterocyclyl" refers to a polycyclic heterocyclic group in which each ring of the system shares an atom (referred to as a spiro atom) with other rings in the system, wherein one or more of the ring atoms is selected from the group consisting of nitrogen and oxygen. Or sulfur, the remaining ring atoms are carbon. "Fused ring heterocyclyl" refers to a polycyclic heterocyclic group in which each ring of the system shares an adjacent pair of atoms with other rings in the system, and one or more rings may contain one or more double bonds, but none One ring has a fully conjugated pi-electron system, and wherein one or more ring atoms are selected from nitrogen, oxygen or sulfur, and the remaining ring atoms are carbon. "Bridged heterocyclyl" refers to a polycyclic heterocyclic group in which any two rings share two atoms that are not directly bonded, these may contain one or more double bonds, but none of the rings have a fully conjugated pi-electron system And wherein one or more of the ring atoms are selected from nitrogen, oxygen or sulfur, and the remaining ring atoms are carbon. If a heterocyclic group has both a saturated ring and an aromatic ring (for example, the saturated ring and the aromatic ring are fused together), the point attached to the parent must be on the saturated ring. Note: When the point attached to the parent is on the aromatic ring, it is called a heteroaryl group and is not called a heterocyclic group. Some examples of the heterocyclic group are as follows, and the present invention is not limited to the following heterocyclic group.

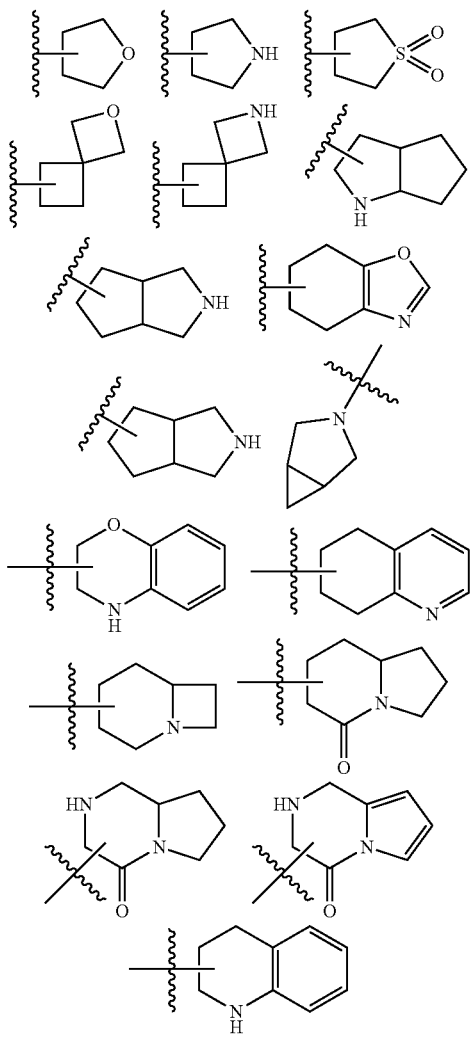

As used herein, the term "halogen", when used alone or as part of another substituent, refers to F, Cl, Br, and I.

As used herein, the term "substituted" (when with or without "optionally") means that one or more hydrogen atoms on a particular group are replaced by a particular substituent. The specific substituent is a substituent which is correspondingly described in the foregoing, or a substituent which appears in each embodiment. Unless otherwise indicated, an optionally substituted group may have a substituent selected from a particular group at any substitutable position of the group, which substituents may be the same or different at each position. A cyclic substituent, such as a heterocyclic group, may be attached to another ring, such as a cycloalkyl group, to form a spirobicyclic ring system, i.e., the two rings have a common carbon atom. Those skilled in the art will appreciate that the combinations of substituents contemplated by the present invention are those that are stable or chemically achievable. The substituents are, for example but not limited to, $C_{1-8}$ alkyl, $C_{2-8}$ alkenyl, $C_{2-8}$ alkynyl, $C_{3-8}$ cycloalkyl, 3- to 12-membered heterocyclic, aryl, Heteroaryl, halogen, hydroxy, carboxy (—COOH), $C_{1-8}$ aldehyde, $C_{2-10}$ acyl, $C_{2-10}$ ester, amino.

For convenience and in accordance with conventional understanding, the term "optionally substituted" or "optionally substituted" applies only to sites which are capable of being substituted by a substituent, and does not include those which are not chemically achievable.

As used herein, unless otherwise specified, the term "pharmaceutically acceptable salt" refers to a salt that is suitable for contact with the tissue of a subject (e.g., a human) without causing unpleasant side effects. In some embodiments, a pharmaceutically acceptable salt of a compound of the invention includes a salt (e.g., a potassium salt, a sodium salt, a magnesium salt, a calcium salt) of a compound of the invention having an acidic group or is basic A salt of a compound of the invention (for example, a sulfate, a hydrochloride, a phosphate, a nitrate, a carbonate).

General Synthetic Method for Compounds

The compound of the formula (I) of the present invention can be produced by the following method, however, the conditions of the method, such as the reactant, the solvent, the base, the amount of the compound used, the reaction temperature, the time required for the reaction, and the like are not limited to the following explanations. The compounds of the invention may also be conveniently prepared by combining various synthetic methods described in the specification or known in the art, such combinations being readily made by those skilled in the art to which the invention pertains.

In the production method of the present invention, each reaction is usually carried out in an inert solvent at a reaction temperature of −78° C. to 150° C. (preferably 20 to 120° C.). The reaction time in each step is usually from 0.5 to 48 hours, preferably from 2 to 12 hours.

Scheme A describes the general synthetic method for compound A6:

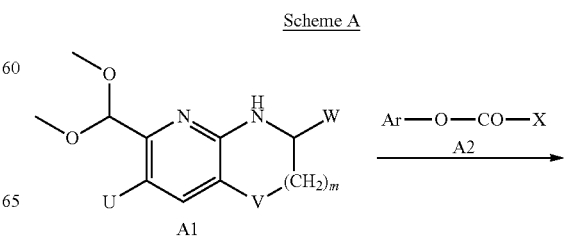

Scheme A

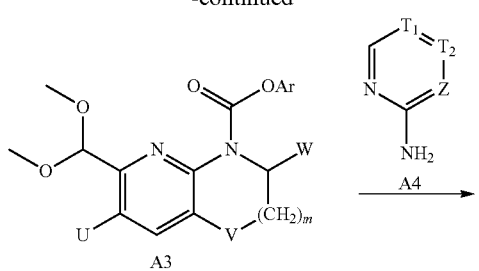
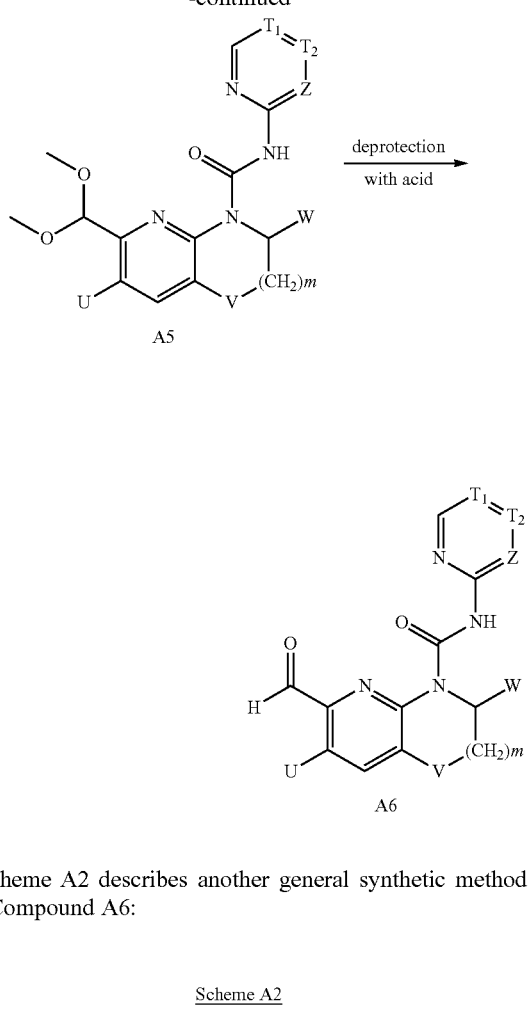
Scheme A2 describes another general synthetic method for Compound A6:
Scheme A2
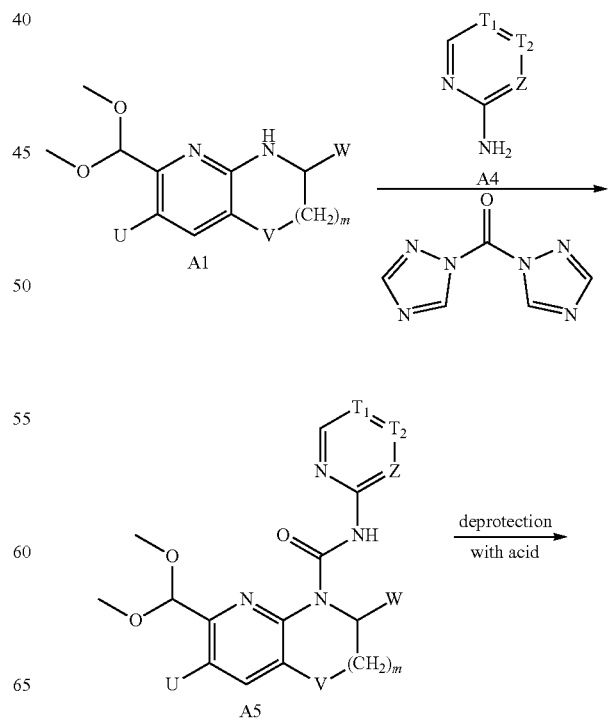
Scheme A1 describes another general synthetic method for Compound A6:
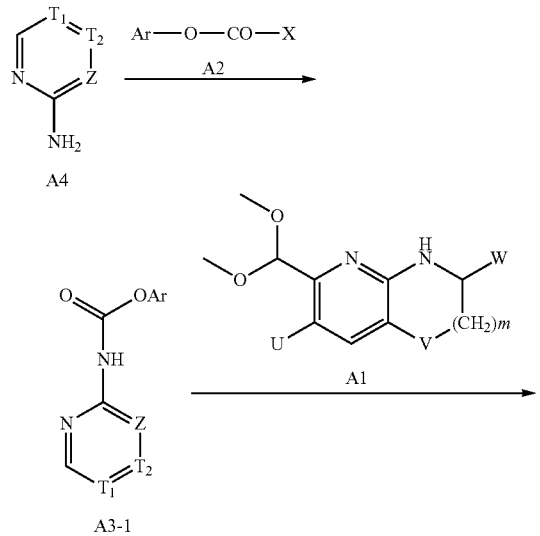

31
-continued
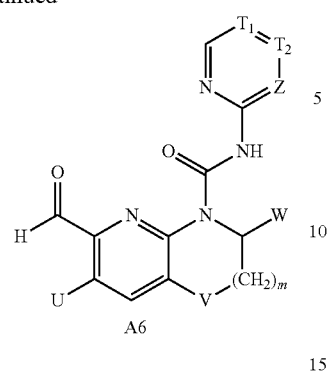
A6
Scheme B describes a general synthetic method for compound B6:
32
-continued
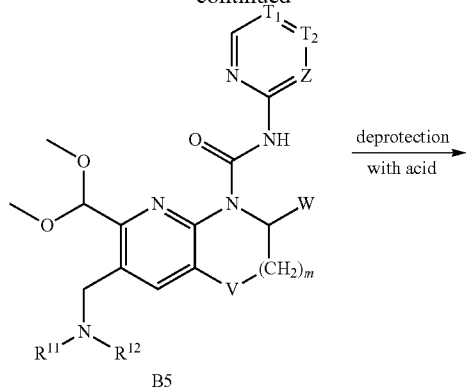
B5
deprotection with acid
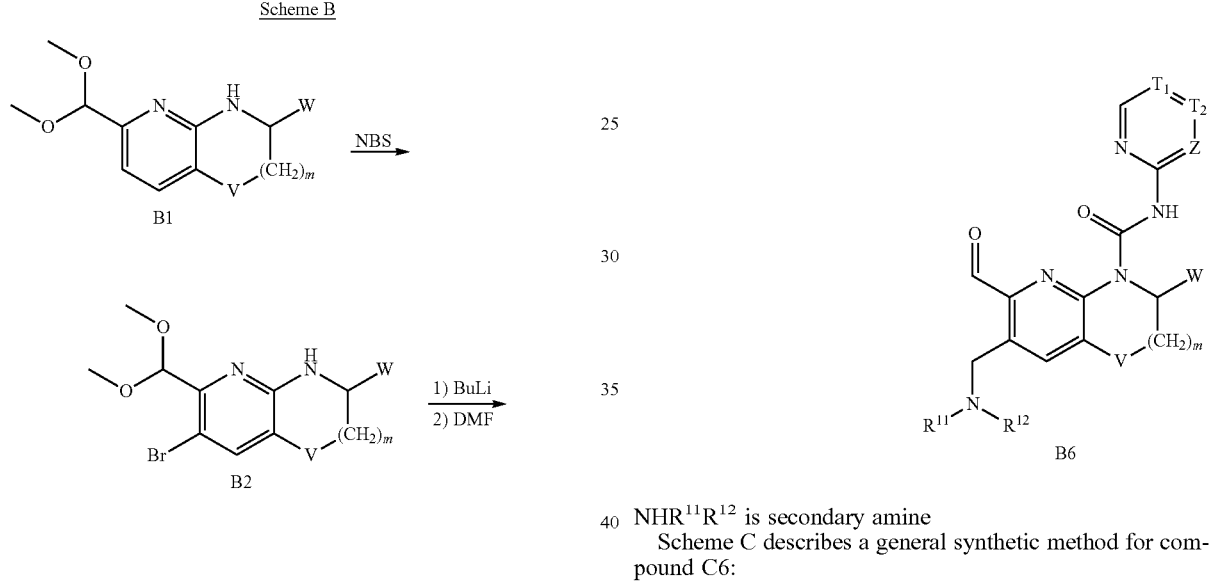
Scheme B
B1
NBS
B2
1) BuLi
2) DMF
B3
NHR¹¹R¹²
NaBH(OAc)₃
B4
A3-1
B6
NHR¹¹R¹² is secondary amine
Scheme C describes a general synthetic method for compound C6:
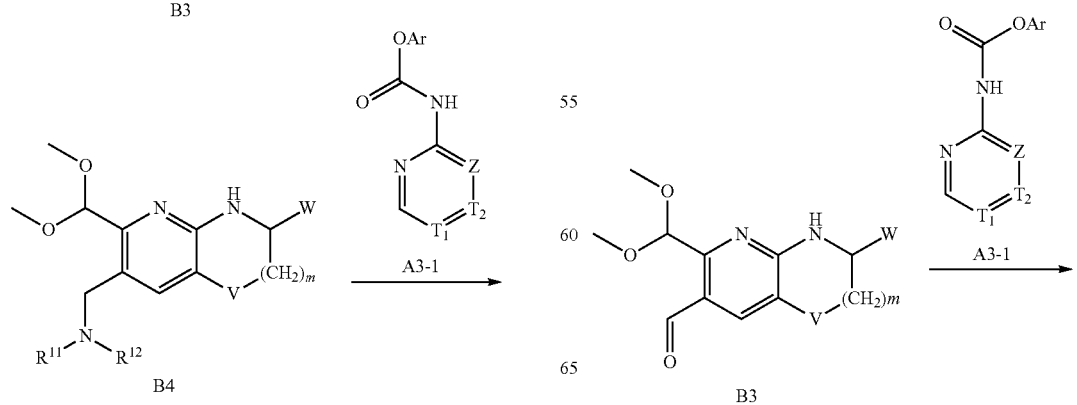
Scheme C
B3
A3-1

-continued
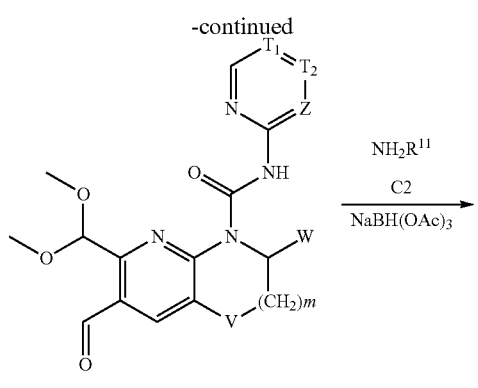
C1
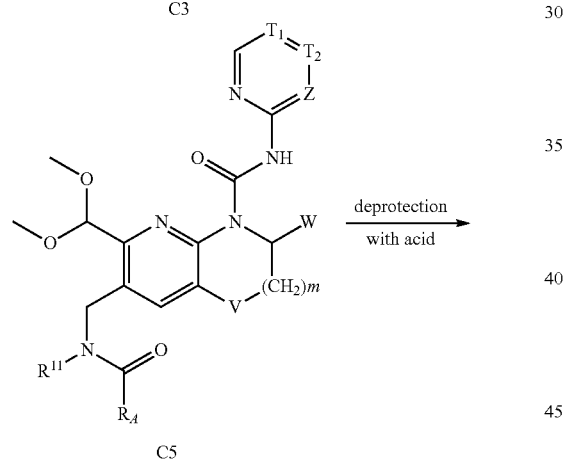
C3
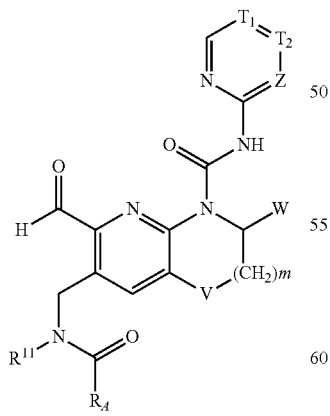
C5
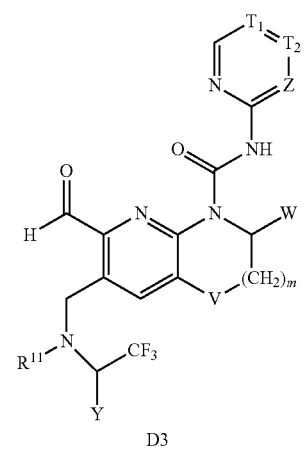
C6
$R_A$ is $C_{1-3}$ alkyl, —$CH_2$—OH, —$CH_2$—$OCH_3$, —$CH_2$—$N(CH_3)_2$ or $C(O)N(CH_3)_2$.
Scheme D describes a general synthetic method for compound D3:
Scheme D
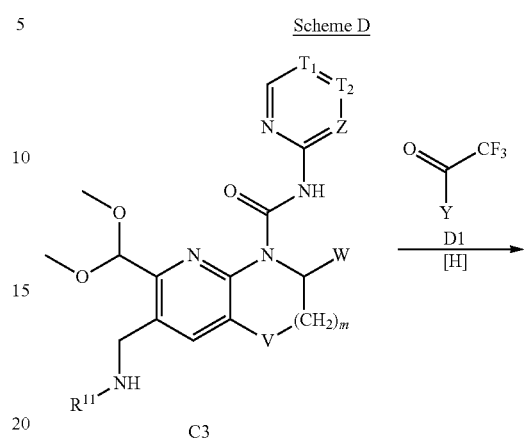
C3
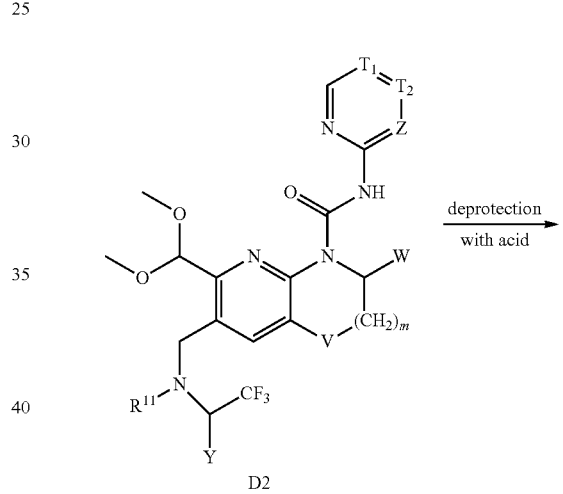
D2
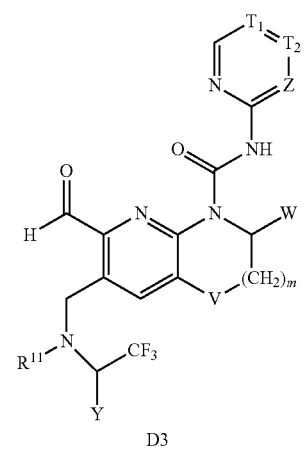
D3
Y is $C_{1-3}$ alkyl or $CH_2OH$.

Scheme E describes a general synthetic method for compound E7:
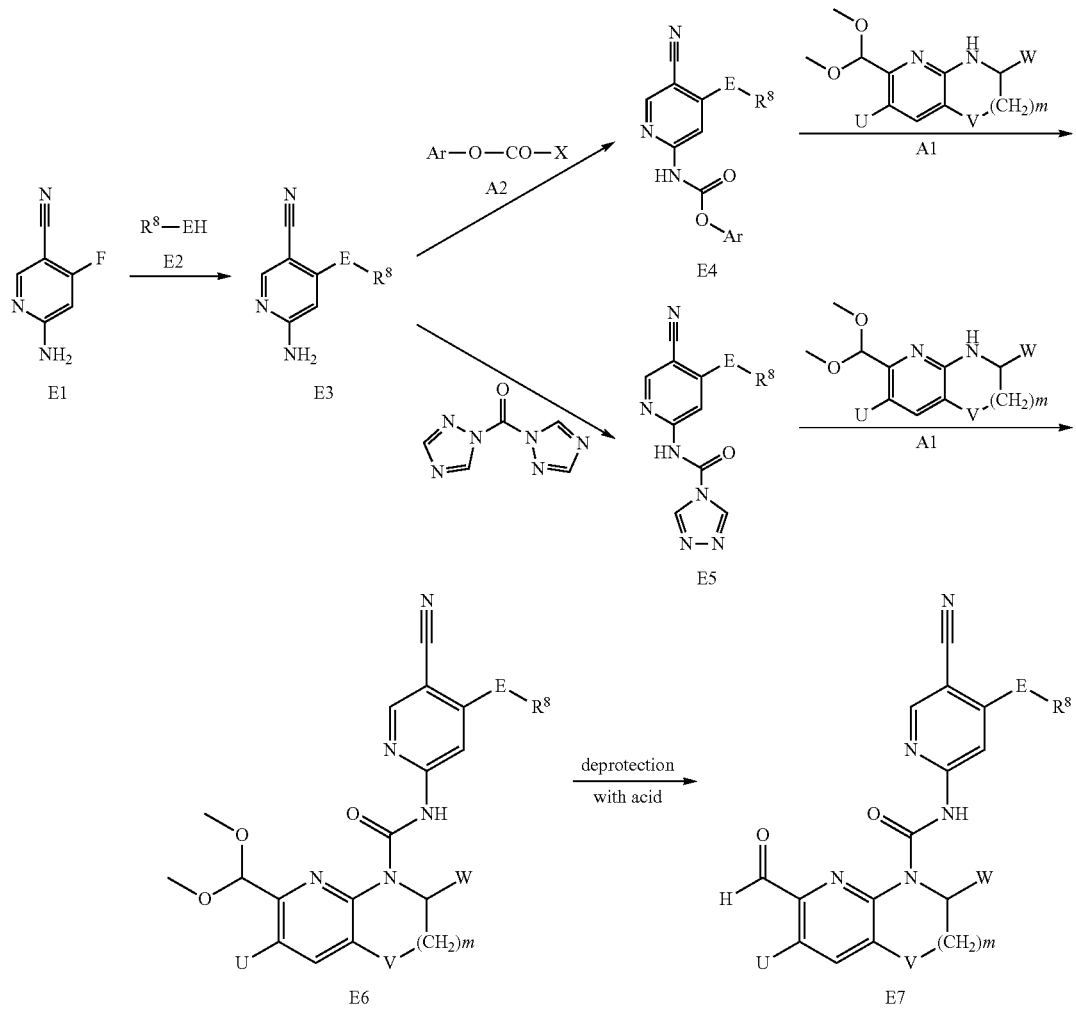
Wherein $R^B$-E- is selected from the group consisting of:
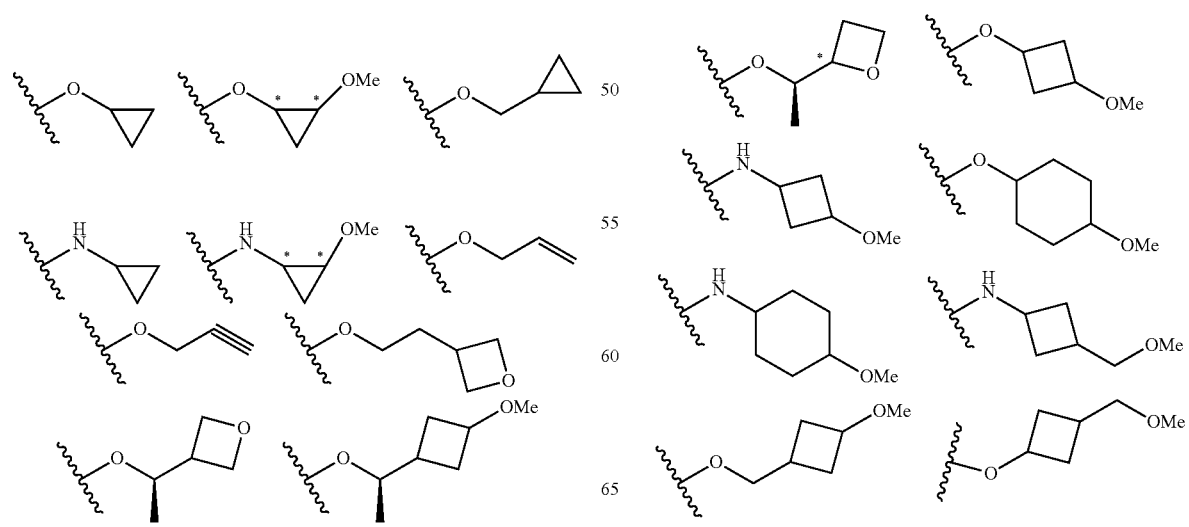

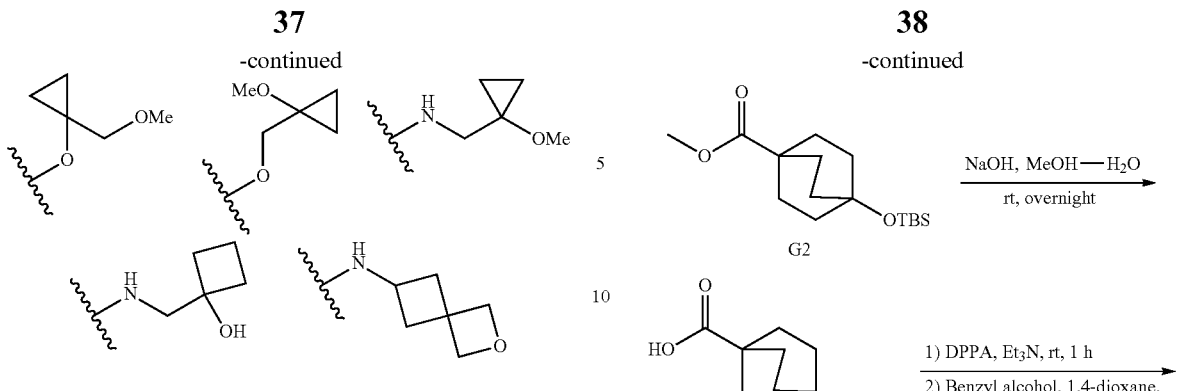

Scheme F describes another method of synthesis of intermediate E4. When the steric hindrance of $R^B$-EH is relatively large, the following synthesis method is the preferred one.

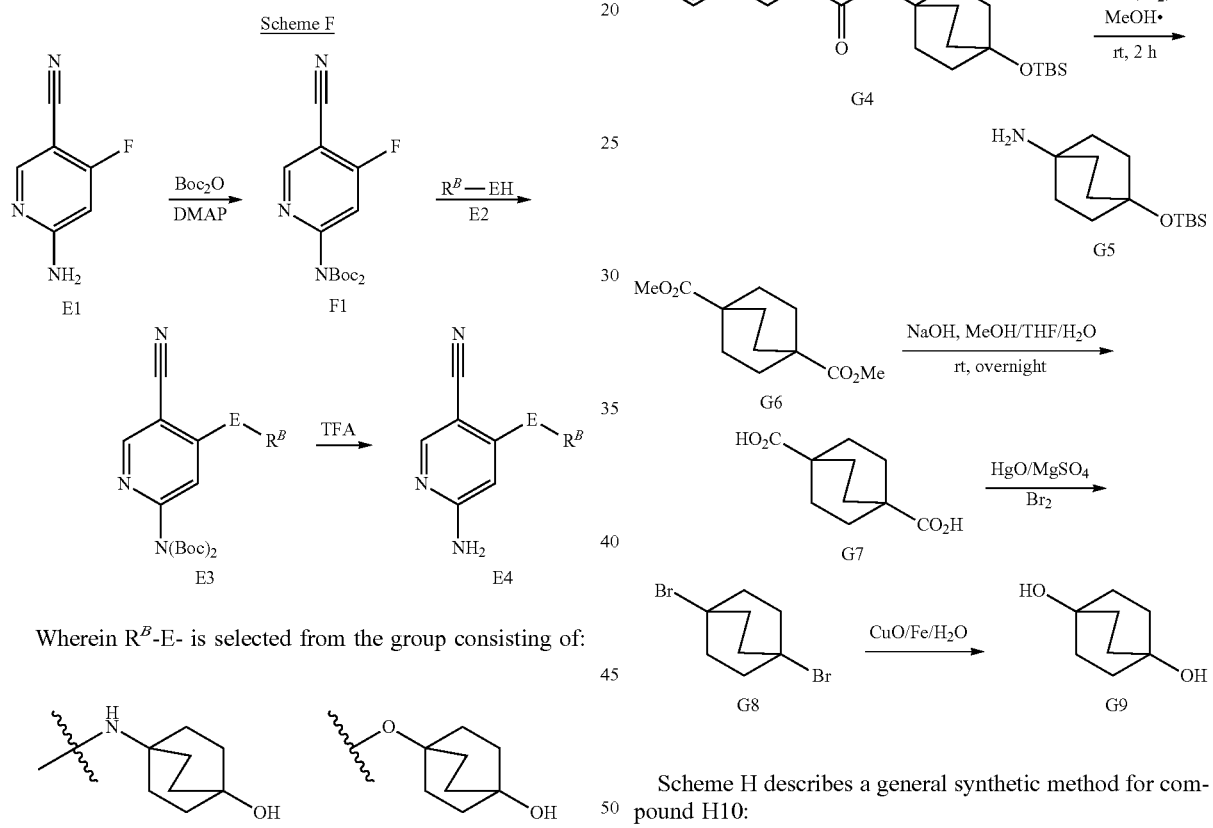

Wherein $R^B$-E- is selected from the group consisting of:

Target molecule E7 was synthesized from Intermediate E4 by following the procedure described in Scheme E. Scheme G describes the synthesis of intermediates G5 and G9:

Scheme H describes a general synthetic method for compound H10:

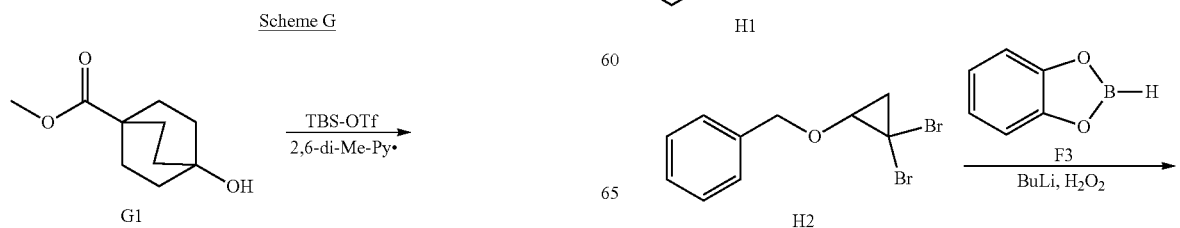

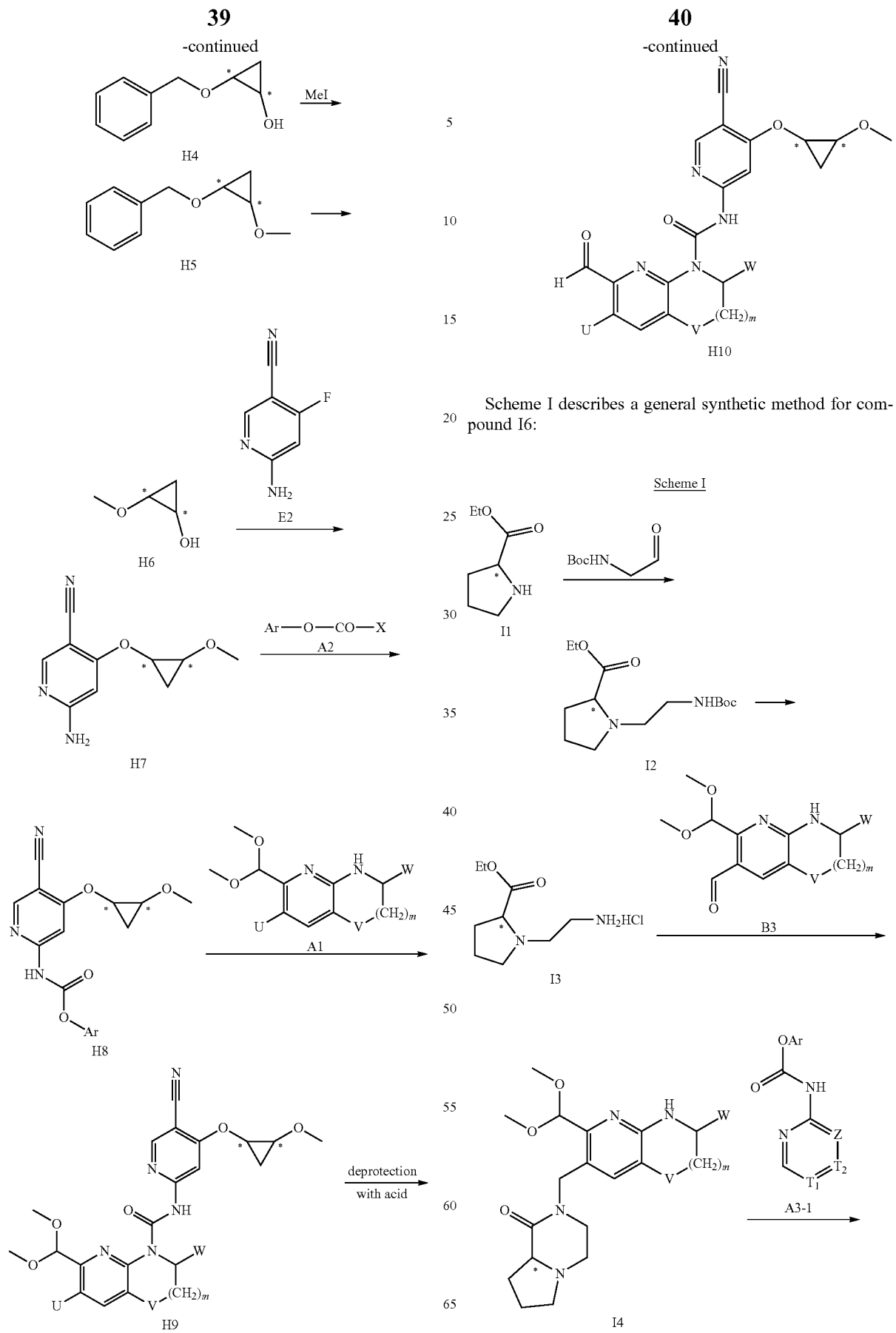
Scheme I describes a general synthetic method for compound I6:
Scheme I 41
-continued
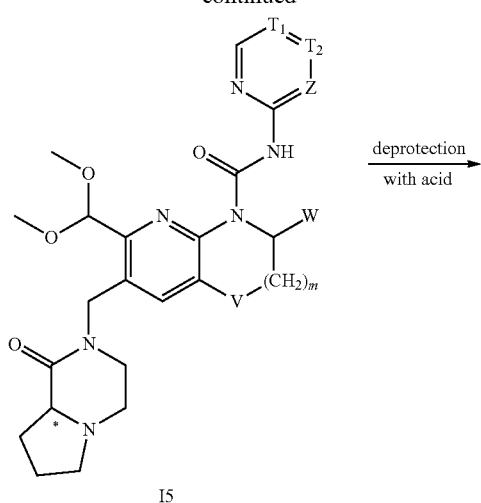
I5
deprotection with acid →
42
-continued
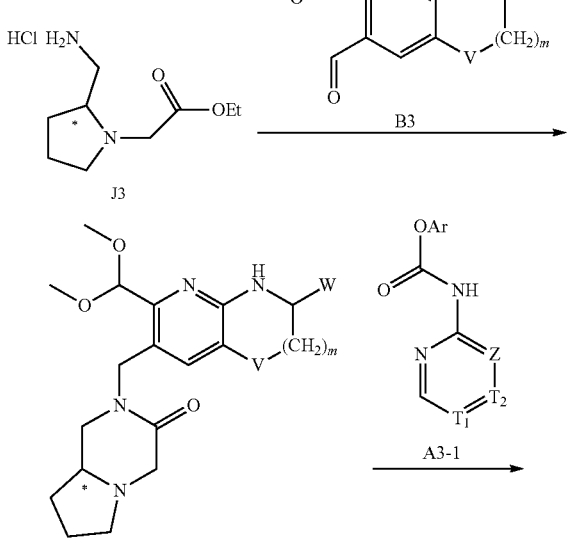
J3
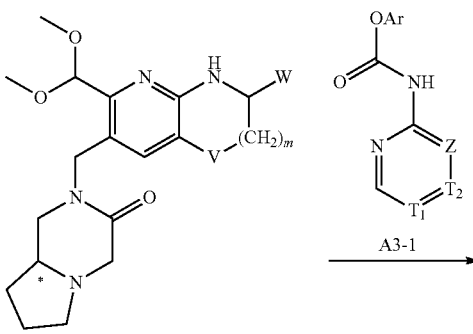
B3 →
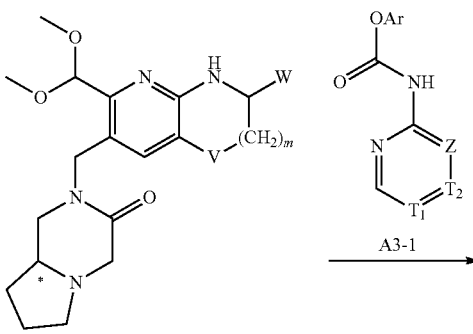
J4
A3-1 →
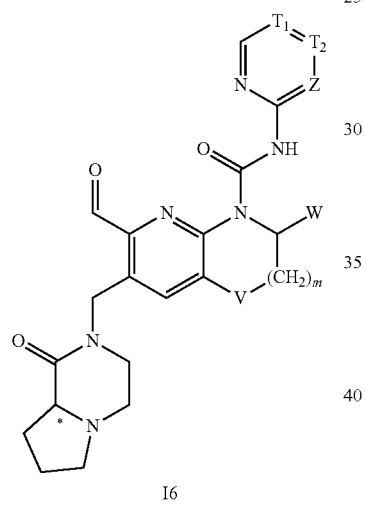
I6
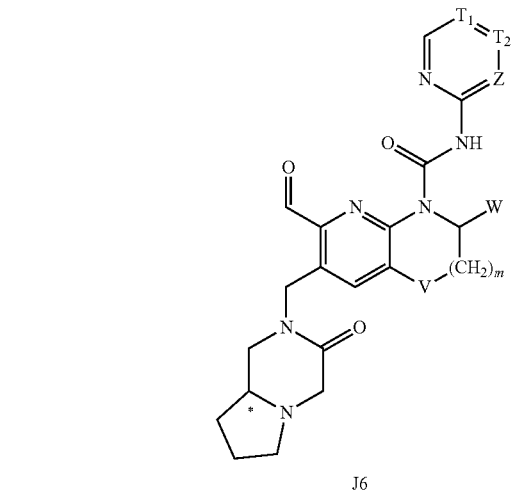
J5
deprotection with acid →
Scheme J describes a general synthetic method for Compound J6:
Scheme J
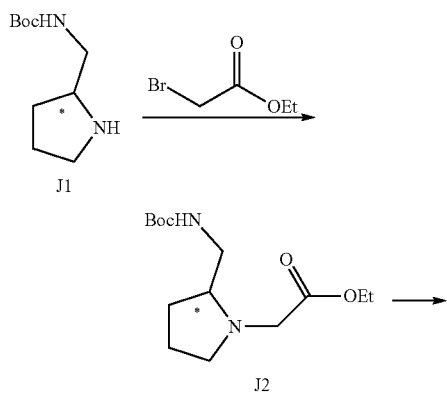
J1
J2
J6

Scheme K describes a general synthetic method for compound K7:
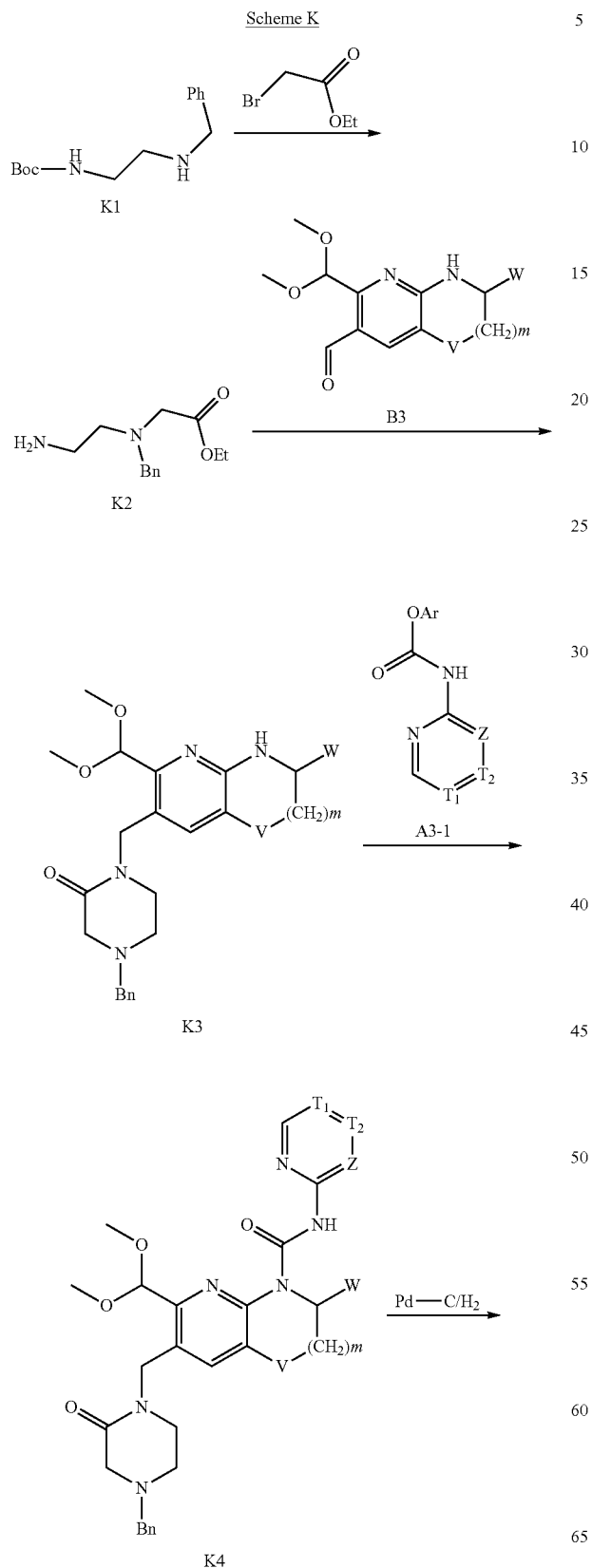
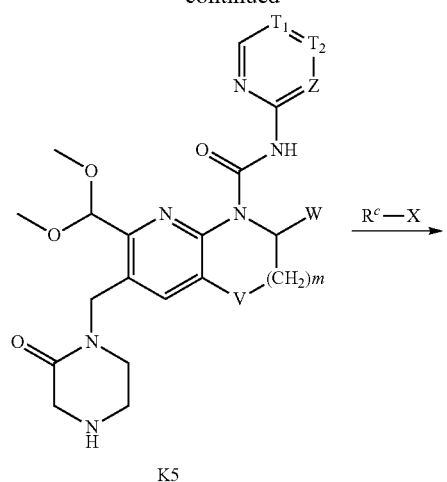
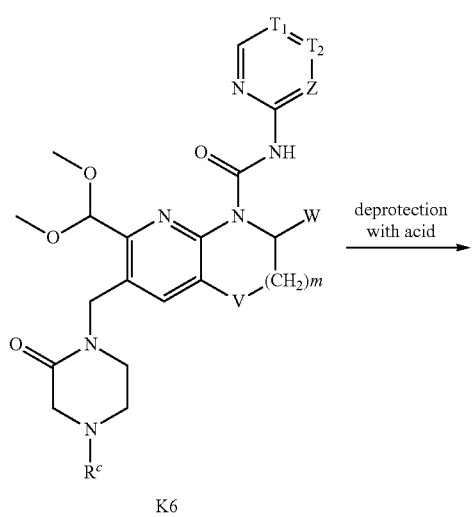
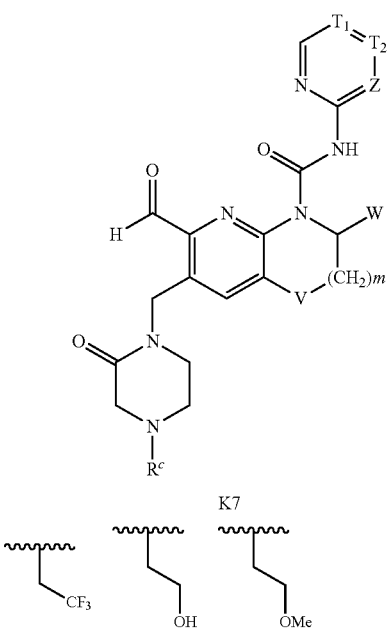

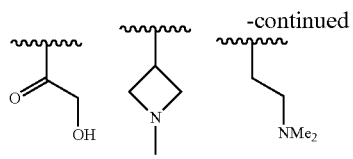
-continued

In each of the above reaction formulas, Ar is an aryl group, and X is a halogen, and the other groups are as defined above.

Pharmaceutically Acceptable Salts, Solvates, Stereoisomers, Tautomers

The term "pharmaceutically acceptable salt" as used herein refers to a salt of a compound of the invention and a pharmaceutically acceptable inorganic and organic acid, wherein preferred inorganic acids include, but are not limited to, hydrochloric acid, hydrogen Bromo acid, phosphoric acid, nitric acid, sulfuric acid; Preferred organic acids include, but are not limited to, formic acid, acetic acid, propionic acid, succinic acid, naphthalene disulfonic acid (1, 5), asiamic acid, oxalic acid, tartaric acid, lactic acid, salicylic acid, benzoic acid, pentane Acid, diethylacetic acid, malonic acid, succinic acid, fumaric acid, pimelic acid, adipic acid, maleic acid, malic acid, sulfamic acid, phenyl-propionic acid, gluconic acid, ascorbic acid, niacin, isonicotinic acid, methanesulfonic acid, p-toluenesulfonic acid, citric acid, and amino acids.

The term "pharmaceutically acceptable solvate" as used herein refers to a compound of the invention that forms a solvate with a pharmaceutically acceptable solvent, wherein the pharmaceutically acceptable solvent includes, but is not limited to, water, ethanol, methanol, isopropanol, tetrahydrofuran, dichloromethane.

The term "pharmaceutically acceptable stereoisomer" as used herein means that the chiral carbon atom to which the compound of the invention relates may be in the R configuration, in the S configuration, or a combination thereof.

Pharmaceutical Composition and Method of Administration

Since the compound of the present invention has excellent inhibitory activity against FGFR4, the compound of the present invention and various crystalline forms thereof, a pharmaceutically acceptable inorganic or organic salt, hydrate or solvate, and a compound containing the present invention as main active ingredients in a pharmaceutical composition can be used for the treatment, prevention, and alleviation of diseases associated with FGFR4 activity and expression. According to the current technology, the compounds of the present invention can be used for the treatment of diseases (but not limited to): various cancers, such as lung cancer, bladder cancer, breast cancer, stomach cancer, liver cancer, salivary gland sarcoma, ovarian cancer, prostate cancer, cervical cancer, epithelial cell carcinoma, multiple myeloma, pancreatic cancer, lymphoma, chronic myelogenous leukemia, lymphocytic leukemia, cutaneous T-cell lymphoma, etc.; bone-related diseases such as bone dysplasia, dysplasia, dwarfism, crouzing syndrome, etc.; T cell-mediated inflammation and autoimmune diseases such as rheumatoid arthritis, collagen II arthritis, multiple sclerosis, systemic lupus erythematosus, psoriasis, juvenile diabetes, Sjogren's syndrome, thyroid disease, sarcoidosis, inflammatory bowel disease, celiac disease and so on. The pharmaceutical compositions of the present invention comprise a safe or effective amount of a compound of the present invention or a pharmacologically acceptable salt thereof, and a pharmaceutically acceptable excipient or carrier. By "safe and effective amount" it is meant that the amount of the compound is sufficient to significantly improve the condition without causing serious side effects. In general, the pharmaceutical compositions contain from 1 to 2000 mg of the compound of the invention per agent, more preferably from 5 to 200 mg of the compound of the invention per agent. Preferably, the "one dose" is a capsule or tablet.

"Pharmaceutically acceptable carrier" means: one or more compatible solid or liquid fillers or gel materials which are suitable for human use and which must be of sufficient purity and of sufficiently low toxicity. By "compatibility" it is meant herein that the components of the composition are capable of intermingling with the compounds of the invention and with each other without significantly reducing the potency of the compounds. Examples of pharmaceutically acceptable carriers are cellulose and its derivatives (such as sodium carboxymethylcellulose, sodium ethylcellulose, cellulose acetate, etc.), gelatin, talc, solid lubricants (such as stearic acid), magnesium stearate), calcium sulfate, vegetable oil (such as soybean oil, sesame oil, peanut oil, olive oil, etc.), polyols (such as propylene glycol, glycerin, mannitol, sorbitol, etc.), emulsifiers (such as Tween®), wetting agents (such as sodium lauryl sulfate), colorants, flavoring agents, stabilizers, antioxidants, Preservatives, pyrogen-free water, etc.

The mode of administration of the compound or pharmaceutical composition of the present invention is not particularly limited, and representative modes of administration include, but are not limited to, oral, intratumoral, rectal, parenteral (intravenous, intramuscular or subcutaneous), and topical administration.

Solid dosage forms for oral administration include capsules, tablets, pills, powders, and granules. In these solid dosage forms, the active compound is mixed with at least one conventional inert excipient (or carrier), such as sodium citrate or dicalcium phosphate, or mixed with the following ingredients: (a) fillers or compatibilizers such as starch, lactose, sucrose, glucose, mannitol and silicic acid; (b) binders such as hydroxymethylcellulose, alginates, gelatin, polyvinylpyrrolidone, sucrose and Arabic gum; (c) a humectant such as glycerin; (d) a disintegrant such as agar, calcium carbonate, potato starch or tapioca starch, alginic acid, certain complex silicates, and sodium carbonate; (e) a slow solvent, For example, paraffin wax; (f) an absorption accelerator, for example, a quaternary amine compound; (g) wetting agents such as cetyl alcohol and glyceryl monostearate; (h) adsorbents such as kaolin; and (i) lubricants such as talc, calcium stearate, magnesium stearate, solids Polyethylene glycol, sodium lauryl sulfate, or a mixture thereof. In capsules, tablets, and pills, the dosage form may also contain a buffer.

Solid dosage forms such as tablets, dragees, capsules, pills, and granules can be prepared with coatings and shells such as enteric coatings and other materials known in the art. They may contain opacifying agents and the release of the active compound or compound in such a composition may be released in a certain part of the digestive tract in a delayed manner. Examples of embedding components that can be employed are polymeric materials and waxy materials. If necessary, the active compound may also form microencapsulated forms with one or more of the above excipients.

Liquid dosage forms for oral administration include pharmaceutically acceptable emulsions, solutions, suspensions, syrups or elixirs. In addition to the active compound, the liquid dosage form can comprise inert diluents conventionally employed in the art, such as water or other solvents, solubilizers and emulsifiers, for example, ethanol, isopropanol, ethyl carbonate, ethyl acetate, propylene glycol, 1,3-butylene glycol, dimethylformamide and oils, especially cottonseed oil, peanut oil, corn germ oil, olive oil, castor oil and sesame oil or a mixture of these.

In addition to these inert diluents, the compositions may contain adjuvants such as wetting agents, emulsifying and suspending agents, sweetening agents, flavoring agents, and flavoring agents.

In addition to the active compound, the suspension may contain suspending agents, for example, ethoxylated isostearyl alcohol, polyoxyethylene sorbitol and sorbitan esters, microcrystalline cellulose, aluminum methoxide and agar or mixtures of these and the like.

Compositions for parenteral injection may comprise a physiologically acceptable sterile aqueous or nonaqueous solution, dispersion, suspension or emulsion, and sterile powder for reconstitution into sterile injectable solutions or dispersions. Suitable aqueous and nonaqueous vehicles, diluents, solvents or excipients include water, ethanol, polyols and suitable mixtures thereof.

Dosage forms for the compounds of the invention for topical administration include ointments, powders, patches, propellants and inhalants. The active ingredient is mixed under sterile conditions with a physiologically acceptable carrier and any preservatives, buffers, or propellants which may be required if necessary.

The compounds of the invention may be administered alone or in combination with other pharmaceutically acceptable compounds.

When a pharmaceutical composition is used, a safe and effective amount of a compound of the invention is administered to a mammal (e.g., a human) in need of treatment wherein the dosage is a pharmaceutically effective effective dosage. For a 60 kg body weight, the daily dose is usually from 1 to 2000 mg, preferably from 5 to 500 mg. Of course, specific doses should also consider factors such as the route of administration, the health of the patient, etc., which are within the skill of the skilled physician.

The Main Advantages of the Invention Include:
1. Provided a compound of formula (I).
2. Providing a novel structure of FGFR4 inhibitor, which inhibits the activity of FGFR4 at very low concentrations, and its preparation and use.
3. Providing a class of pharmaceutical compositions for treating diseases associated with FGFR4 activity.

The invention is further illustrated below in conjunction with specific embodiments. It is to be understood that the examples are not intended to limit the scope of the invention. The experimental methods in the following examples which do not specify the specific conditions are usually carried out according to conventional conditions or according to the conditions recommended by the manufacturer. Percentages and parts are by weight unless otherwise stated.

Example 1. Preparation of Compound 1

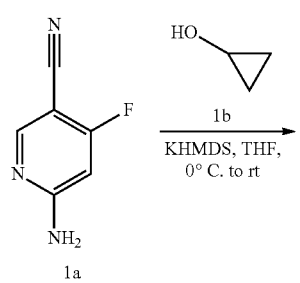

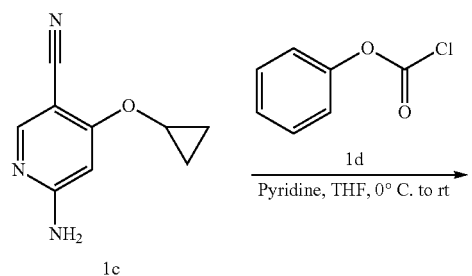

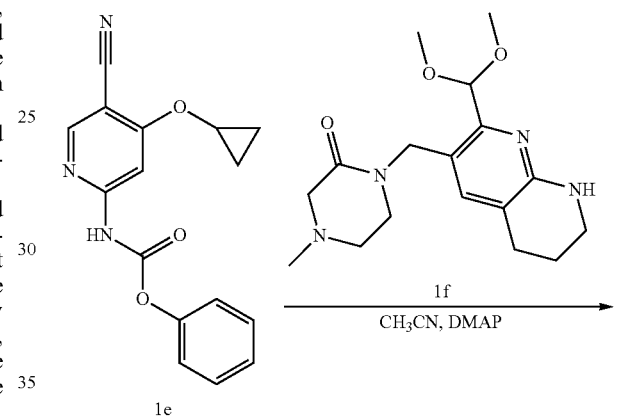

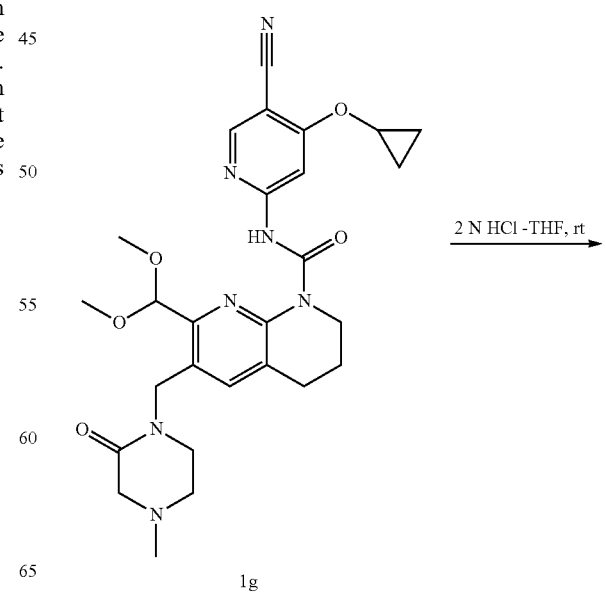

-continued

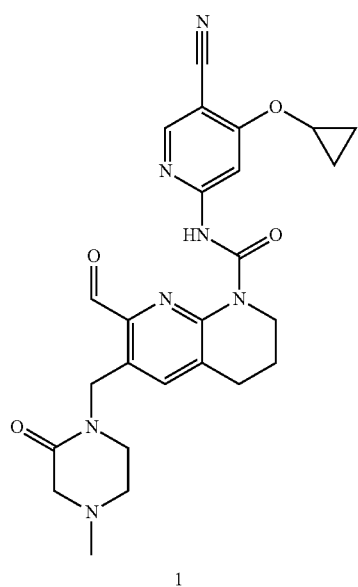 [SMILES: CN1CCN(Cc2cc3c(nc2C=O)N(C(=O)Nc2cc(OC4CC4)c(C#N)cn2)CCC3)C(=O)C1]

1

Cyclopropanol (317 mg, 5.46 mmol) was dissolved in dry THF (12 mL), to which was added KHMDS (21% THF solution, 4.1 g, 4.32 mmol) dropwise at 0° C. under ice bath. The mixture was stirred at 0° C. for 20 minutes, followed by addition of 1a (150 mg, 1.09 mmol), then was stirred at room temperature for 5 h. TLC showed the reaction was complete. The reaction mixture was added to saturated aq. NH$_4$Cl (20 mL) dropwise, extracted with EtOAc (15 mL×3), the combined organic phase was washed with brine, dried over MgSO$_4$, and filtered. The filtrate was concentrated in vacuo, the residue was purified via preparative TLC (CH$_2$Cl$_2$/MeOH=70/1) to afford 1c (60 mg, yield 31%). MS 176.2 [M+H]$^+$.

To a solution of compound 1c (60 mg, 0.34 mmol) and pyridine (80 mg, 1.01 mmol) in dry THF (2 mL) was added phenyl chloroformate (678 mg, 10.79 mmol) slowly. After addition was complete, the reaction mixture was stirred at room temperature for 16 hours. TLC showed the reaction was complete. The reaction was added to water (5 mL), extracted with EtOAc (10 mL×2), the combined organic phase was washed with brine, dried over Na$_2$SO$_4$ and filtered. The filtrate was concentrated in vacuo, the residue was purified via preparative TLC (CH$_2$Cl$_2$) to afford 1e (60 mg, yield 59%) as yellow solid. MS 296.2 [M+M]$^+$.

Compound 1e (55 mg, 0.19 mmol), 1f (64 mg, 0.19 mmol) and DMAP (23 mg, 0.19 mmol) were dissolved in acetonitrile (3 mL), the reaction mixture was stirred at 60° C. for 2 hours. TLC results showed the reaction was finished. The reaction was added to water (10 mL), extracted with EtOAc (10 mL×3), the combined organic phase was washed with brine, dried over Na$_2$SO$_4$ and filtered. The filtrate was concentrated in vacuo, the residue was purified via preparative TLC (CH$_2$Cl$_2$/CH$_3$OH=25/1) to afford 1g (55 mg, yield 55%) as a yellow solid. MS 536.2 [M+H].

Compound 1g (50 mg, 0.09 mmol) was dissolved in THF (2 mL), which was added HCl (2 N, 0.5 mL). The reaction mixture was stirred at room temperature for 1 hour. Then the reaction mixture was poured into saturated aq. NaHCO$_3$ (5 mL), extracted with EtOAc (5 mL×3), the combined organic phase was washed by brine, dried over Na$_2$SO$_4$ and filtered, The filtrate was concentrated in vacuo, the crude product was washed by petroleum ether/CH$_2$Cl$_2$ (20/1) to afford 1 (28 mg, yield 61%) as an off-white solid. $^1$H NMR (400 MHz, CDCl$_3$): δ 13.89 (s, 1H), 10.25 (s, 1H), 8.35 (s, 1H), 8.27 (s, 1H), 7.64 (s, 1H), 5.09 (s, 2H), 4.13-4.08 (m, 2H), 4.04-3.96 (m, 1H), 3.40-3.32 (m, 2H), 3.20 (s, 2H), 2.97-2.92 (m, 2H), 2.70-2.62 (m, 2H), 2.36 (s, 3H), 2.09-2.00 (m, 2H), 0.96-0.89 (m, 4H). MS 490.3 [M+H]$^+$.

Example 2. Preparation of Compound 2

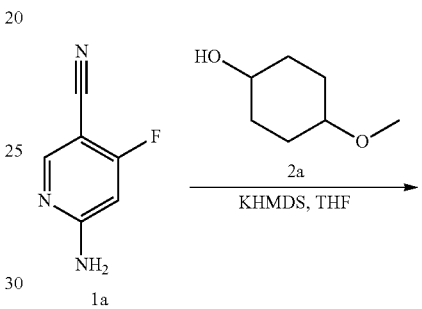

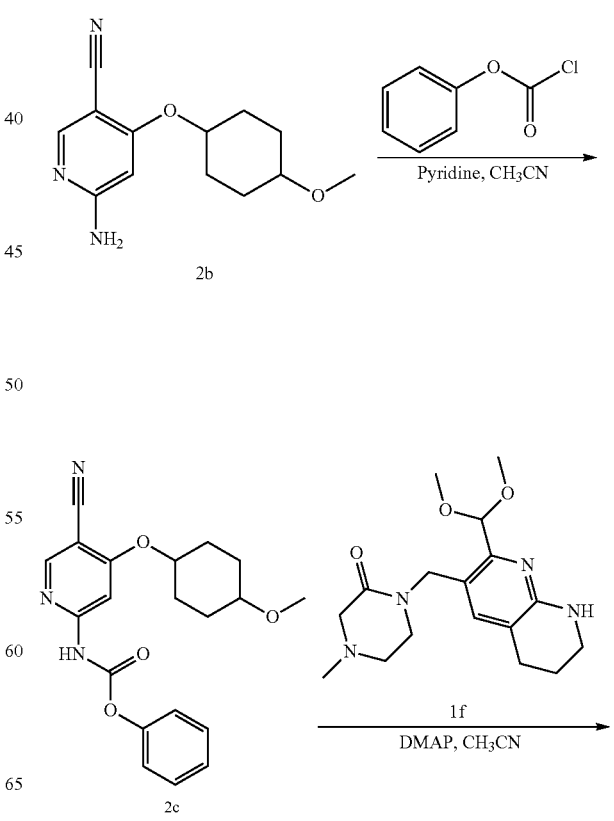

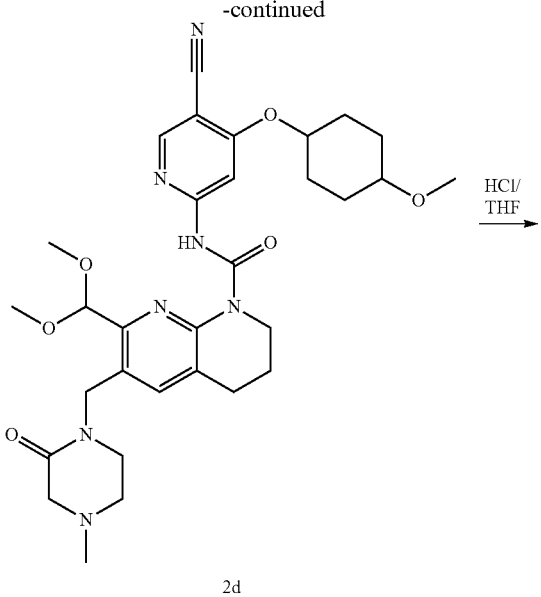

2d

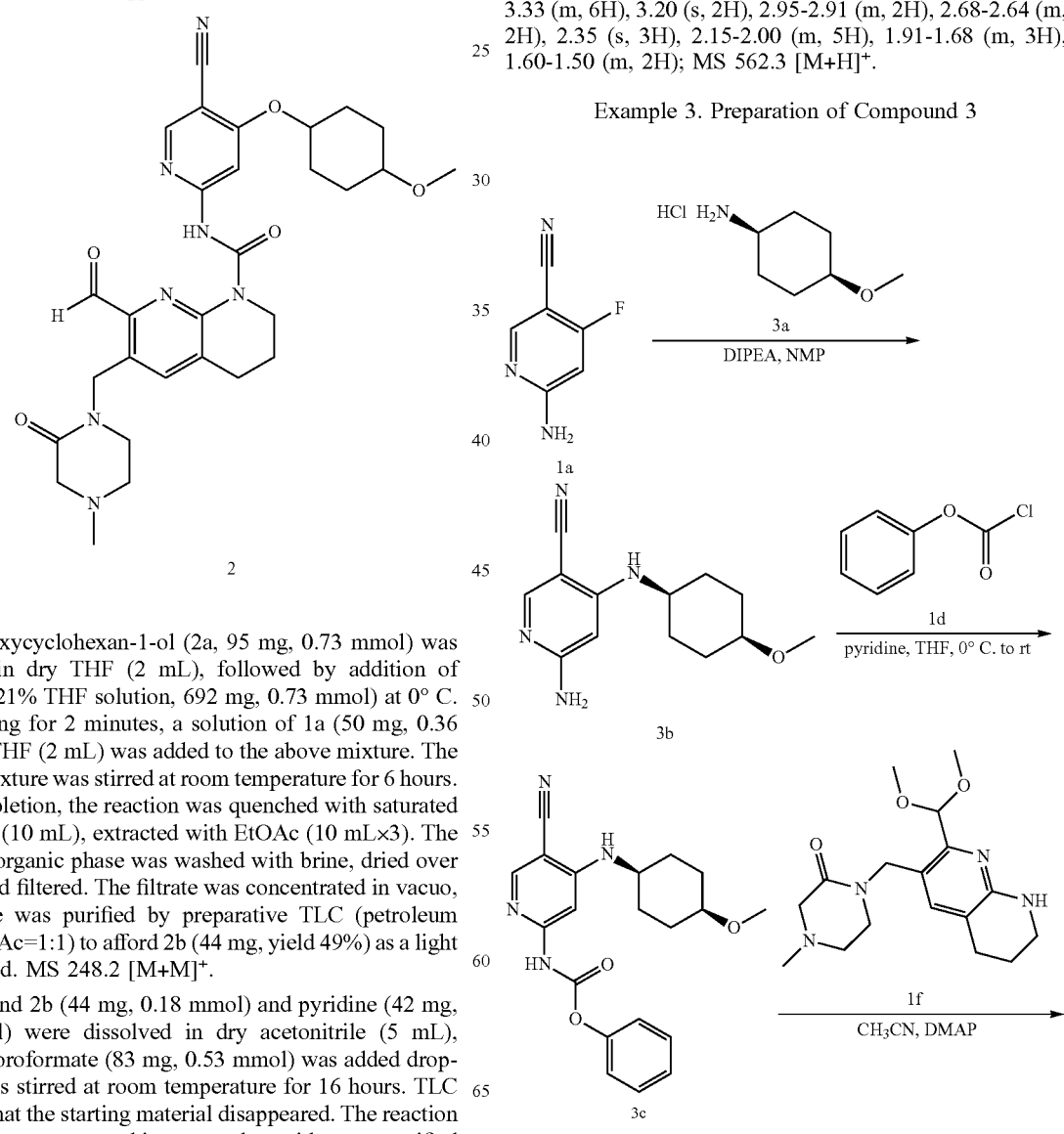

2

4-Methoxycyclohexan-1-ol (2a, 95 mg, 0.73 mmol) was dissolved in dry THF (2 mL), followed by addition of KHMDS (21% THF solution, 692 mg, 0.73 mmol) at 0° C. After stirring for 2 minutes, a solution of 1a (50 mg, 0.36 mmol) in THF (2 mL) was added to the above mixture. The reaction mixture was stirred at room temperature for 6 hours. After completion, the reaction was quenched with saturated aq. NH₄Cl (10 mL), extracted with EtOAc (10 mL×3). The combined organic phase was washed with brine, dried over Na₂SO₄ and filtered. The filtrate was concentrated in vacuo, the residue was purified by preparative TLC (petroleum ether/EAOAc=1:1) to afford 2b (44 mg, yield 49%) as a light yellow solid. MS 248.2 [M+M]⁺.

Compound 2b (44 mg, 0.18 mmol) and pyridine (42 mg, 0.53 mmol) were dissolved in dry acetonitrile (5 mL), phenyl chloroformate (83 mg, 0.53 mmol) was added dropwise. It was stirred at room temperature for 16 hours. TLC indicated that the starting material disappeared. The reaction mixture was concentrated in vacuo, the residue was purified via preparative TLC (petroleum ether/EAOAc=1:1) to afford compound 2c (37 mg, yield 57%) as a light yellow solid. MS 368.2 [M+H]⁺.

Compound 2c (37 mg, 0.10 mmol), 1f (34 mg, 0.10 mmol) and DMAP (12 mg, 0.10 mmol) were dissolved in dry acetonitrile (3 mL), and the resulting solution was stirred at 90° C. for 1 hour. TLC indicated the starting material disappeared. The reaction mixture was directly purified via preparative TLC (EtOAC) to afford 2d (25 mg, yield 41%) as a pale solid. MS 608.3 [M+H]⁺. Compound 2d (25 mg, 0.04 mmol) was dissolved in dry THF (3 mL), then aqueous HCl solution (2 N, 0.2 mL) was added. The reaction solution was stirred at room temperature for 1.5 hours. Then the reaction mixture was poured into saturated aq. NaHCO₃ (5 mL), extracted with EtOAc (10 mL×3), the combined organic phase was washed with brine, dried over Na₂SO₄ and filtered. The filtrate was concentrated in vacuo, the crude product was purified via preparative TLC (petroleum ether/CH₂Cl₂ 25/1) to afford compound 2 (13 mg, yield 57%) as an off-white solid. ¹H NMR (400 MHz, DMSO-d₆): δ 13.84 (s, 1H), 10.24 (s, 1H), 8.35 (s, 1H), 7.93 (s, 1H), 7.64 (s, 1H), 5.09 (s, 2H), 4.73-4.65 (m, 1H), 4.10-4.06 (m, 2H), 3.41-3.33 (m, 6H), 3.20 (s, 2H), 2.95-2.91 (m, 2H), 2.68-2.64 (m, 2H), 2.35 (s, 3H), 2.15-2.00 (m, 5H), 1.91-1.68 (m, 3H), 1.60-1.50 (m, 2H); MS 562.3 [M+H]⁺.

Example 3. Preparation of Compound 3

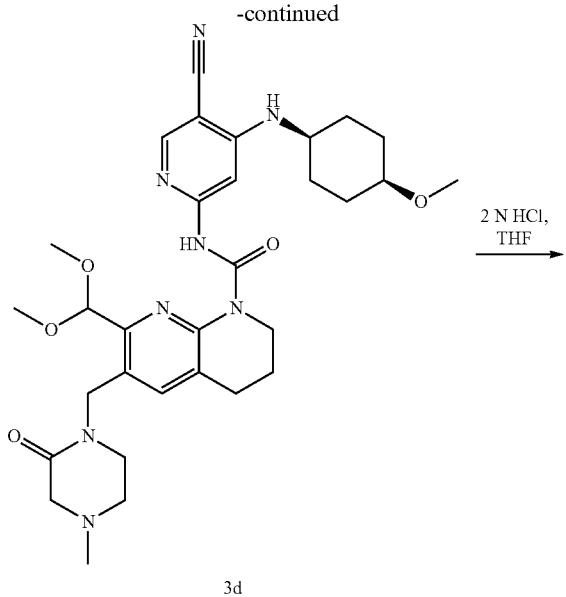

3d

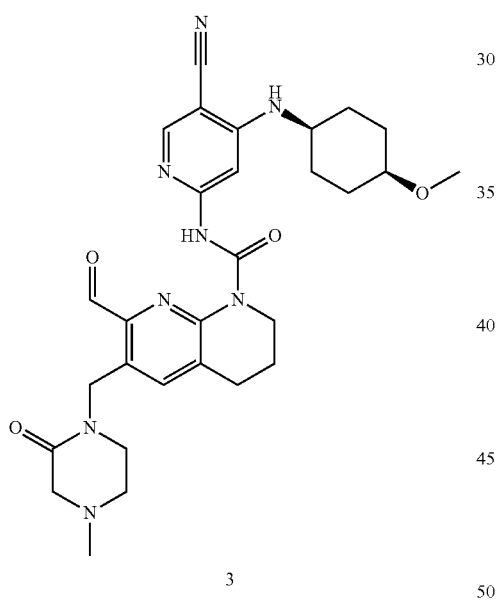

3

Compound 1a (60 mg, 0.44 mmol) was dissolved in NMP (1 mL) and was added cis-4-methoxycyclohexan-1-amine hydrochloride (62 mg, 0.51 mmol), DIPEA (114 mg, 0.88 mmol), then was stirred at 100° C. for 16 hours. The reaction mixture was cooled to room temperature, and was added to water, extracted with $CH_2Cl_2$ (10 mL×3). The combined organic phase was washed with brine (10 mL), dried over $Na_2SO_4$ and filtered, the filtrate was concentrated in vacuo, the crude product was purified via preparative TLC ($CH_2Cl_2$/MeOH=10/1) to afford compound 3b (35 mg, yield 32%) as a pale yellow solid.

Compound 3b (35 mg, 0.14 mmol) and pyridine (22 mg, 0.28 mmol) was dissolved in dry THF (3 mL), was added phenyl chloroformate (83 mg, 0.53 mmol) at 0° C. under stirring. The reaction mixture was stirred at room temperature overnight. TLC results showed the reaction was finished. The reaction was added to water, extracted with EtOAc (10 mL×2), the combined organic phase was washed by brine, dried over $Na_2SO_4$ and filtered, The filtrate was concentrated in vacuo, the residue was purified via preparative TLC ($CH_2Cl_2$) to afford compound 3c (12 mg, yield 23%) as a yellow solid. MS 367.3 $[M+H]^+$.

Compound 3c (12 mg, 0.033 mmol), 1f (11 mg, 0.033 mmol) and DMAP (4 mg, 0.033 mmol) were dissolved in dry acetonitrile (3 mL), then the reaction mixture was stirred at 90° C. for 2 hours. TLC showed the starting material disappeared. The reaction mixture was added to water, extracted with EtOAc (10 mL×3), the combined organic phase was washed with brine, dried over $Na_2SO_4$ and filtered. The filtrate was concentrated in vacuo, the residue was purified via preparative TLC ($CH_2Cl_2$/MeOH=20/1) to afford compound 3d (5 mg, yield 25%) as a yellow solid. MS 607.3 $[M+M]^+$.

Compound 3d (5 mg, 0.0082 mmol) was dissolved in THF (1 mL), and HCl (2 N, 0.1 mL) was added, the reaction mixture was stirred at room temperature for 1 hour. The reaction mixture was concentrated in vacuo, the residue was purified via preparative TLC ($CH_2Cl_2$/MeOH=25/1) to afford compound 3 (0.6 mg, yield 13%) as a gray solid. $^1$H NMR (400 MHz, $CDCl_3$): δ 13.58 (s, 1H), 10.23 (s, 1H), 8.17 (s, 1H), 7.63 (s, 1H), 7.57 (s, 1H), 7.52 (s, 1H), 5.09 (s, 2H), 4.78-4.76 (m, 1H), 4.10-4.07 (m, 2H), 3.98-3.96 (m, 1H), 3.36 (s, 3H), 3.36-3.33 (m, 2H), 3.17-3.21 (m, 1H), 2.93-2.9 (m, 2H), 2.35 (s, 3H), 2.05-2.03 (m, 3H), 131-1.25 (m, 10H); MS 561.3 $[M+H]^+$.

Example 4. Preparation of Compound 4

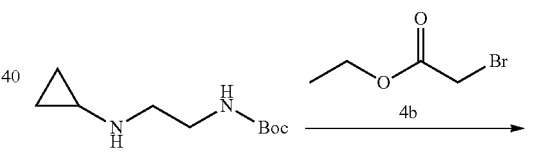

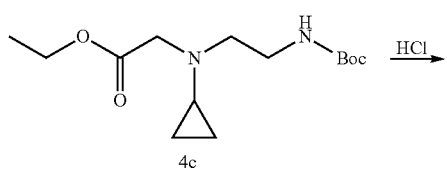

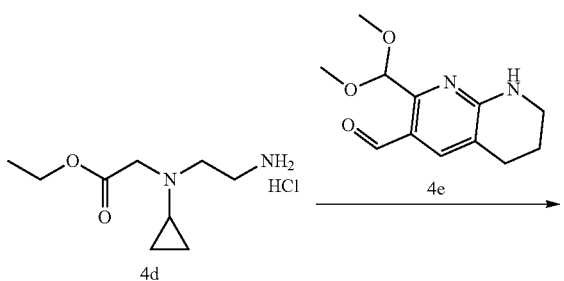

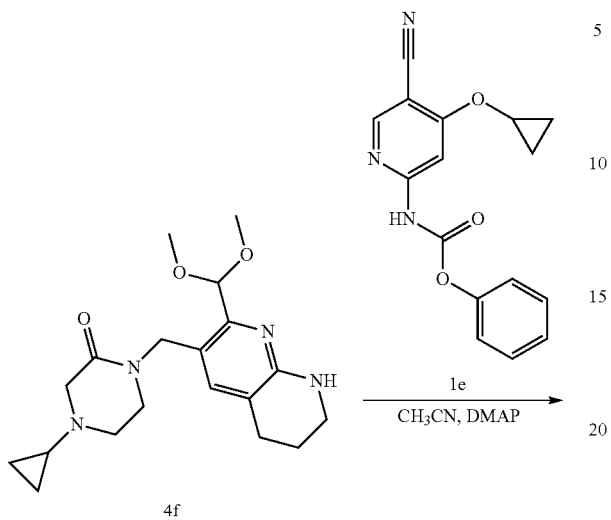

4f

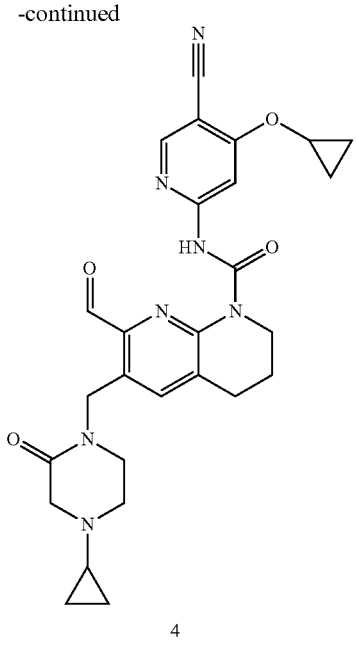

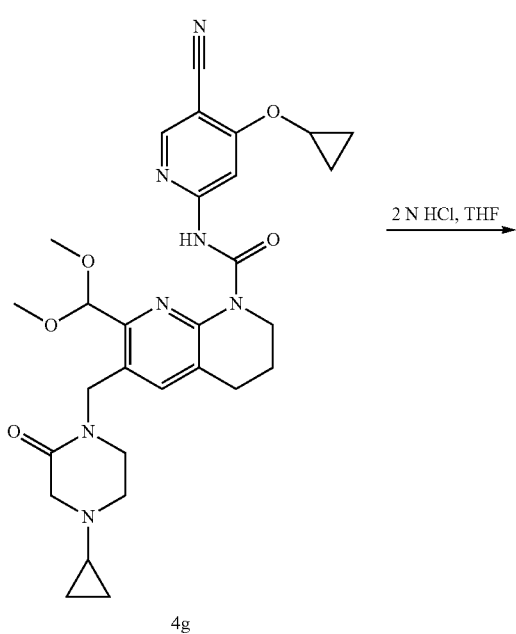

4g

Compound 4a (2 g, 10 mmol) was dissolved in THF (100 mL), and ethyl 2-bromoacetate (1.67 g, 10 mmol) and Et$_3$N (3.03 g, 30 mmol) were added at 0° C. The reaction was warmed to room temperature, and stirred for 16 hours. Water (200 mL) was added and extracted with CH$_2$Cl$_2$ (100 mL×3), the combined organic phase was washed with brine (100 mL×2), dried over Na$_2$SO$_4$ and filtered. The filtrate was concentrated in vacuo, the residue was purified via column chromatography (CH$_2$Cl$_2$/MeOH=10/1) to afford compound 4c (1.3 g, yield 45%).

Compound 4c (1.3 g, 4.5 mmol) was added to HCl (4M dioxane solution, 10 mL) slowly, and the resulting mixture was stirred at room temperature for 16 hours, the reaction solution was concentrated to afford compound 4d (0.78 g, yield: 95%) as an oil.

Compound 4d (100 mg, 0.423 mmol) and 4e (202 mg, 0.846 mmol) were dissolved in 1,2-dichloroethane, and sodium triacetoborohydride (372 mg, 0.846 mmol), MgSO$_4$ (510 mg, 4.23 mmol) and DIPEA (109 mg, 0.846 mmol). The reaction mixture was stirred at room temperature for 16 hours. The reaction solution was concentrated, the residue was purified via column chromatography (CH$_2$Cl$_2$/MeOH=10/1) to afford compound 4f (120 mg, yield 78%).

Compound 1e (5 mg, 0.017 mmol), 4f (6 mg, 0.017 mmol) and DMAP (2 mg, 0.017 mmol) were dissolved in CH$_3$CN (2 mL). The reaction mixture was stirred at 60° C. for 2 hours. TLC showed the completion of the reaction. The reaction mixture was concentrated in vacuo, the residue was purified via preparative TLC (CH$_2$Cl$_2$/MeOH=20/1) to afford compound 4g (3 mg, yield 30%) as a yellow solid. MS 562.2 [M+M]$^+$.

Compound 4g (3 mg, 0.005 mmol) was dissolved in THF (2 mL), HCl (2 N, 0.5 mL) was added, the reaction mixture was stirred at room temperature for 1 hour. The reaction was concentrated, the residue was purified via preparative TLC (CH$_2$Cl$_2$/MeOH=20/1) to afford compound 4 (1 mg, yield 30%) as a white solid. $^1$H NMR (400 MHz, CDCl$_3$): δ 13.89 (s, 1H), 10.24 (s, 1H), 8.35 (s, 1H), 8.27 (s, 1H), 7.66 (s, 1H), 5.06 (s, 2H), 4.11-4.08 (m, 2H), 4.01-3.97 (m, 1H), 3.38 (s, 2H), 3.32-3.30 (m, 2H), 2.95-2.92 (m, 2H), 2.88-2.85 (m, 2H), 2.06-2.03 (m, 2H), 1.65-1.63 (m, 1H), 0.95-0.86 (m, 4H), 0.52-0.50 (m, 2H), 0.48-0.45 (m, 2H); MS 516.2[M+H]$^+$.

Example 5. Preparation of Compound 5

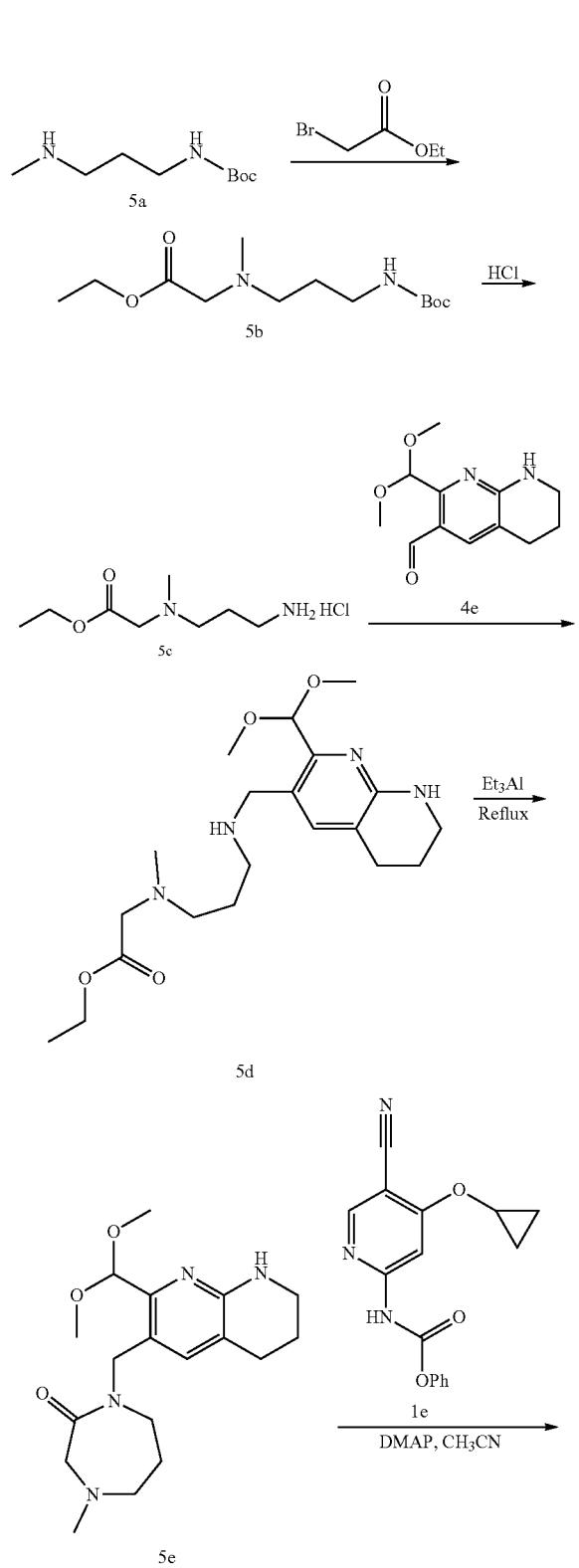

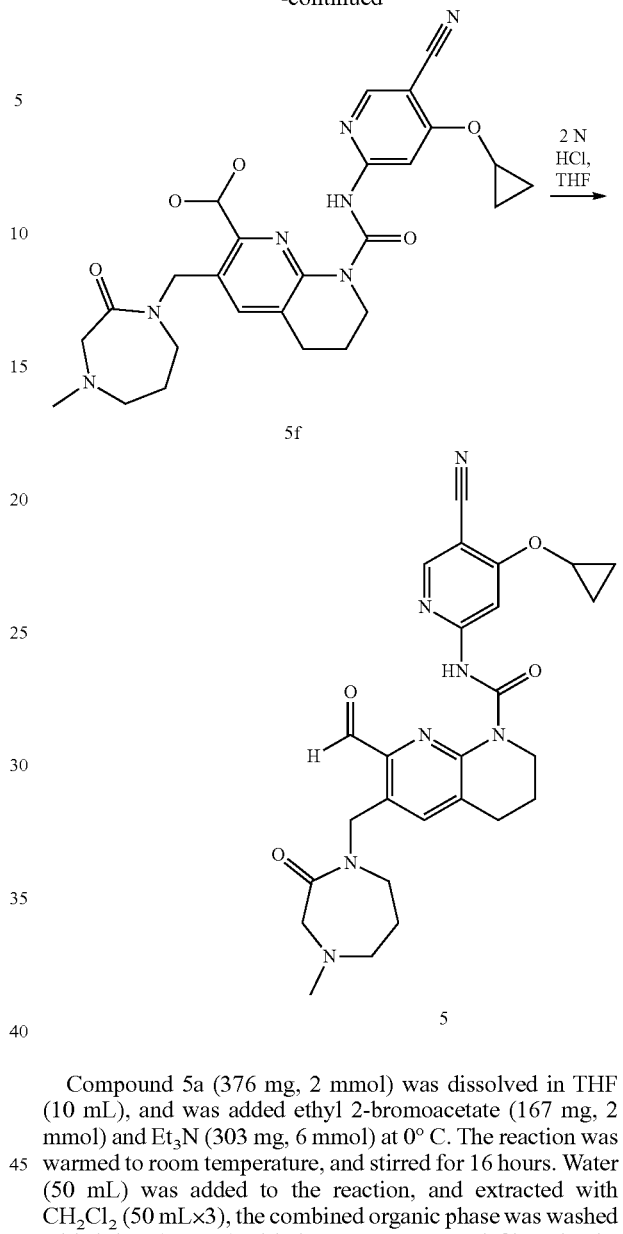

Compound 5a (376 mg, 2 mmol) was dissolved in THF (10 mL), and was added ethyl 2-bromoacetate (167 mg, 2 mmol) and Et$_3$N (303 mg, 6 mmol) at 0° C. The reaction was warmed to room temperature, and stirred for 16 hours. Water (50 mL) was added to the reaction, and extracted with CH$_2$Cl$_2$ (50 mL×3), the combined organic phase was washed with brine (50 mL), dried over Na$_2$SO$_4$ and filtered. The filtrate was concentrated in vacuo, the residue was purified via column chromatography (CH$_2$Cl$_2$/MeOH=10/1) to afford 5b (520 mg, yield 94%). MS 275.2 [M+H]$^+$.

Compound 5b (520 mg, 1.9 mmol) was added to HCl (4 M dioxane solution, 5 mL), and was stirred at room temperature for 16 hours. The reaction mixture was concentrated to afford compound 5c (385 mg, yield 96%) as a white solid. MS 175.2 [M+H]$^+$.

Compound 5c (285 mg, 1.36 mmol) and 4e (481 mg, 2.04 mmol) was dissolved in 1,2-dichlororethane (50 mL), and was added sodium triacetoborohydride (601 mg, 2.72 mmol), MgSO$_4$ (1.632 g, 13.6 mmol) and DIPEA (351 mg, 2.72 mmol). The reaction mixture was stirred at room temperature for 16 hours. The reaction solution was concentrated, the residue was purified via column chromatography (petroleum ether/EtOAC=1/2) to afford 5d (225 mg, yield 42%). MS 395.2 [M+H]$^+$.

Compound 5d (120 mg, 0.3 mmol) was dissolved in toluene (2 mL), and Et$_3$Al (1 M toluene solution, 0.6 mL)

was added, the reaction mixture was refluxed for 2 hour under the N₂ atmosphere. The reaction was cooled to room temperature, quenched with 0.5 mL water, and concentrated, the resulting crude product was purified via preparative TLC (CH$_2$Cl$_2$/MeOH=20/1) to afford compound 5e (35 mg, yield 33%) as a yellow solid. MS 349.2 [M+H]⁺.

Compound 5e (40 mg, 0.12 mmol), 1e (36 mg, 0.12 mmol) and DMAP (15 mg, 0.12 mmol) was dissolved in CH$_3$CN (2 mL), the reaction was stirred 3 hours at 50° C. TLC showed the reaction was complete. The reaction mixture was concentrated in vacuo, the residue was purified via preparative TLC (CH$_2$Cl$_2$/MeOH=20/1~15/1) to afford compound 5f (2 mg, yield 3%) as a white solid. MS 550.3 [M+H]⁺.

Compound 5f (2 mg, 0.0036 mmol) was dissolved in THF (0.5 mL), and HCl (2 N, 5 drops) was added, the reaction mixture was stirred at room temperature for 1 hour. The reaction was poured into saturated aq. NaHCO$_3$, extracted with EtOAc three times, the combined organic layers were washed with brine, dried over Na$_2$SO$_4$ and filtered. The filtrate was concentrated in vacuo, the residue was purified via preparative TLC (acetone/CH$_2$Cl$_2$=1/1) to afford compound 5 (1.7 mg, yield 93%) as a pale white solid. ¹H NMR (400 MHz, CDCl$_3$): δ 13.91 (s, 1H), 10.24 (s, 1H), 8.35 (s, 1H), 8.28 (s, 1H), 7.69 (s, 1H), 5.06 (s, 2H), 4.14-4.06 (m, 2H), 4.03-3.97 (m, 1H), 3.51 (s, 2H), 3.49-3.42 (m, 2H), 2.98-2.90 (m, 2H), 2.89-2.81 (m, 2H), 2.45 (s, 3H), 2.10-1.99 (m, 2H), 1.82-1.70 (m, 2H), 0.99-0.90 (m, 4H); MS 504.2 [M+H]⁺.

Example 6. Preparation of Compound 6

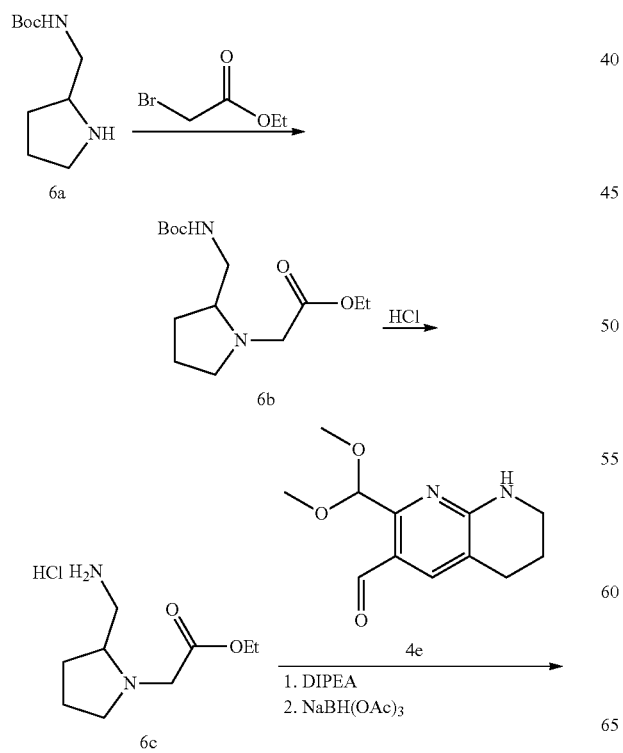

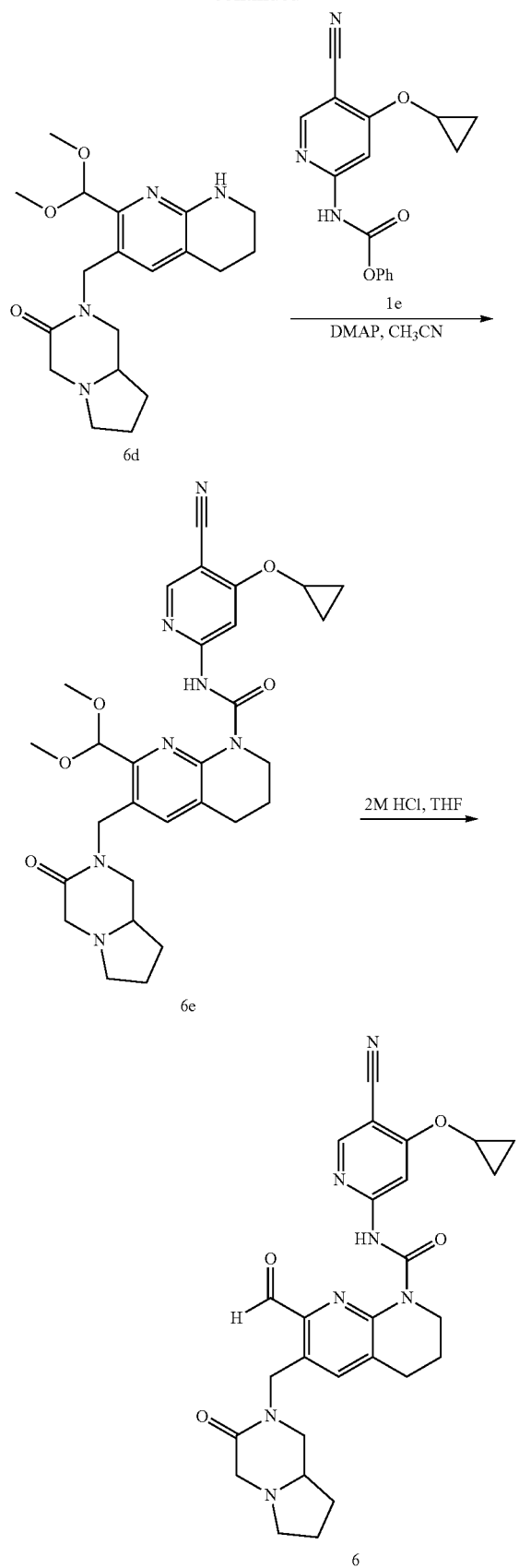

Compound 6a (200 mg, 1 mmol) was dissolved in THF (10 mL), and added ethyl 2-bromoacetate (167 mg, 1 mmol) and Et₃N (303 mg, 3 mmol) at 0° C. The reaction was warmed to room temperature, and stirred for 16 hours. The reaction was added water (50 mL) and extracted with CH₂Cl₂ (50 mL×3), the combined organic phase was washed with brine (50 mL), dried over Na₂SO₄ and filtered, The filtrate was concentrated in vacuo, the residue was purified via column chromatography (CH₂Cl₂/MeOH=10/1) to afford compound 6b (250 mg, yield 87%). MS 287.2 [M+H]⁺.

Compound 6b (250 mg, 0.87 mmol) was added to HCl (4M dioxane solution, 5 mL), and was stirred at room temperature for 16 hours. The reaction mixture was concentrated to afford compound 6c (180 mg, yield 93%) as a white solid. MS 187.2 [M+H]⁺.

Compound 6c (180 mg, 0.81 mmol), 4e (290 mg, 1.22 mmol) was dissolved in 1,2-dichlororethane (20 mL), and was added sodium triacetoborohydride (358 mg, 1.62 mmol), MgSO₄ (972 mg, 8.1 mmol) and DIPEA (209 mg, 1.62 mmol). The reaction mixture was stirred at room temperature for 16 hours. The reaction solution was concentrated, the residue was purified via column chromatography (CH₂Cl₂/MeOH=10/1) to afford compound 6d (145 mg, yield 50%). MS 361.2 [M+H]⁺.

Compound 6d (50 mg, 0.14 mmol), 1e (42 mg, 0.14 mmol) and DMAP (17 mg, 0.14 mmol) was dissolved in CH₃CN (2 mL), the reaction was heated to 50° C. under stirring for 3 hours. The reaction mixture was concentrated in vacuo, the residue was purified via preparative TLC (CH₂Cl₂/MeOH=20/1) to afford compound 6e (1.0 mg, yield 3%) as a white solid. MS 562.3 [M+H]⁺.

Compound 6e (2 mg, 0.0036 mmol) was dissolved in THF (0.5 mL), and HCl (2 N, 0.5 mL) was added, the reaction mixture was stirred at room temperature for 2 hours. The reaction was poured into saturated aq. NaHCO₃, extracted with EtOAc three times, the combined organic phase was washed with brine, dried over Na₂SO₄ and filtered. The filtrate was concentrated in vacuo, the residue was purified via preparative TLC (CH₂Cl₂/MeOH=20/1 first purification, and CH₂Cl₂/Acetone=1/3 second purification) to afford compound 6 (1 mg, yield 55%) as a white solid. ¹H NMR (400 MHz, CDCl₃): δ 13.90 (s, 1H), 10.25 (s, 1H), 8.35 (s, 1H), 8.28 (s, 1H), 7.66 (s, 1H), 5.18 (d, J=15.6 Hz, 1H), 5.02 (d, J=16.0 Hz, 1H), 4.12-4.07 (m, 2H), 4.03-3.97 (m, 1H), 3.79 (d, J=16.4 Hz, 1H), 3.39 (dd, J=11.2 Hz, 3.6 Hz, 1H), 3.21-3.12 (m, 2H), 3.01 (d, J=16.0 Hz, 1H), 2.96-2.91 (m, 2H), 2.44-2.41 (m, 1H), 2.20-2.13 (m, 1H), 2.08-2.01 (m, 2H), 2.00-1.84 (m, 3H), 1.52-1.41 (m, 1H), 0.99-0.93 (m, 4H); MS 516.2 [M+H]⁺.

Example 7. Preparation of Compound 7

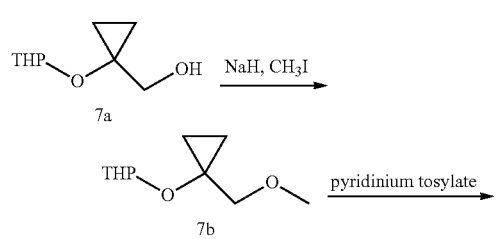

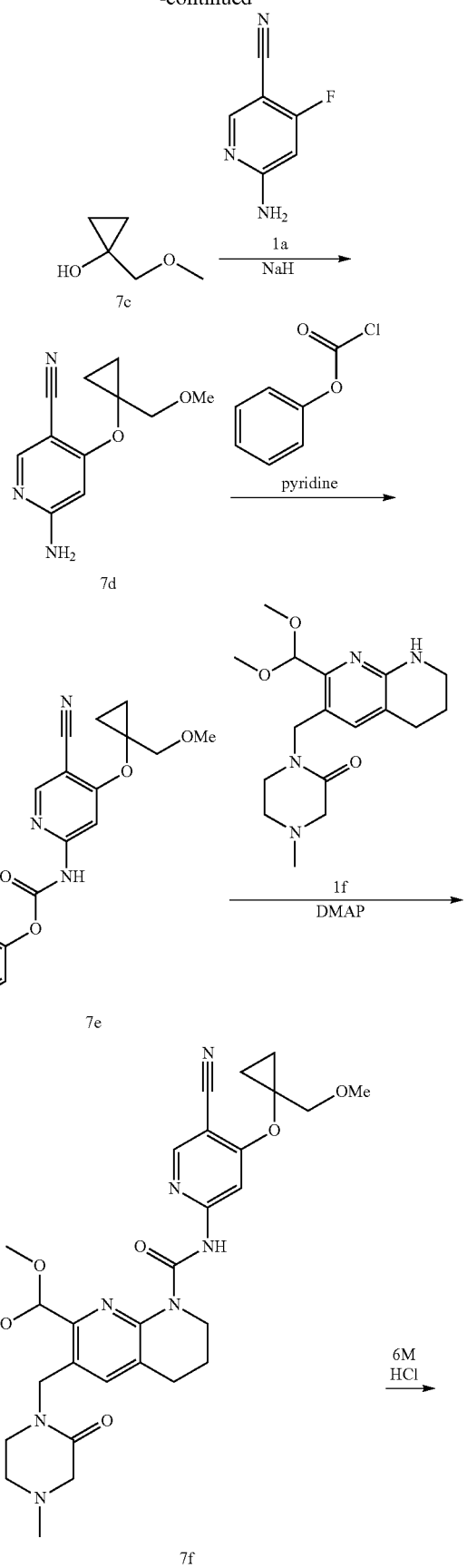

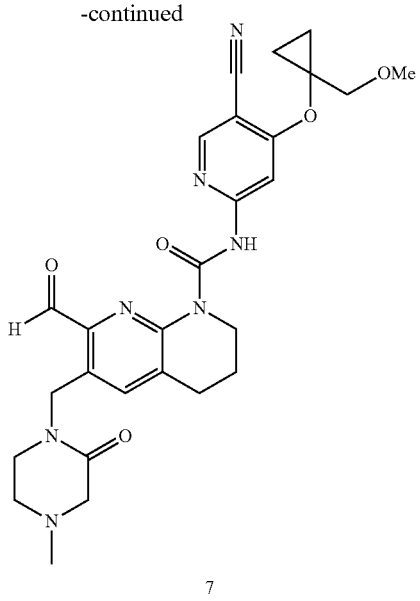

7

Compound 7a (1.8 g, 10.47 mmol) was dissolved in THF (20 mL) and 60% NaH (628 mg, 15.70 mmol) and MeI (2.97 g, 20.94 mmol) were added, the reaction was stirred at room temperature for 2.5 hours. The reaction was poured into ice-water, and extracted with EtOAc (100 mL×3), the combined organic phase was washed with brine (100 mL), dried over Na₂SO₄ and filtered. The filtrate was concentrated in vacuo, the crude product was purified via column chromatography (petroleum ether/EtOAC=0~15%) to afford compound 7b (1.8 g, yield 92%) as a colorless oil.

Compound 7b (0.6 g, 3.23 mmol) and PPTS (40 mg, 0.16 mmol) was dissolved in MeOH (15 mL), the reaction was stirred under reflux for 1.5 hours. The reaction was cooled to room temperature, and concentrated. Et₂O (100 mL) and water (50 mL) was added to the residue. The separated organic phase was washed with brine (50 mL), dried over Na₂SO₄, filtered, and concentrated under reduced pressure to afford compound 7c (330 mg, yield 99%) as a colorless oil. $^1$H NMR (400 MHz, CDCl₃): δ 3.45 (s, 2H), 3.43 (s, 3H), 0.85-0.82 (m, 2H), 0.59-0.56 (m, 2H).

Compound 7c (300 mg, 2.94 mmol) was dissolved in dry THF (15 mL), and 60% NaH (155 mg, 3.88 mmol) was added, the reaction was stirred at room temperature for 40 minutes. Compound 1a (201 mg, 1.47 mmol) was then added to the above solution, the resulting mixture was stirred at room temperature for 16 hours. TLC indicated the reaction was complete. The reaction was poured into saturated aq. NH₄Cl (20 mL), and extracted with EtOAc (25 mL×3), the combined organic phase was washed with brine, dried over Na₂SO₄, filtered, concentrated. The crude product was purified via column chromatography (EtOAC/petroleum ether=55~100%) to afford compound 7d (140 mg, yield 44%) as a white solid. MS 220.1 [M+H]⁺.

Compound 7d (210 mg, 0.96 mmol) and pyridine (151 mg, 1.92 mmol) was dissolved in dry CH₂Cl₂, and phenyl chloroformate (180 mg, 1.15 mmol) was added under stirring and temperature was controlled at 0° C. After addition was complete, the reaction mixture was stirred at room temperature for 16 hours. TLC showed the reaction was complete. The reaction was added to water (50 mL), extracted with EtOAc (100 mL×3), the combined organic phase was washed with brine, dried over Na₂SO₄ and filtered. The filtrate was concentrated, and the residue was purified via column chromatography (EtOAC/petroleum ether=0~25%) to afford compound 7e (200 mg, yield 61%) as a white solid. MS 340.0 [M+H]⁺.

Compound 7e (180 mg, 0.53 mmol), 1f (70 mg, 0.21 mmol) and DMAP (64 mg, 0.52 mmol) were dissolved in CH₃CN (6 mL), the reaction was stirred 40 minutes at 100° C. The reaction was cooled to room temperature, and was concentrated in vacuo. The residue was purified via column chromatography (MeOH/CH₂Cl₂=0~10%) to afford compound 7f (130 mg) as a yellow solid, which was used for next step directly. MS 580.3 [M+H]⁺.

Compound 7f (130 mg) was dissolved in dry THF (4 mL), and HCl (6 N, 4 mL) was added, the reaction mixture was stirred at room temperature for 16 hours. The reaction was poured into saturated aq. NaHCO₃ (20 mL), extracted with EtOAc (50 mL×3), the combined organic phase was washed with brine, dried over Na₂SO₄ and filtered. The filtrate was concentrated in vacuo, the residue was purified via preparative TLC (CH₂Cl₂/MeOH=20/1) to afford compound 7 (7.1 mg, two steps yield 6%) as a yellow solid. $^1$H NMR (400 MHz, DMSO-d₆): δ 13.83 (s, 1H), 10.10 (s, 1H), 8.60 (s, 1H), 8.23 (s, 1H), 7.61 (s, 1H), 4.93 (s, 2H), 3.98-4.01 (m, 2H), 3.69 (s, 2H), 3.29 (s, 3H), 3.27-3.24 (m, 4H), 2.97-2.93 (m, 2H), 2.55-2.48 (m, 2H), 2.53 (s, 3H), 1.96-1.93 (m, 2H), 1.10-1.05 (m, 4H); MS 534.2 [M+H]⁺.

Example 8. Preparation of Compound 8

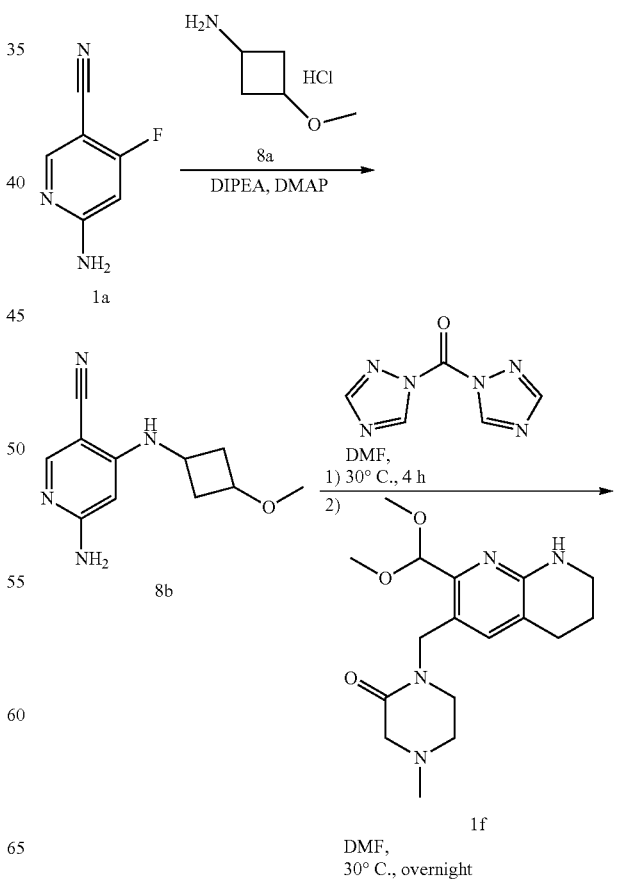

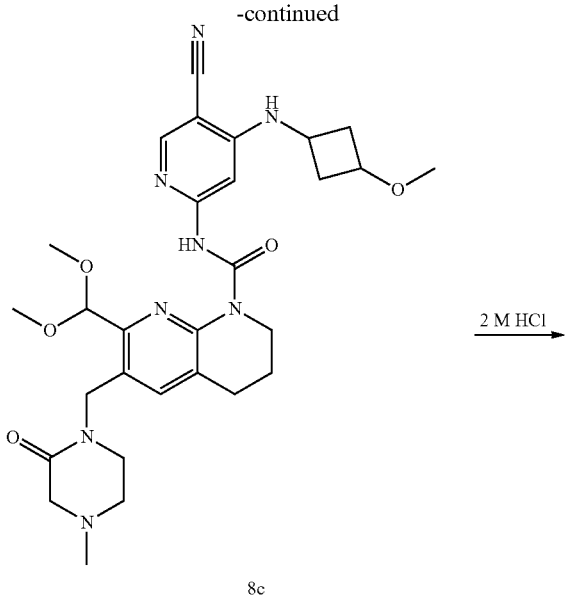

8c

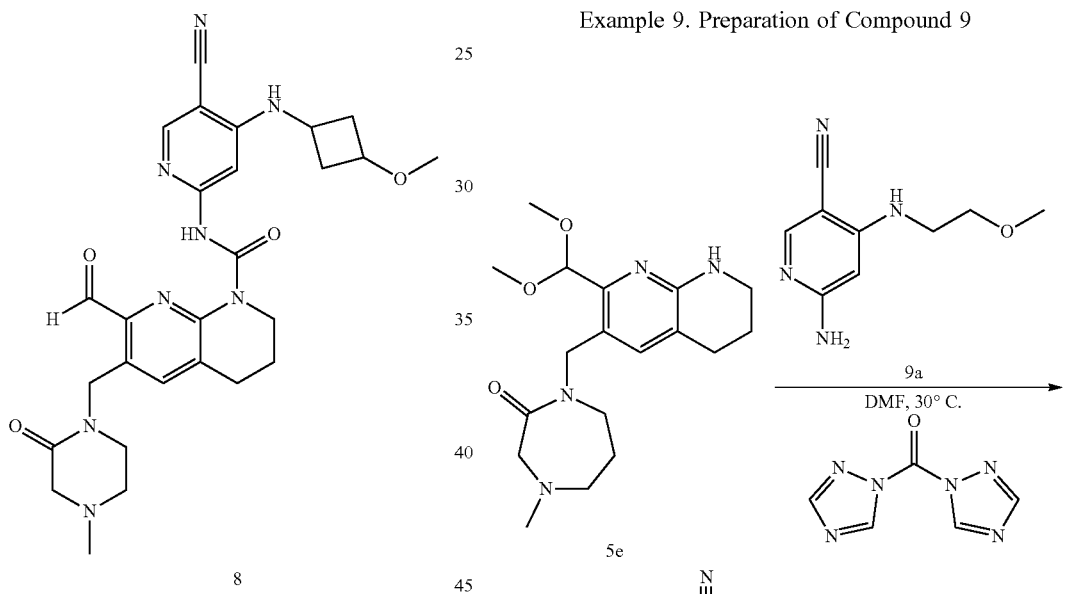

vacuo, the residue was purified via preparative TLC (CH₂Cl₂/MeOH=20:1) to afford compound 8c (9 mg, yield 8%) as a pale-white solid. MS 579.4 [M+H]⁺.

Compound 8c (9 mg, 0.016 mmol) was dissolved in THF (1 mL), and HCl (2 M aqueous solution, 0.2 mL) was added at room temperature. The reaction mixture was stirred at room temperature for 3 hours. It was poured into saturated aq. NaHCO₃ (5 mL), extracted with CH₂Cl₂ (10 mL×3), the combined organic phase was washed with brine, dried over Na₂SO₄, and filtered. The filtrate was concentrated in vacuo, the crude product was purified via preparative TLC (petroleum ether/CH₂Cl₂=15/1), then further purified via preparative TLC (CH₂Cl₂/MeOH/acetone=20/1/1) to afford compound 8 (1.3 mg, yield 16%) as a pale solid. ¹H NMR (400 MHz, CDCl₃-d₆): δ 13.61 (s, 1H), 10.23 (s, 1H), 8.18 (s, 1H), 7.62 (s, 1H), 7.49 (s, 1H), 5.09 (s, 2H), 5.05 (d, J=6.0 Hz, 1H), 4.10-4.06 (m, 2H), 3.80-3.71 (m, 2H), 3.35 (t, J=5.4 Hz, 2H), 3.27 (s, 3H), 3.19 (s, 2H), 2.99-2.90 (m, 4H), 2.65 (t, J=5.6 Hz, 2H), 2.35 (s, 3H), 2.06-2.00 (m, 2H), 1.95-1.87 (m, 2H); MS 533.3 [M+H]⁺.

Example 9. Preparation of Compound 9

Compound 1a (150 mg, 1.095 mmol), 3-methoxycyclobutan-1-amine hydrochloride (150 mg, 1.095 mmol) and DIPEA (423 mg, 3.285 mmol) were added into DMF (3 mL) one by one, the resulting mixture was stirred at 50° C. overnight. The LCMS indicated the reaction was complete. Aqueous LiCl solution was added to the reaction, then the mixture was extracted with EtOAc (10 mL×3). The combined organic phase was washed with brine, dried over Na₂SO₄ and filtered. The filtrate was concentrated in vacuo, the residue was purified via preparative TLC (CH₂Cl₂/MeOH=25:1) to afford compound 8b (140 mg, yield 59%) as a white solid. MS 219.2 [M+H]⁺.

Compound 8b (43 mg, 0.197 mmol) and CDI (97 mg, 0.592 mmol) were dissolved in dry DMF (2 mL). The reaction mixture was stirred at 30° C. for 4 hours, then was cooled to room temperature, and was added 1f (46 mg, 0.138 mmol). The reaction was stirred at 30° C. overnight, and was quenched with ice-water, extracted with EtOAc (10 mL×3). The combined organic layers were washed with brine, dried over Na₂SO₄ and filtered. The filtrate was concentrated in

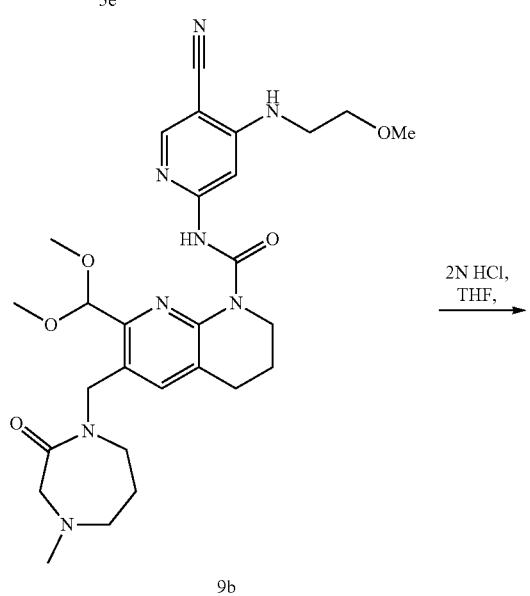

9b

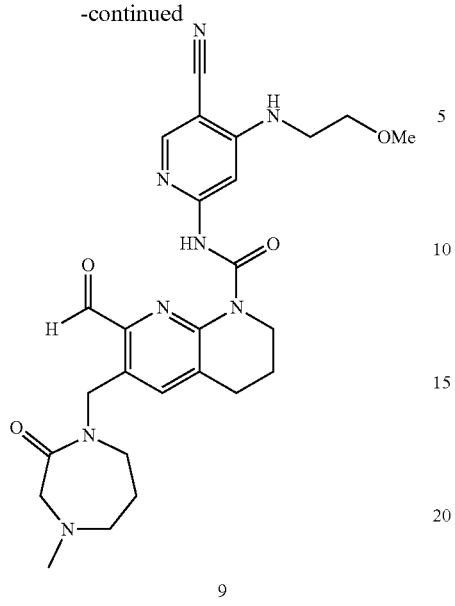

9

Compound 9a (74 mg, 0.38 mmol) and CDI (187 mg, 1.14 mmol) were dissolved in dry DMF (3 mL), the mixture was stirred at 30° C. for 4 hours. After the mixture was cooled to room temperature, compound 5e (80 mg, 0.23 mmol) was added. The reaction mixture was stirred at 30° C. overnight. The reaction was quenched with ice-water, extracted with EtOAc (10 mL×3), the combined organic phase was washed with brine, dried over Na$_2$SO$_4$ and filtered. The filtrate was concentrated in vacuo, the residue was purified via preparative TLC (CH$_2$Cl$_2$/MeOH=20:1) to afford compound 9b (15 mg, yield 12%) as a yellow solid. MS 567.4 [M+H]$^+$.

Compound 9b (15 mg, 0.026 mmol) was dissolved in THF (1.0 mL), HCl (2 M aqueous solution, 0.2 mL) was added under ice bath cooling, the resulting mixture was stirred at room temperature for 3 hours. The pH was adjusted to 9 by using saturated aq. NaHCO$_3$, then the mixture was extracted with CH$_2$Cl$_2$ (2 mL×5). The combined organic phase was washed with brine, dried over Na$_2$SO$_4$ and filtered. The filtrate was concentrated in vacuo, the crude product was purified via preparative TLC (CH$_2$Cl$_2$/methanol=15/1) to afford compound 9 (7.2 mg, yield 52%) as a white solid. $^1$H NMR (400 MHz, DMSO-d$_6$): δ 13.50 (s, 1H), 10.07 (s, 1H), 8.27 (s, 1H), 7.61 (s, 1H), 7.52 (s, 1H), 6.99 (t, J=5.6 Hz, 1H), 4.87 (s, 2H), 3.99-3.95 (m, 2H), 3.53 (t, J=5.6 Hz, 2H), 3.48-3.35 (m, 6H), 3.29 (s, 3H), 2.95-2.90 (m, 2H), 2.82-2.75 (m, 2H), 2.31 (s, 3H), 1.97-1.89 (m, 2H), 1.66-1.60 (m, 2H); MS 521.3 [M+H]$^+$.

Example 10. Preparation of Compound 10

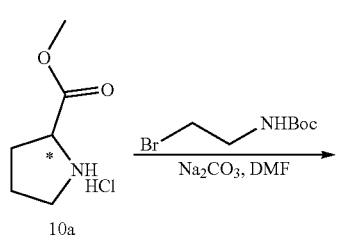

10a

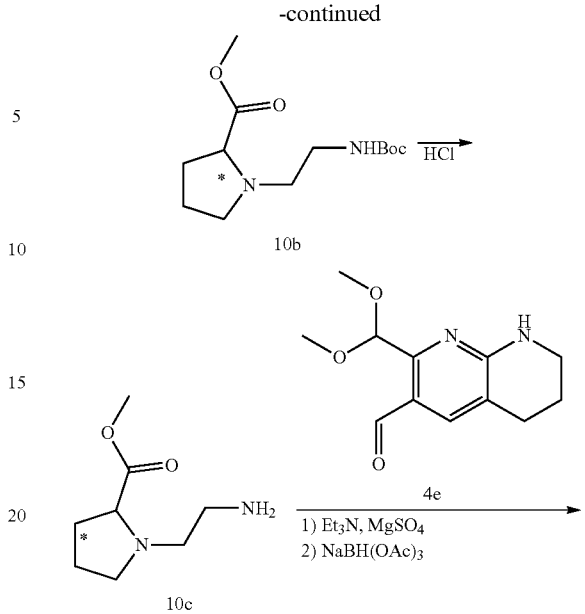

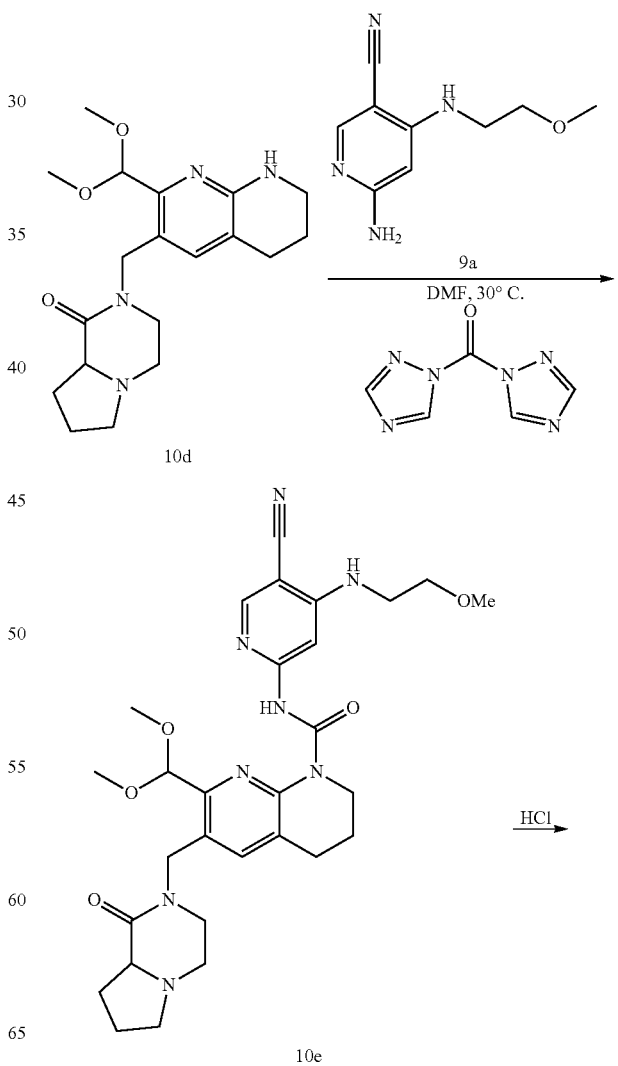

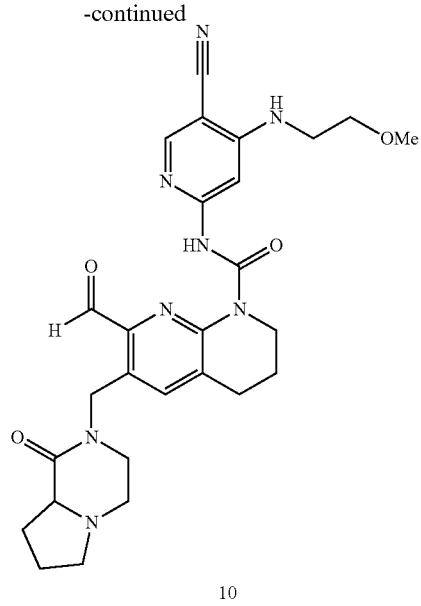

10

Methyl prolinate hydrochloride (2.9 g, 17.5 mmol), tert-butyl (2-bromoethyl) carbamate (4.7 g, 21.0 mmol) and Na$_2$CO$_3$ (5.6 g, 52.8 mmol) were mixed in DMF (40 mL), the mixture was stirred at 40° C. overnight. The reaction solution was poured into ice-water, and extracted with EtOAc (100 mL×3), the combined organic phase was washed with brine, dried over Na$_2$SO$_4$ and filtered. The filtrate was concentrated in vacuo, the crude product was purified by column chromatography (petroleum ether/EtOAC=2/1)) to afford compound 10b (3.5 g, yield 73%) as a light yellow oil. MS 273.2 [M+H]$^+$.

Compound 10b (1.0 g, 1.82 mmol) was dissolved in dry dioxane (10 mL), then was added HCl (4 M dioxane solution, 10 mL), the reaction mixture was stirred at room temperature overnight, and was concentrated in vacuo to afford compound 10c (900 mg, yield 99%) as a yellow solid.

Compound 4e (450 mg, 1.90 mmol) and compound 10c (900 mg, 3.67 mmol) were dissolved in 1,2-dichloroethane (15 mL), MgSO$_4$ (4 g) and Et$_3$N (960 mg, 9.50 mmol) was added. The reaction was stirred at room temperature for 6 hours. Sodium triacetoborohydride (1.2 g, 5.66 mmol) was added, and the mixture was stirred at room temperature for 16 hours. The mixture was poured into saturated aq. Na$_2$CO$_3$, and extracted with EtOAc (100 mL×3), the combined organic phase was washed with brine, dried over Na$_2$SO$_4$ and filtered. The filtrate was concentrated in vacuo, the residue was purified via column chromatography (CH$_2$Cl$_2$/MeOH=50/1~25/1) to afford compound 10d (120 mg, yield 18%) as yellow oil. MS 361.2 [M+H]$^+$.

Compound 9a (60 mg, 0.31 mmol) and CDI (153 mg, 0.93 mmol) was dissolved in dry DMF (3 mL), the mixture was stirred at 30° C. for 4 hours, then was cooled to room temperature, and compound 10d (67 mg, 0.19 mmol) was added. The reaction mixture was stirred at 30° C. overnight. The reaction was quenched with ice-water, extracted with EtOAc (50 mL×3), the combined organic phase was washed with brine, dried over Na$_2$SO$_4$ and filtered. The filtrate was concentrated in vacuo, the residue was purified via preparative TLC (CH$_2$Cl$_2$/MeOH=20:1) to afford compound 10e (22 mg, yield 20%) as a yellow solid. MS 579.4 [M+H]$^+$.

Compound 10e (20 mg, 0.035 mmol) was dissolved in THF (1.0 mL), followed by addition of HCl (2M aqueous solution, 0.2 mL) under ice bath cooling, the resulting mixture was stirred at room temperature for 3 hours. The pH value of the reaction solution was adjusted to 9 by using saturated aq. NaHCO$_3$, which was extracted with CH$_2$Cl$_2$ (2 mL×5), the combined organic phase was washed with brine, dried over Na$_2$SO$_4$ and filtered. The filtrate was concentrated in vacuo, and the crude product was purified via preparative TLC (CH$_2$Cl$_2$/MeOH=15:1) to afford compound 10 (10.1 mg, yield 55%) as a white solid. $^1$H NMR (400 MHz, DMSO-d$_6$): δ 13.49 (s, 1H), 10.08 (s, 1H), 8.28 (s, 1H), 7.54 (s, 1H), 7.53 (s, 1H), 6.99 (t, J=5.6 Hz, 1H), 4.97 (d, J=16.4 Hz, 1H), 4.78 (d, J=16.4 Hz, 1H), 4.01-3.94 (m, 2H), 3.53 (t, J=5.6 Hz, 2H), 3.48-3.36 (m, 2H), 3.29 (s, 3H), 3.25-3.16 (m, 2H), 3.02-2.77 (m, 4H), 2.77-2.67 (m, 1H), 2.10-1.88 (m, 4H), 1.83-1.67 (m, 4H); MS 533.3 [M+H]$^+$.

Example 11. Preparation of Compound 11

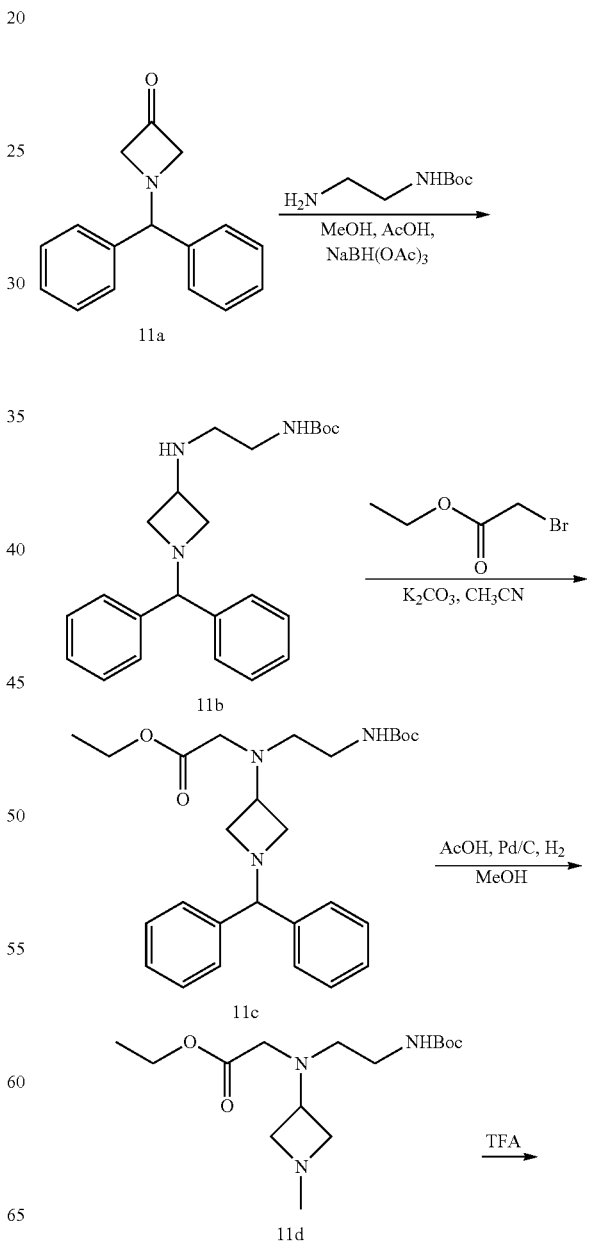

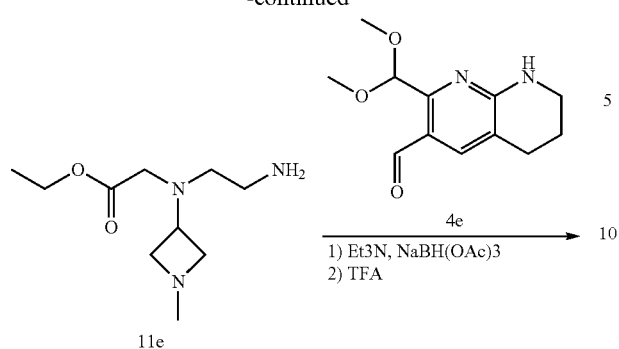
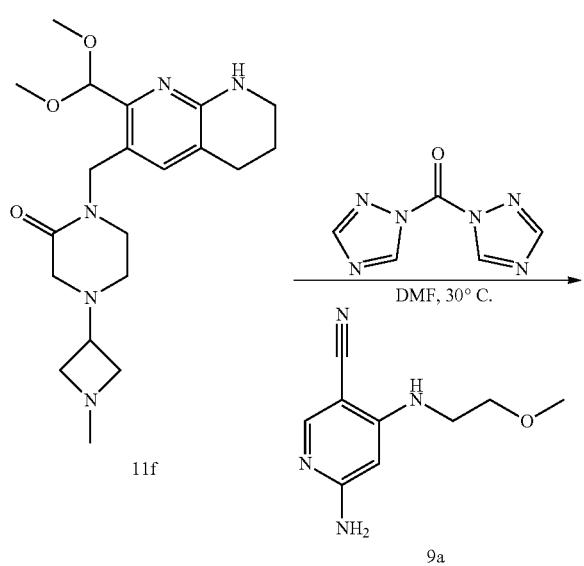
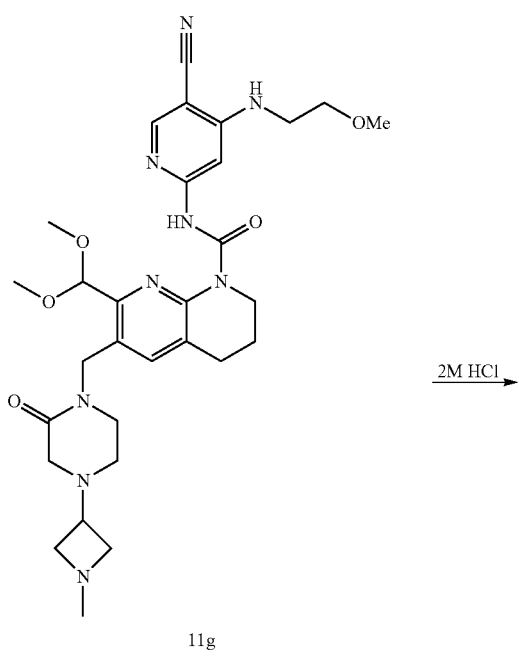
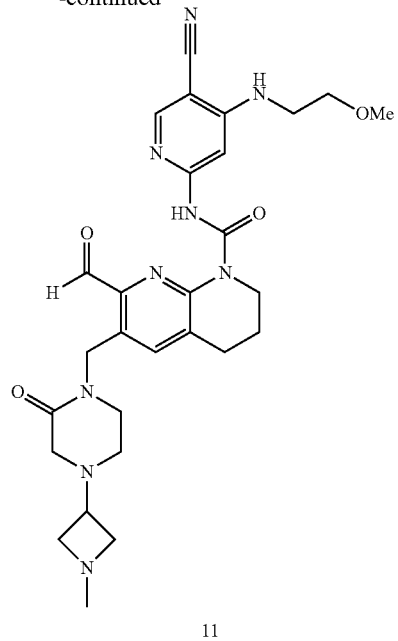

1-Benzhydrylazetidin-3-one (3 g, 12.66 mmol), tert-butyl (2-aminoethyl) carbamate (2.43 g, 15.19 mmol) and actyl acid (0.912 g, 15.19 mmol) were dissolved in MeOH (100 mL). The reaction mixture was stirred at room temperature for 2 hours, followed by the addition of sodium triacetoborohydride (2.39 g, 37.97 mmol). It was stirred at room temperature for 3 hours. LCMS indicated the reaction was finished. Appropriate amount of ice-water was added, and the mixture was extracted with EtOAc (200 mL×3), the combined organic phase was washed with brine (200 mL), dried over $Na_2SO_4$. After filtering, the filtrate was concentrated in vacuo, the resulting residue was purified via column chromatography (petroleum ether/EAOAc=3/1 to 0:1) to afford compound 11b (4.07 g, yield 84%) as a light yellow solid. MS 382.3 $[M+H]^+$.

Compound 11b (4.07 g, 10.68 mmol), ethyl 2-bromoacetate (2.14 g, 12.82 mmol) and $K_2CO_3$ (2.95 g, 21.36 mmol) were added one by one to $CH_3CN$ (160 mL), the resulting mixture was stirred at 50° C. overnight. Upon completion indicated by LCMS, the reaction mixture was cooled to room temperature, and filtered. The filtrate was added some ice-water, extracted with EtOAc (150 mL×3), the combined organic phase was washed with brine (200 mL), dried over $Na_2SO_4$ and filtered. The filtrate was concentrated in vacuo, the residue was purified via column chromatography (petroleum ether/EtOAc=1/11) to afford compound 11c (2.9 g, yield 58%) as a yellow solid. MS 468.3 $[M+M]^+$.

Compound 11c (1.9 g, 4.07 mmol), acetic acid (244 mg, 4.07 mmol), formaldehyde (37%)(990 mg, 12.21 mmol) and Pd/C (10%, 200 mg) were added sequentially to MeOH (120 mL), the reaction system was exchange with $H_2$ three times. and was stirred overnight at room temperature and under $H_2$ atmosphere. The LCMS showed the reaction was finished. Upon completion indicated by LCMS, the reaction mixture was filtered, and the filtrate was concentrated in vacuo to afford crude product compound 11d (1.6 g, yield 99%, which was used for next step directly without further purification). MS 316.3 $[M+H]^+$.

Compound 11d (crude 1.6 g, 4.07 mmol) was dissolved in $CH_2Cl_2$ (10 mL), and TFA (5 mL) was added. The reaction solution was stirred at room temperature for 2 hours. Upon completion indicated by LCMS, the reaction mixture was concentrated in vacuo to afford crude product compound 11e (1.4 g, yield 99%, which was used in the next step without further purification) as a light yellow oil. MS 216.2 [M+H]⁺.

Compound 4e (120 mg, 0.508 mmol), compound 11e (122 mg, 1.017 mmol), Et₃N (205 mg, 2.034 mmol) and MgSO₄ (1 g) were added sequentially to 1,2-dichloroethane (6 mL), the reaction mixture was stirred at room temperature for 6 hours, followed by addition of sodium triacetoborohydride (323 mg, 1.525 mmol). The reaction was stirred at room temperature overnight. TLC showed the reaction was completed. Saturated aq. Na₂CO₃ was added to the above mixture, and was extracted with EtOAc three times (25 mL). The combined organic phase was washed with brine (25 mL) and filtered, dried over MgSO₄. The filtrate was concentrated in vacuo, the residue was purified via preparative TLC (CH₂Cl₂/MeOH=10/1) to afford compound 11f (100 mg, yield 51%) as a colorless oil. ¹H NMR (400 MHz, DMSO-d₆): δ 6.94 (s, 1H), 6.50 (s, 1H), 5.02 (s, 1H), 4.52 (s, 2H), 3.40-3.35 (m, 3H), 3.29 (s, 6H), 3.27-3.20 (m, 2H), 3.09-3.04 (m, 2H), 2.97 (s, 2H), 2.89-2.83 (m, 2H), 2.66-2.61 (m, 2H), 2.50-2.45 (m, 2H), 2.23 (s, 3H), 1.80-1.70 (m, 2H).

Compound 11f (70 g, 0.365 mmol) and CDI (179 mg, 1.094 mmol) were dissolved in dry DMF (3 mL), and was heated to 30° C. while stirring for 4 hours. The mixture was cooled to room temperature, a solution of compound 9a (100 mg, 0.257 mmol) in dry DMF (1 mL) was added. The reaction mixture was stirred at 30° C. overnight. The reaction was quenched with ice-water, extracted with EtOAc twice (10 mL), the aqueous layer was purified via preparative HPLC to afford compound 11g (10 mg, yield 6%) as a white solid. MS 608.4 [M+H]⁺.

Compound 11g (10 mg, 0.016 mmol) was dissolved in THF (2 ml), HCl (2 M aqueous solution, 0.2 mL) was added at room temperature. The mixture was stirred at room temperature for 3 hours. LCMS showed the reaction was complete. Its pH value of the reaction solution was adjusted to 7-8 by using saturated aq. NaHCO₃, the reaction solution was concentrated in vacuo, the residue was purified via preparative TLC (CH₂Cl₂/MeOH=8:1) to afford compound 11 (4.6 mg, yield 50%) as a pale-white solid. ¹H NMR (400 MHz, CDCl₃): δ 13.59 (s, 1H), 10.23 (s, 1H), 8.18 (s, 1H), 7.65 (s, 1H), 7.57 (s, 1H), 5.34-5.25 (m, 1H), 5.08 (s, 2H), 4.12-4.03 (m, 2H), 3.64 (t, J=5.0 Hz, 2H), 3.60-3.52 (m, 2H), 3.53-3.45 (m, 2H), 3.42 (s, 3H), 3.36 (t, J=5.2 Hz, 2H), 3.12 (s, 2H), 3.10-3.00 (m, 3H), 2.96-2.90 (m, 2H), 2.60-2.54 (m, 2H), 2.42 (s, 3H), 2.09-1.98 (m, 2H); MS 562.4 [M+H]⁺.

Example 12. Preparation of Compound 12

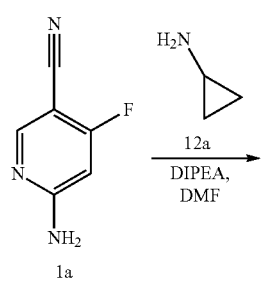

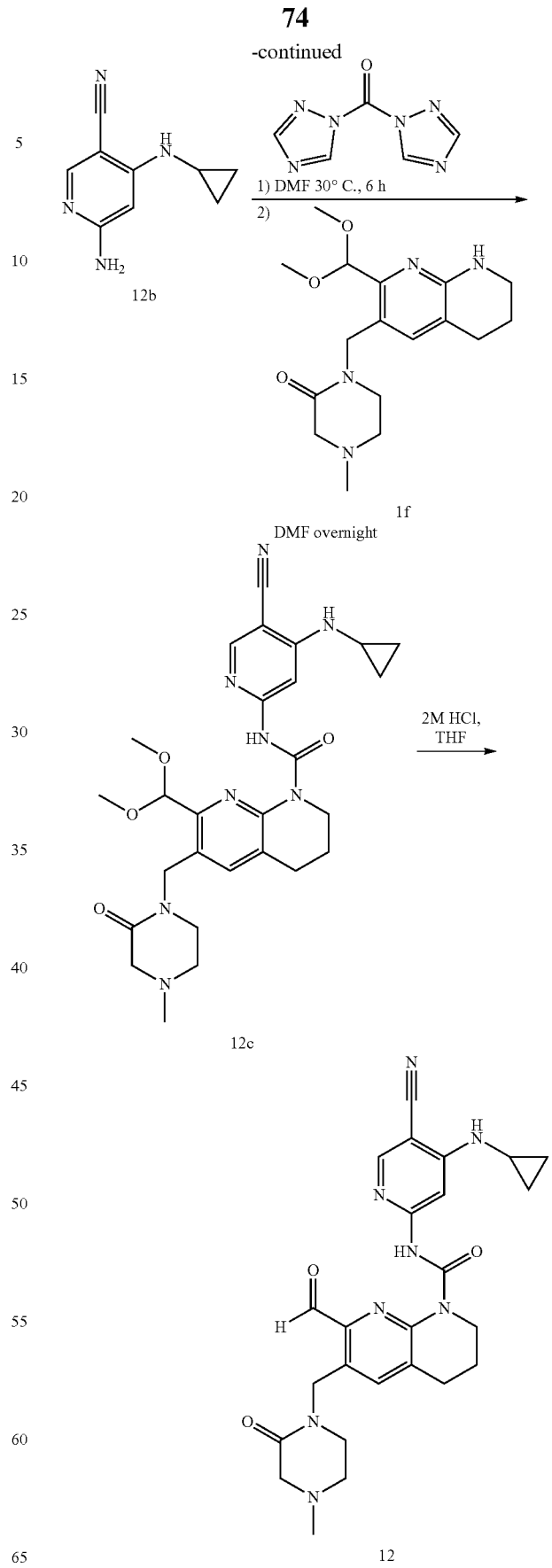

Compound 1a (127 mg, 0.93 mmol), cyclopropanamine (12a, 212 mg, 3.70 mmol) were added to DMF (3 mL), the reaction was stirred at 60° C. overnight. The LCMS results showed the reaction was finished. The reaction was poured into water, extracted with EtOAc (10 mL×3), the combined organic phase was washed by brine, dried over $Na_2SO_4$ and filtered, The filtrate was concentrated in vacuo, the residue was purified via preparative TLC ($CH_2Cl_2$/MeOH=50:1) to afford compound 12b (110 mg, yield 68%) as a white solid. MS 175.2 $[M+H]^+$.

Compound 12b (40 mg, 0.23 mmol) and CDI (113 mg, 0.69 mmol) were dissolved was dissolved in dry DMF (2 mL), the mixture was stirred at room temperature for 4 hours, and 1f (77 mg, 0.23 mmol) was added. The reaction mixture was stirred at room temperature overnight, then the reaction was quenched with ice-water, extracted with $CH_2Cl_2$ (10 mL×3), the combined organic phase was washed with brine (10 mL), dried over $Na_2SO_4$ and filtered. The filtrate was concentrated in vacuo, the residue was purified via preparative TLC ($CH_2Cl_2$/MeOH=20:1) to afford compound 12c (20 mg, yield 16%) as a pale solid. MS 535.3 $[M+H]^+$.

Compound 12c (11 mg, 0.021 mmol) was dissolved in THF (2 mL), then HCl (2 M aqueous solution, 0.7 mL) was added at room temperature, the mixture was stirred at room temperature for 3 hours. The reaction solution was poured into appropriate amount of saturated aq. $NaHCO_3$, extracted with $CH_2Cl_2$ (10 mL), the combined organic phase was washed with brine, dried over $Na_2SO_4$ and filtered. The filtrate was concentrated in vacuo, the residue was first purified via preparative TLC ($CH_2Cl_2$/MeOH=15:1), then was purified again via preparative TLC ($CH_2Cl_2$/MeOH=20:1) to afford compound 12 (5.3 mg, yield 53%) as a pale solid. $^1$HNMR (400 MHz, $CDCl_3$): δ 13.62 (s, 1H), 10.24 (s, 1H), 8.18 (s, 1H), 7.92 (s, 1H), 7.62 (s, 1H), 5.27 (s, 1H), 5.09 (s, 2H), 4.15-4.05 (m, 2H), 3.35 (t, J=5.6 Hz, 2H), 3.20 (s, 2H), 2.92 (t, J=6.4 Hz, 2H), 2.69-2.61 (m, 3H), 2.35 (s, 3H), 2.09-1.98 (m, 2H), 1.00-0.92 (m, 2H), 0.73-0.52 (m, 2H); MS 489.3 $[M+H]^+$.

Example 13. Preparation of Compound 13

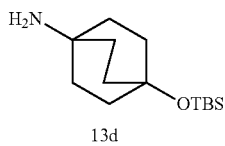

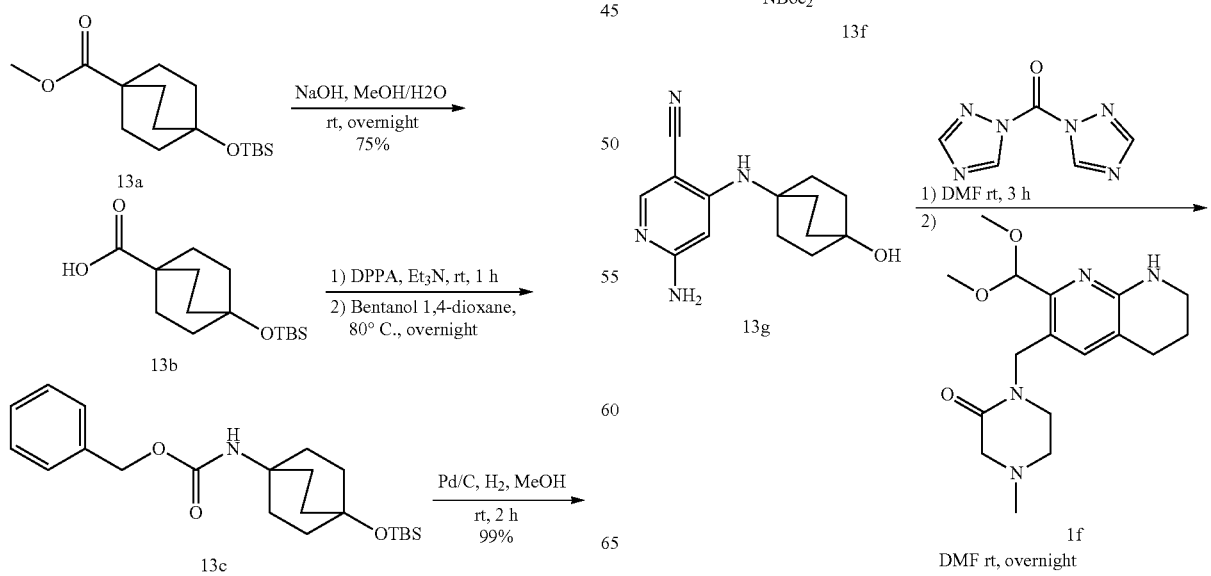

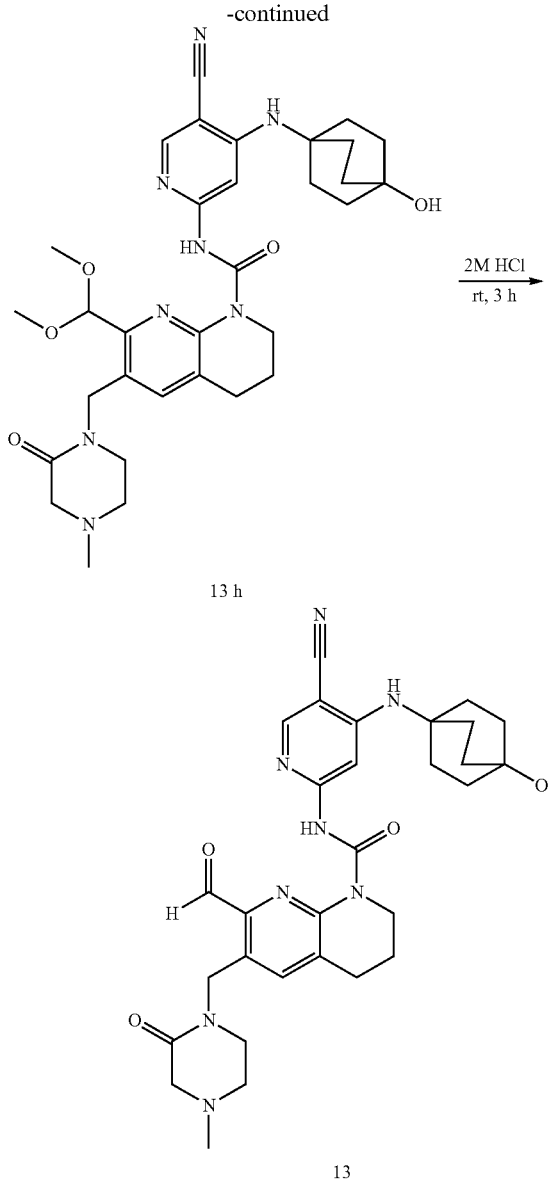

13h

13 the residue was purified via preparative TLC (petroleum ether/EtOAC=90/1) to afford compound 13c (500 mg, yield 94%) as a light yellow solid. MS 390.3 [M+Na]$^+$.

Compound 13c (300 mg, 0.771 mmol) and Pd/C (10%, 30 mg) were added sequentially to MeOH (30 mL), the reaction was exchanged with $H_2$ three times under stirring at room temperature, then was stirred for 2 h under $H_2$ (1 atm) atmosphere. LCMS showed the reaction was complete. The reaction was concentrated in vacuo to afford compound 13d (200 mg, yield 99%) as a colorless oil. The crude product was used for next step directly. MS 256.4 [M+Na]$^+$.

Compound 1a (100 mg, 0.730 mmol) and (Boc)$_2$O (477 mg, 2.190 mmol) were dissolved in dry THF (10 mL), DMAP (8.9 mg, 0.073 mmol) was then added. The reaction solution was stirred at room temperature for 1.5 hours, LCMS showed the reaction was complete. The reaction solution was poured into appropriate amount of water, extracted with EtOAc (10 mL×3), the combined organic phase was washed with brine, dried over $Na_2SO_4$ and filtered. The filtrate was concentrated in vacuo, the residue was purified via preparative TLC (petroleum ether/EtOAC=7/1) to afford compound 13e (226 mg, yield 92%) as a white solid. MS 360.2 [M+Na]$^+$.

Compound 13e (204 mg, 0.605 mmol), compound 13d (154 mg, 0.605 mmol) and DIPEA (156 mg, 1.211 mmol) were added sequentially to dry DMF (5 mL), the reaction was heated to 80° C. overnight while stirring. LCMS showed the reaction was complete. The reaction solution was cooled to room temperature, appropriate amount of water was added, then extracted with EtOAc (10 mL×3). The combined organic layers were washed with brine, dried over $Na_2SO_4$ and filtered. The filtrate was concentrated in vacuo, the residue was purified via preparative TLC (petroleum ether/EtOAC=8/1) to afford compound 13f (250 mg, yield 72%) as a white solid. $^1$H NMR (400 MHz, CDCl$_3$): δ 8.24 (s, 1H), 6.90 (s, 1H), 4.78 (s, 1H), 2.06-1.97 (m, 6H), 1.90-1.79 (m, 6H), 1.49 (s, 18H), 0.84 (s, 9H), 0.07 (s, 6H). MS 573.3 [M+H]$^+$.

Compound 13f (250 mg, 0.437 mmol) was dissolved in dry CH$_2$Cl$_2$ (5 mL), TFA (5 mL) was added, the reaction was stirred at room temperature for 2 hours, LCMS showed the reaction was complete. The reaction was poured into appropriate amount of saturated aq. NaHCO$_3$ (5 mL), extracted with EtOAc (10 mL×3), the combined organic layers were washed with brine, dried over $Na_2SO_4$ and filtered. The filtrate was concentrated in vacuo, the crude product was purified via preparative TLC CH$_2$Cl$_2$/MeOH=18/1) to afford compound 13g (102 mg, yield 90%) as a white solid. MS 259.2 [M+H]$^+$.

Compound 13g (40 mg, 0.155 mmol) and CDI (76 mg, 0.465 mmol) were dissolved in dry DMF (1.5 mL). The reaction mixture was stirred at room temperature for 3 hours, and was added 1f (41 mg, 0.124 mmol). The reaction was stirred at room temperature overnight. It was quenched with ice-water, extracted with EtOAc (10 mL×3), the combined organic phase was washed with brine, dried over $Na_2SO_4$ and filtered. The filtrate was concentrated in vacuo, the residue was purified via preparative TLC (CH$_2$Cl$_2$/MeOH=20:1~30:1) to afford compound 13h (17 mg, yield 18%) as a white solid. MS 619.4 [M+M]$^+$.

Compound 13h (15 mg, 0.024 mmol) was dissolved in THF (3 mL), HCl (2 M aqueous solution, 2 mL) was added at room temperature. The mixture was stirred at room temperature for 3 hours. The reaction solution was poured into appropriate amount of saturated aq. NaHCO$_3$, extracted with EtOAc (10 mL×3), the combined organic phase was washed by brine, dried over $Na_2SO_4$ and filtered, The filtrate Compound 13a (605 mg, 2.030 mmol) was dissolved in MeOH/THF/H$_2$O mixture solution (20 mL), NaOH (162 mg, 4.06 mmol) was added, followed by stirring at room temperature overnight. Upon the completion indicated by LCMS, the pH value of the reaction solution was adjusted to 5 by using HCl (4 N aqueous solution). It was extracted with EtOAc (10 mL×3). The combined organic phase was washed with brine, dried over $Na_2SO_4$ and filtered. The filtrate was concentrated in vacuo to afford compound 13b (430 mg, yield 75%) as a light yellow solid. Compound 13b (390 mg, 1.373 mmol), Et$_3$N (300 mg, 2.970 mmol) and DPPA (566 mg, 2.060 mmol) were added sequentially to dry dioxane (4 mL), the reaction solution was stirred at room temperature for 1.5 hours, then was added benzyl alcohol (3 mL), the reaction solution was stirred at 80° C. overnight. LCMS showed the reaction was complete. The reaction was cooled to room temperature, and concentrated. The residue was poured into water, extracted with EtOAc (10 mL×3), the combined organic phase was washed with brine, dried over $Na_2SO_4$ and filtered. The filtrate was concentrated in vacuo, was concentrated in vacuo, the residue was purified via preparative TLC (EtOAc/acetone=1/1; then CH$_2$Cl$_2$/MeOH=20:1~15/1) to afford compound 13 (5 mg, yield 36%) as a white solid. 573.3 [M+H]$^+$.

Example 14. Preparation of Compound 14

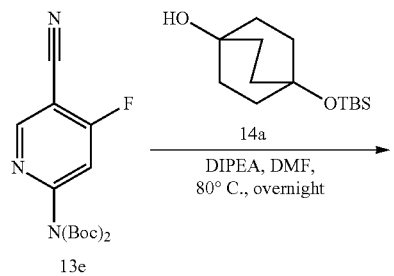

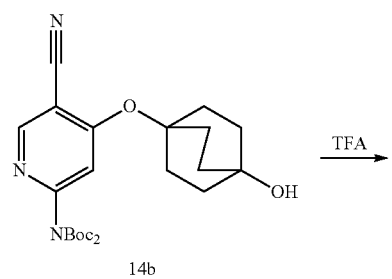

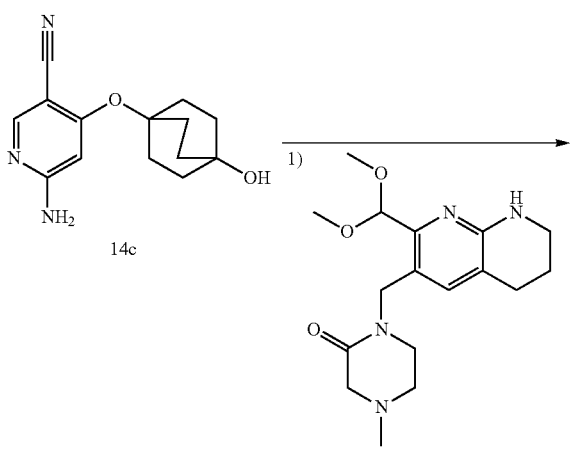

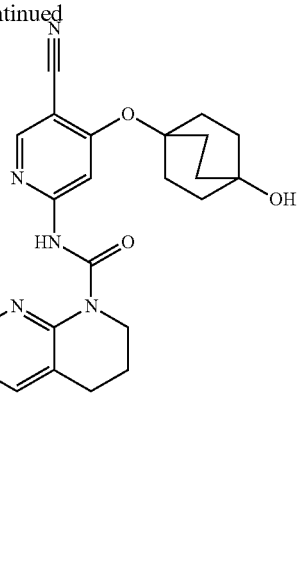

Compound 14a was prepared according to the reference method (1) *Journal of the American Chemical Society*, 1970, 92(6), 1582-6; (2) *Helvetica Chimica Acta*, 1979, 62(8), 2802-16. Compound 14a reacted with compound 13b to afford compound 14b, which was deprotected under acidic condition to afford compound 14c. Compound 14c reacted with compound 1f to afford urea, then was deprotected under acidic condition to afford compound 14. Refer to the preparation of compound 13 for detailed procedure. MS 574.2 [M+H]$^+$.

Example 15

1. FGFR1 and FGFR4 Kinase Activity Inhibition Experiments

The FGFR1, FGFR2, FGFR3 and FGFR4 protein kinase activities were determined using the Caliper mobility shift assay. The compound was dissolved in DMSO and diluted with kinase buffer, and 5 □L of a 5-fold final concentration of the compound (10% DMSO) was added to a 384-well plate. After adding 10 □L of 2.5-fold enzyme (FGFR1 and FGFR4, respectively) solution, incubate for 10 minutes at room temperature, and then add 10 □L of a (FAM-labeled peptide and ATP) solution. Incubate at 28° C. for 30-60 minutes and stop the reaction by adding 25 □L stop solution. Conversion rate data was read on a Caliper EZ Reader II (Caliper Life Sciences). The conversion rate was converted into inhibition rate data (% inhibition rate=(max−sample conversion rate)/(max−min)*100). Wherein max is the conversion of the DMSO control and min is the conversion of the enzyme-free control. Plot the curve with the compound concentration and inhibition rate on the horizontal and vertical coordinates, and fit the curve and calculate the IC$_{50}$ using XLFit excel add-in version 4.3.1 software.

The results indicate that most of the tested compounds of formula I of the invention have a strong inhibitory effect on FGFR4 kinase activity (IC$_{50}$ less than 20 nM), at the same time, the inhibition of FGFR1 kinase activity was weak, and the activities of some representative compounds are shown in Table 1.

TABLE 1

| | FGFR kinase inhibition (IC$_{50}$, nM) | |
| --- | --- | --- |
| | FGFR4 | FGFR1 |
| Compound 1 | <5 | >10,000 |
| Compound 2 | <5 | >10,000 |
| Compound 3 | <20 | |
| Compound 4 | <20 | |
| Compound 5 | <5 | |
| Compound 6 | <5 | |
| Compound 7 | <20 | |
| Compound 8 | <5 | |
| Compound 9 | <5 | |
| Compound 10 | <5 | |
| Compound 11 | <5 | |
| Compound 12 | <5 | |

2. Compound Inhibition Test on Huh-7 Tumor Cell Proliferation

The Huh7 cell suspension was adjusted to 5×10e4/mL or 2×10e4/mL with DMEM+2 Mm Glutamine+10% FBS medium. A 100 μL cell suspension was added to each well in a 96-well cell culture plate at a final cell concentration of 5000 cells/well (72 hours) or 2000 cells/well (168 hours). The test compound was dissolved in DMSO as a 10 mM stock solution. Compounds at a final concentration of 200× were prepared using stock solutions and DMSO, and 3× serial dilutions were prepared and then diluted 20-fold with each medium. Finally, 10 μL of the corresponding 10-fold solution was added to each well of each cell, and each drug concentration was single-well. The final concentrations of each compound were 3000 nM, 1000 nM, 333.3 nM, 111.1 nM, 37.04 nM, 12.35 nM, 4.12 nM, 1.37 nM, and the final concentration of DMSO per well was 0.5%. Incubate for 72 or 168 hours in a 37° C., 5% $CO_2$ incubator. After 72 or 168 hours of drug treatment, according to the CTG instructions, add 100 □L CellTiter Glo detection reagent per well, pre-melt and equilibrate to room temperature CTG solution, mix with a microplate shaker for 2 minutes, and leave at room temperature for 10 minutes. The chemiluminescence signal value was then measured using an EnSpire plate reader. Cell survival rate was calculated using formula: $(V_{sample}-V_{blank})/(V_{vehicle\ control}-V_{blank})\times 100\%$. $V_{sample}$ is the reading of the drug treatment group, $V_{vehicle}$ control is the average value of the solvent control group, and $V_{blank}$ is the average value of the blank control well. The S-type dose-survival curve was plotted and the $IC_{50}$ values were calculated using the GraphPad Prism 5.0 software using a non-linear regression model. The activity of some representative compounds is shown in Table 2

TABLE 2

| Inhibition of Huh7 tumor cell proliferation (IC$_{50}$, nM) | |
| --- | --- |
| | Huh7 |
| Compound 1 | <50 |
| Compound 2 | <50 |
| Compound 3 | <50 |
| Compound 4 | <500 |
| Compound 5 | <50 |
| Compound 6 | <500 |
| Compound 7 | <500 |

All documents mentioned in the present application are incorporated herein by references as if each document is individually incorporated thereby. In addition, it should be understood that various changes and modifications may be made by those skilled in the art in the form of the appended claims.

The invention claimed is:
1. A compound of formula (I), or the pharmaceutically acceptable salts, prodrugs, deuterated derivatives, hydrates, or solvates thereof:

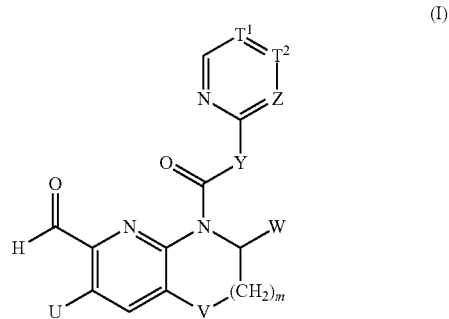

wherein:
$T^1$ is N or $CR^1$, wherein $R^1$ is selected from the group consisting of hydrogen, halogen, $C_{1-6}$ alkyl, $C_{3-6}$ cycloalkyl, cyano, $CO_2NH_2$, halogenated $C_{1-4}$ alkyl and hydroxy substituted $C_{1-4}$ alkyl;
$T^2$ is N or $CR^2$, wherein $R^2$ is selected from the group consisting of hydrogen, halogen, $C_{1-4}$ alkyl, $C_{1-4}$ alkoxy, hydroxy substituted $C_{1-4}$ alkoxy, $C_{2-4}$ alkenyl, $C_{2-4}$ alkyl, $CHR^3R^4$, cyano, $CO_2NH_2$, $C_{1-4}$ alkoxy substituted $C_{1-4}$ alkyl, $C_{1-4}$ alkoxy substituted $C_{1-4}$ alkoxy, $C_{1-4}$ alkoxy substituted halogen $C_{1-4}$ alkoxy, $C_{1-4}$ alkoxy substituted $C_{2-4}$ alkenyl, $C_{1-4}$ alkoxy substituted $C_{2-4}$ alkynyl, $C_{1-4}$ alkylthiol, bis($C_{1-4}$ alkyl)amino substituted $C_{1-4}$ alkoxy, $O(CR^7R^8)_n$—$R^6$, $NR^5(CR^7R^8)_n$—$R^6$, and halogenated $C_{1-4}$ alkoxy which is optionally substituted by hydroxy;
$R^3$ and $R^4$ together with the carbon atom to which they are attached form a 4- to 7-membered heterocyclic group containing one or two heteroatoms selected from N, O or S, wherein the heterocyclic group is optionally substituted by one or two $X^1$; each $X^1$ is independently selected from the group consisting of halogen, $C_{1-4}$ alkyl, hydroxy, $C_{3-8}$ cycloalkyl, 4- to 8-membered heterocyclic, $C_{1-4}$ alkoxy, $C_{1-4}$ alkoxy substituted $C_{1-4}$ alkoxy, $C(O)C_{1-4}$ alkyl, cyano, $CO_2NH_2$, amino, $C_{1-4}$ alkylamino, bis($C_{1-4}$ alkyl)amino, and =O;
$R^5$ is hydrogen or $C_{1-4}$ alkyl;
$R^6$ is $C_{1-4}$ alkyl, hydroxy substituted $C_{1-4}$ alkyl, $C_{2-4}$ alkenyl, $C_{2-4}$ alkynyl, $C_{2-4}$ alkynyl substituted $C_{1-4}$ alkyl, $C_{3-12}$ cycloalkyl, $C_{3-8}$ cycloalkyl substituted $C_{1-4}$ alkyl, 4- to 12-membered heterocyclic group having 1 to 3 heteroatoms selected from N, O and S, 4- to 12-membered heterocyclic substituted $C_{1-4}$ alkyl, 6-membered aryl, 6-membered aryl substituted $C_{1-4}$ alkyl, 5- to 6-membered heteroaryl, 5- to 6-membered heteroaryl substituted $C_{1-4}$ alkyl, halogenated $C_{1-4}$ alkyl, $C_{1-4}$ alkoxy substituted $C_{1-4}$ alkyl, halogenated $C_{1-4}$ alkoxy substituted $C_{1-4}$ alkyl, or bis ($C_{1-4}$ alkyl) amino substituted $C_{1-4}$ alkyl, wherein the alkyl, alkenyl, alkynyl, cycloalkyl, heterocyclic group, aryl, and heteroaryl are optionally substituted with 1 to 3 $X^2$; each $X^2$ is independently selected from the group consisting of hydrogen, halogen, $C_{1-4}$ alkyl, hydroxy, $C_{1-4}$ alkoxy, $C_{3-8}$ cycloalkyl, 4- to 8-membered heterocyclic group, $C_{1-4}$ alkoxy substituted $C_{1-4}$ alkyl, $C_{1-4}$ alkoxy substituted $C_{1-4}$ alkoxy, $C(O)C_{1-4}$ alkyl, $C(O)OC_{1-4}$ alkyl, $OC(O)C_{1-4}$ alkyl, amino, $C_{1-4}$ alkylamino, bis (C$_{1-4}$ alkyl) amino, and =O; wherein the C3-12 cycloalkyl includes monocyclic, bridged, spiro, and fused cycloalkyl; the 4- to 12-membered heterocyclic group includes monocyclic, bridged, spiro, and fused heterocyclic group;

or R$^5$ and R$^6$ together with the nitrogen atom to which they are attached form a 4- to 12-membered heterocyclic group which optionally contains one or two additional heteroatoms selected from N, O or S, wherein the heterocyclic group is optionally substituted by one or more X$^3$; each X$^3$ is independently selected from the group consisting of hydrogen, halogen, C$_{1-4}$ alkyl, hydroxy, C$_{1-4}$ alkoxy, C$_{3-8}$ cycloalkyl, 4- to 8-membered heterocyclic, C$_{1-4}$ alkyoxy substituted C$_{1-4}$ alkoxy, C(O)C$_{1-4}$ alkyl, amino, C$_{1-4}$ alkylamino, bis (C$_{1-4}$ alkyl) amino, bis (C$_{1-4}$ alkyl) amino substituted C$_{1-4}$ alkyl, and =O;

R$^7$ and R$^8$ are each independently hydrogen, C$_{1-4}$ alkyl or halogen;

Z is CH or N; wherein, when T$^1$ is N, then T$^2$ and Z are other than N; when T$^2$ is N, then T$^1$ and Z are other than N; when Z is N, then T$^1$ and T$^2$ are other than N;

Y is NR or O; wherein R is hydrogen or C$_{1-4}$ alkyl;

W is hydrogen or C$_{1-4}$ alkyl;

V is CH$_2$;

U is selected from the group consisting of

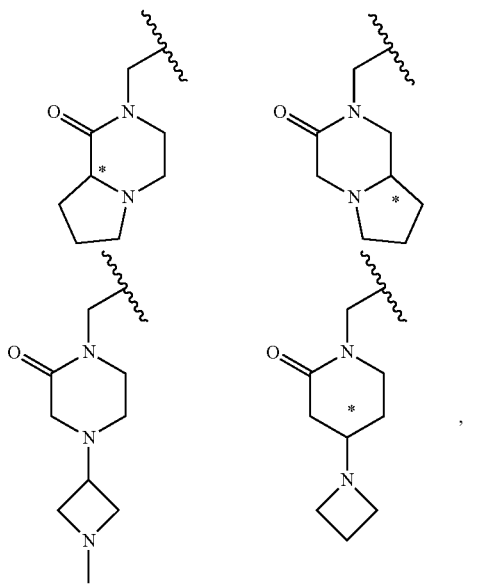

m is 1; and
n is 0, 1, 2, or 3.

2. The compound of claim 1, wherein,
T$^1$ is CR$^1$; and/or
T$^2$ is CR$^2$; and/or
Z is CH; and/or
Y is NH; and/or
W is hydrogen.

3. The compound of claim 1, wherein R$^1$ is CN.

4. The compound according to claim 1 wherein R$^2$ is NR$^5$(CR$^7$R$^8$)$_n$—R$^6$ or O(CR$^7$R$^8$)$_n$—R$^6$; wherein R$^5$ is hydrogen or C$_{1-4}$ alkyl; R$^6$ is C$_{2-4}$ alkenyl, C$_{2-4}$ alkynyl, C$_{2-4}$ alkynyl substituted C$_{1-4}$ alkyl, C$_{3-12}$ cycloalkyl, C$_{3-8}$ cycloalkyl substituted C$_{1-4}$ alkyl, 4- to 12-membered heterocyclic group containing 1 to 3 hetero atoms selected from N, O and S, 4- to 12-membered heterocyclic substituted C$_{1-4}$ alkyl, 6-membered aryl, 6-membered aryl substituted C$_{1-4}$ alkyl, 5- to 6-membered heteroaryl, or 5- to 6-membered heteroaryl substituted C$_{1-4}$ alkyl group; wherein the alkyl, alkenyl, alkynyl, cycloalkyl, heterocyclic group, aryl, or heteroaryl are optionally substituted by 1-3 X$^2$; or R$^5$ and R$^6$ together with the nitrogen atom to which they are attached form 4- to 5-membered heterocyclic group or 7- to 12-membered heterocyclic group comprising additional 1-2 hetero atoms selected from N, O or S, wherein the heterocyclic group is optionally substituted by 1-2 X$^3$.

5. The compound of claim 1, wherein R$^2$ is NH(CR$^7$R$^8$)$_n$—R$^6$ or O(CR$^7$R$^8$)$_n$—R$^6$; R$^6$ is C$_{2-4}$ alkenyl, C$_{2-4}$ alkynyl, C$_{2-4}$ alkynyl substituted C$_{1-4}$ alkyl, C$_{3-12}$ cycloalkyl, C$_{3-8}$ cycloalkyl substituted C$_{1-4}$ alkyl, 4- to 12-membered heterocyclic group comprising 1 to 3 hetero atoms selected from N, O and S, C$_{1-4}$ alkyl containing 4- to 12-membered heterocyclic group, 6-membered aryl, 6-membered aryl substituted C$_{1-4}$ alkyl, 5- to 6-membered heteroaryl, or 5- to 6-membered heteroaryl substituted C$_{1-4}$ alkyl, wherein the alkyl, alkenyl, alkynyl, cycloalkyl, heterocyclic group, aryl, or heteroaryl is optionally substituted by 1-3 X$^2$.

6. The compound of claim 1, wherein R$^2$ is NHR$^6$ or OR$^6$; R$^6$ is C$_{2-4}$ alkynyl substituted C$_{1-4}$ alkyl, C$_{3-12}$ cycloalkyl, C$_{3-8}$ cycloalkyl substituted C$_{1-4}$ alkyl, 4- to 12-membered heterocyclic ring containing 1-3 heteroatoms selected from N, O and S, 4- to 12-membered heterocyclic group substituted C$_{1-4}$ alkyl group.

7. The compound of claim 1, wherein R$^2$ is NHR$^6$ or OR$^6$; R$^6$ is C$_{3-8}$ cycloalkyl group, 3- to 8-membered heterocycloalkyl comprising 1-3 heteroatoms selected from N, O and S, C$_{1-4}$ alkoxy substituted C$_{3-8}$ cycloalkyl, hydroxy substituted C$_{3-8}$ cycloalkyl, C$_{1-4}$ alkoxy substituted C$_{1-4}$ alkyl, C$_{3-8}$ cycloalkyl-substituted C$_{1-4}$ alkyl, 3- to 8-membered heterocycloalkyl substituted C$_{1-4}$ alkyl, or hydroxyl group-containing C$_{3-8}$ cycloalkyl substituted C$_{1-4}$ alkyl, wherein the alkyl, cycloalkyl, heterocyclic group is optionally substituted by 1-3 X$^2$.

8. The compound of claim 1, wherein the compound is of the structure of formula (II),

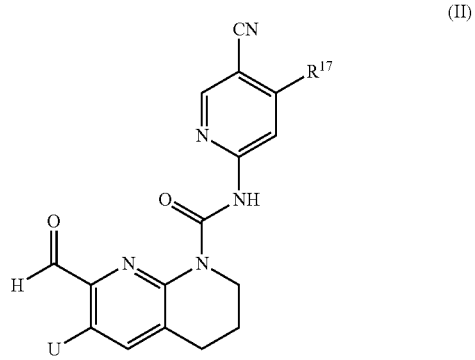

wherein R$^{17}$ is a group selected from the group consisting of

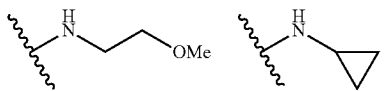

-continued
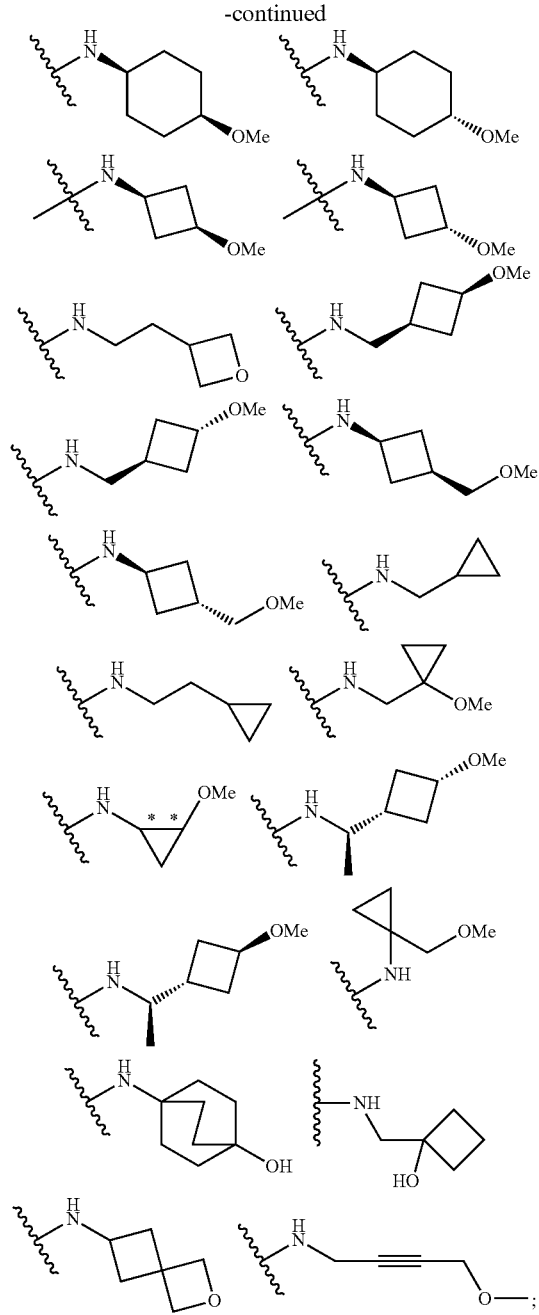
or R$^{17}$ is a group selected from the group consisting of
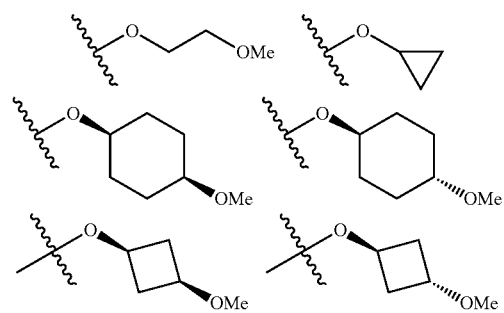
-continued
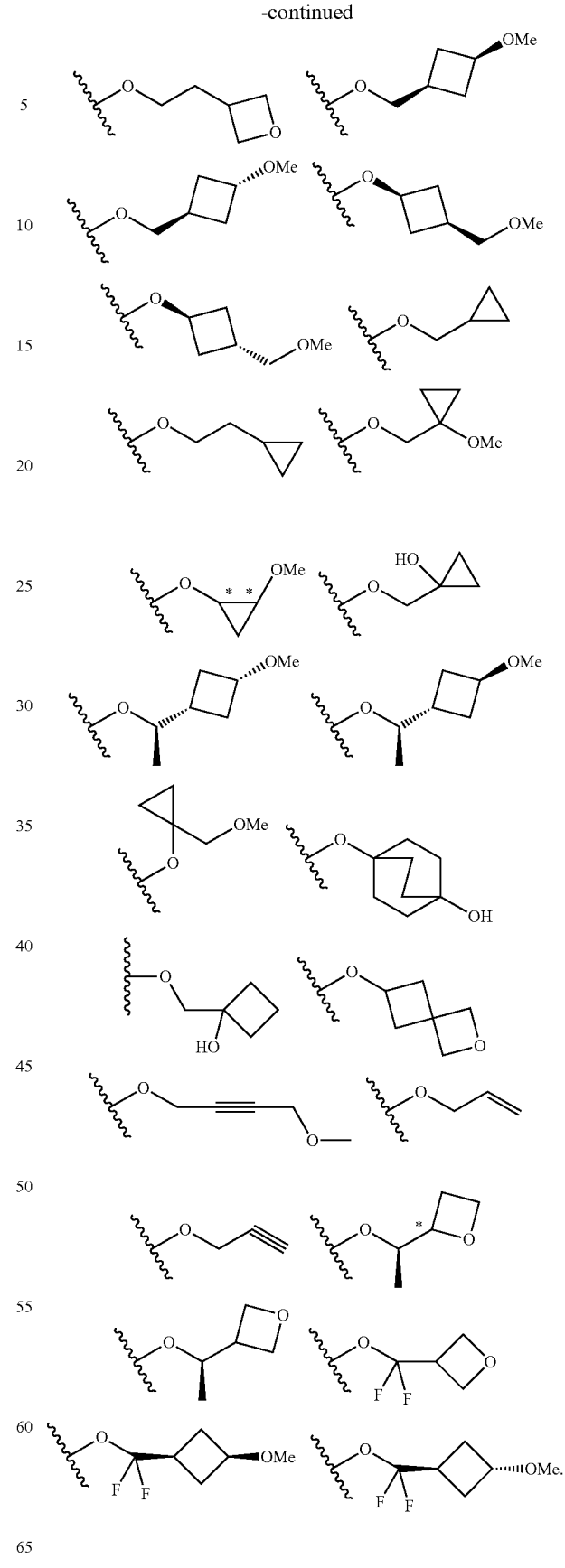

9. The compound of claim 1, wherein the compound is of the structure of formula (II),
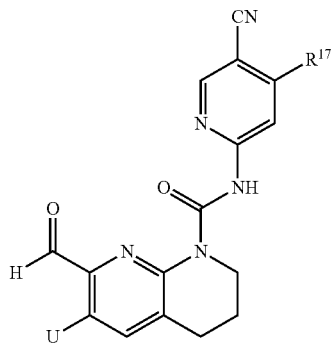
(II)
wherein R¹⁷ is a group selected from the group consisting of
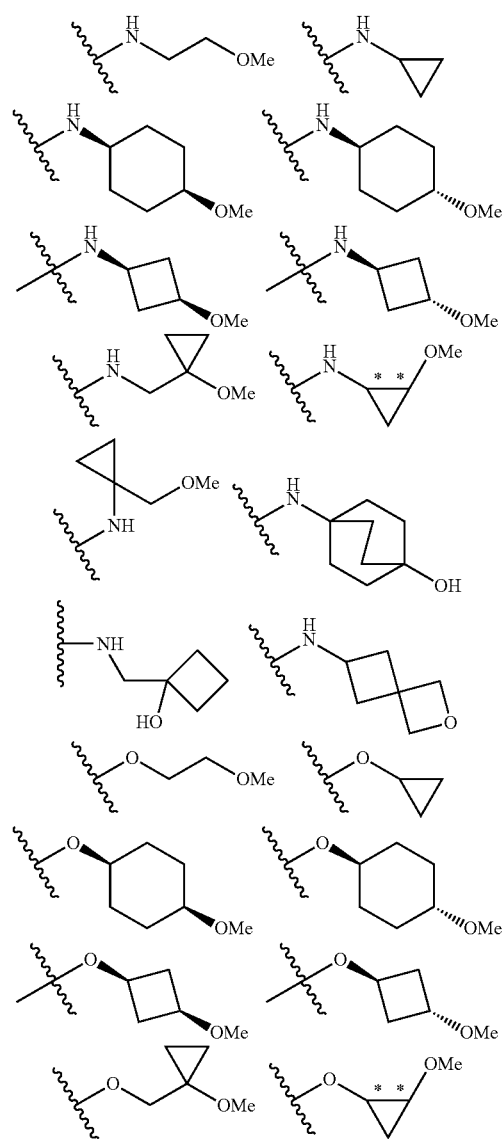
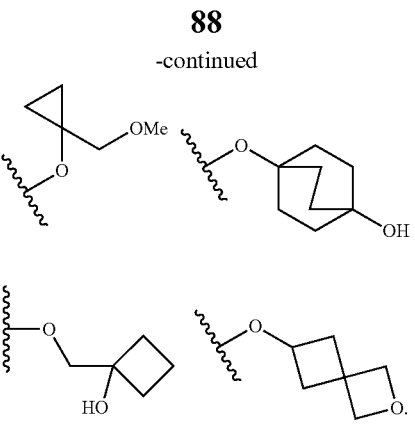
10. A compound selected from the group consisting of
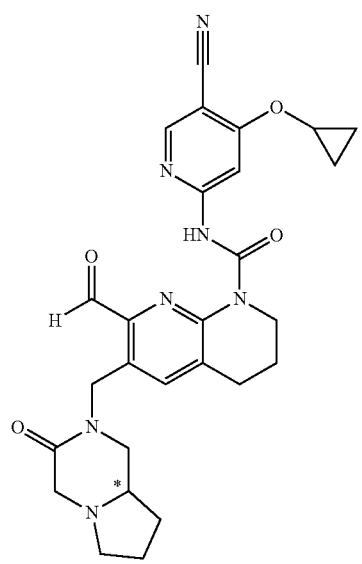
6
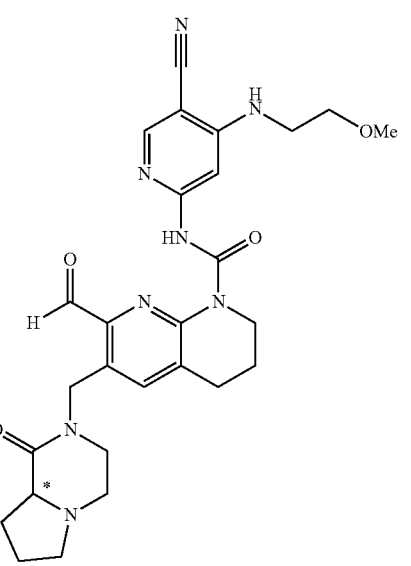
10

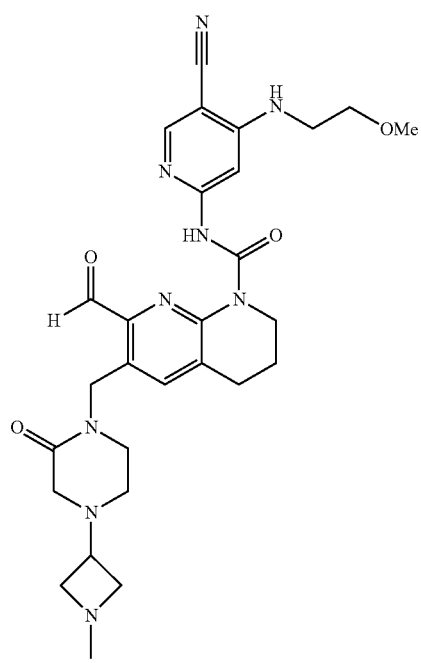
11
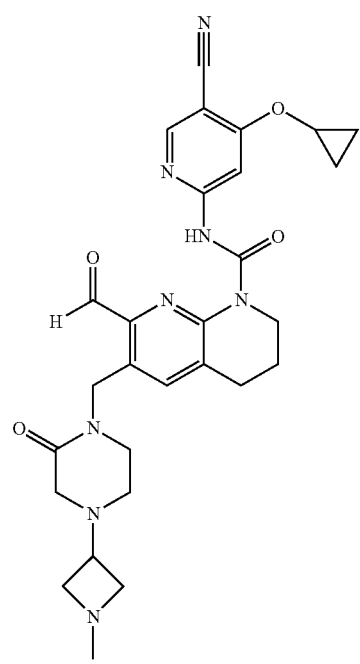
16
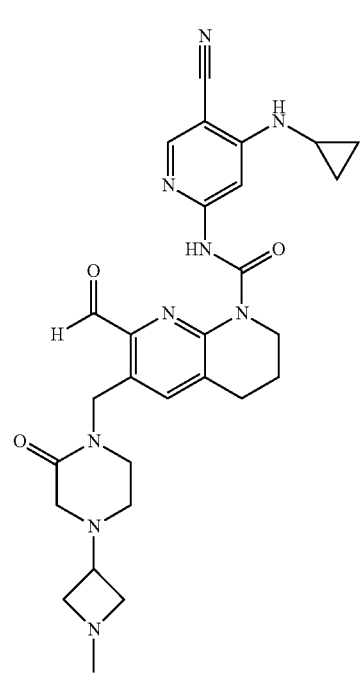
15
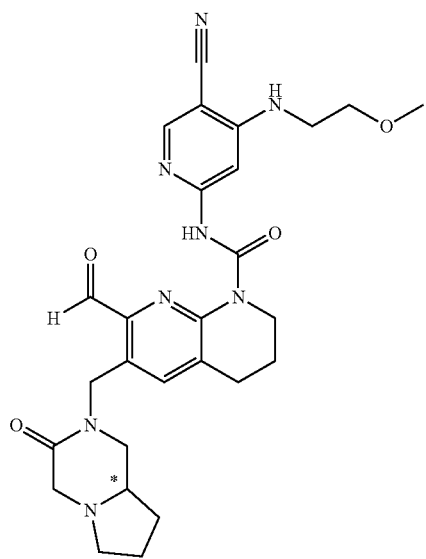
18

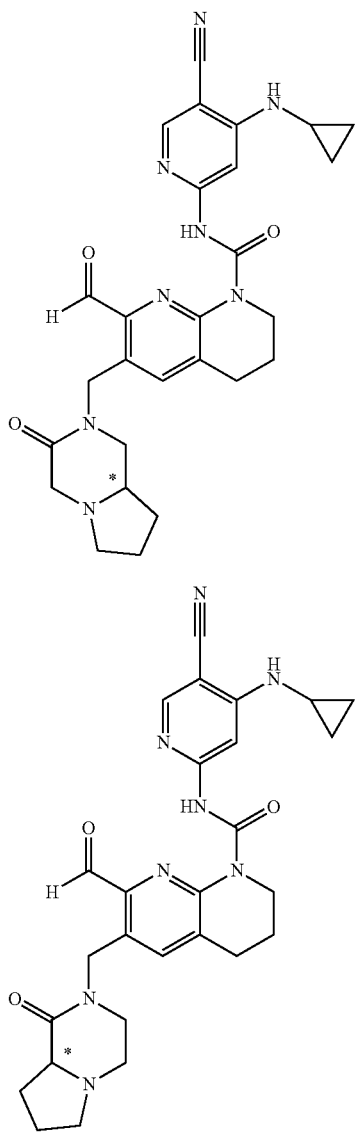

wherein,

"*" indicates a chiral center.

11. A method for treating diseases associated with FGFR4 activity or expression in a subject in need thereof, the method comprising administering to the subject a therapeutically effective amount of the compound of formula (I) according to claim 1; wherein the disease is a tumor, and the tumor is selected from the group consisting of lung cancer, bladder cancer, breast cancer, gastric cancer, liver cancer, salivary gland sarcoma, ovarian cancer, prostate cancer, cervical cancer, epithelial cell carcinoma, multiple myeloma, pancreatic cancer, lymphoma, chronic myelogenous leukemia, lymphocytic leukemia, and cutaneous T-cell lymphoma.

12. A pharmaceutical composition, comprising: (i) an effective amount of the compound of claim 1, or the pharmaceutically acceptable salt thereof, and (ii) a pharmaceutically acceptable carrier.

13. A method of inhibiting FGFR4 kinase activity, comprising-administering an inhibitory effective amount of a compound of formula (I) of claim 1 or a pharmaceutically acceptable salt thereof to an inhibition subject.

14. A method of preparing a compound according to claim 1, wherein the method comprises:

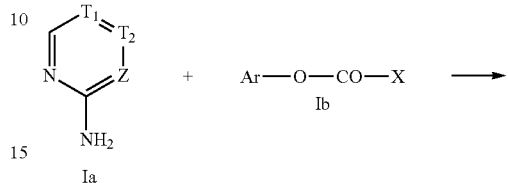

(1) in an inert solvent, reacting compound Ia—with compound Ib in the presence of a base, to form compound Ic;

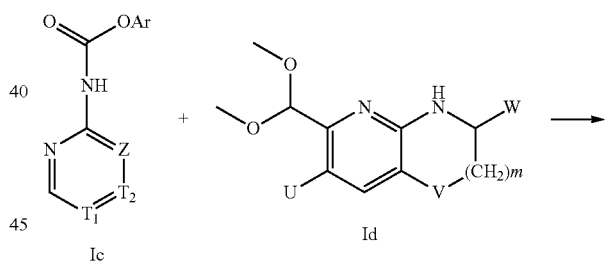

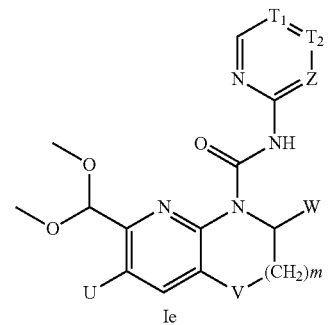

(2) in an inert solvent, reacting compound Ic with compound Id to form compound Ie;

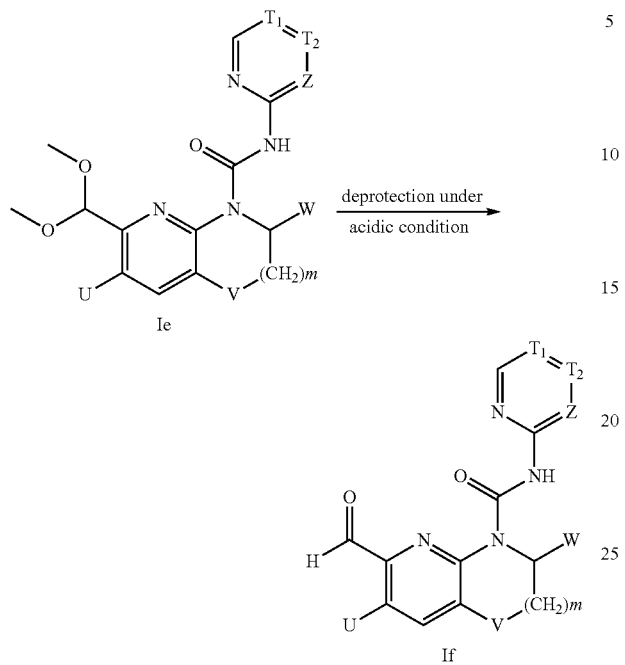

(3) in an inert solvent, deprotecting compound Ie under an acid to obtain compound If; and when the compound Ia is compound Ik, the method further comprising:

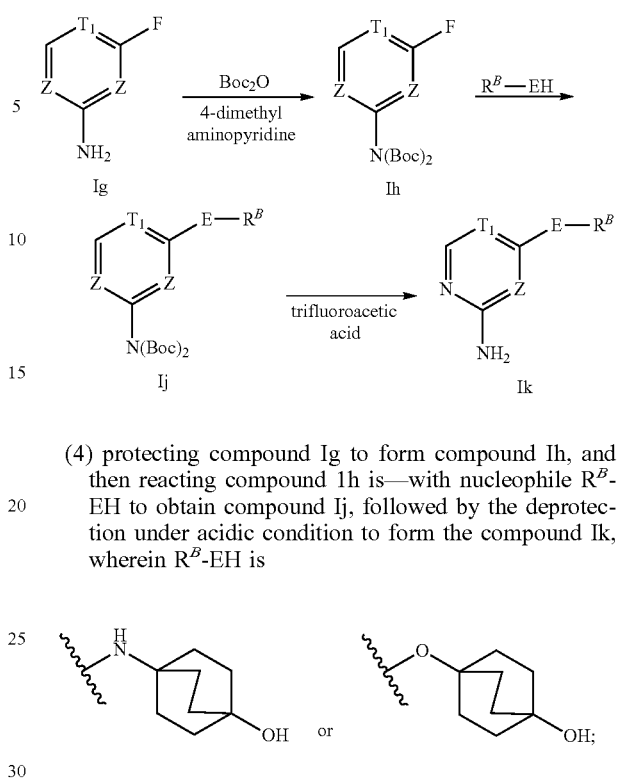

(4) protecting compound Ig to form compound Ih, and then reacting compound 1h is—with nucleophile $R^B$-EH to obtain compound Ij, followed by the deprotection under acidic condition to form the compound Ik, wherein $R^B$-EH is

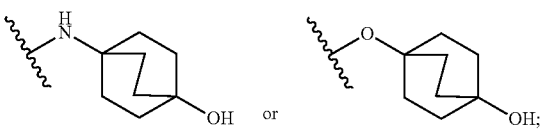 [SMILES: *NC12CCC(O)(CC1)CC2 ; *OC12CCC(O)(CC1)CC2]

in the above formulae, Ar is an aryl group, X is a halogen, and the other groups are defined as in claim 1.

* * * * *